(12) United States Patent
Solari

(10) Patent No.: US 11,037,669 B2
(45) Date of Patent: Jun. 15, 2021

(54) SYSTEM AND METHOD FOR CALCULATING, DISPLAYING, MODIFYING, AND USING PERSONALIZED NUTRITIONAL HEALTH SCORE

(71) Applicant: NESTEC S.A., Vevey (CH)

(72) Inventor: Soren Solari, Lafayette, CA (US)

(73) Assignee: Societe Des Produits Nestle S.A., Vevey (CH)

( * ) Notice: Subject to any disclaimer, the term of this patent is extended or adjusted under 35 U.S.C. 154(b) by 523 days.

(21) Appl. No.: 15/515,047

(22) PCT Filed: Oct. 2, 2015

(86) PCT No.: PCT/EP2015/072804
§ 371 (c)(1),
(2) Date: Mar. 28, 2017

(87) PCT Pub. No.: WO2016/050958
PCT Pub. Date: Apr. 7, 2016

(65) Prior Publication Data
US 2018/0233223 A1 Aug. 16, 2018

Related U.S. Application Data

(60) Provisional application No. 62/059,534, filed on Oct. 3, 2014, provisional application No. 62/188,896, filed on Jul. 6, 2015.

(51) Int. Cl.
*G16H 20/60* (2018.01)
*G16H 50/30* (2018.01)

(52) U.S. Cl.
CPC ............ *G16H 20/60* (2018.01); *G16H 50/30* (2018.01)

(58) Field of Classification Search
None
See application file for complete search history.

(56) References Cited

U.S. PATENT DOCUMENTS

| 8,777,624 B2 * | 7/2014 | Klein | G09B 5/02 |
| | | | 434/127 |
| 2007/0269557 A1 * | 11/2007 | Culver | G06Q 10/087 |
| | | | 426/72 |

(Continued)

FOREIGN PATENT DOCUMENTS

WO    WO-2012047940 A1 *    4/2012    ............. G16H 20/60

OTHER PUBLICATIONS

Jeppe Wojcik, Three beers a day keep the doctor away, sciencenordic. com (2012), http://sciencenordic.com/three-beers-days-keep-doctor-away (last visited Jun. 14, 2019). (Year: 2012).*

*Primary Examiner* — Elaine Gort
*Assistant Examiner* — Nicholas Akogyeram, II
(74) *Attorney, Agent, or Firm* — K&L Gates LLP

(57) ABSTRACT

The disclosed system calculates a single score for a consumable that indicates the nutritional health of that consumable. Nutritional health in one embodiment is an indication of whether nutrients within a consumable are within a healthy range that is specific to a user based on a recommended caloric intake. The system determines the impact on the individual's nutritional health by determining whether the nutritional content of a consumable falls within a range customized to the individual. The disclosed system thus tracks and displays the impact of consumables on individuals personalized nutritional requirements. The disclosed system also generates nutritional advice, enabling the individual to discover the impact of changes to nutritional habits on the individual's overall nutritional health. In an embodiment, the disclosed system determines and displays con- (Continued)

sumables that would need to be consumed to meet an individual's nutritional health needs over a specified period, such as in a given day.

12 Claims, 15 Drawing Sheets

(56) References Cited

U.S. PATENT DOCUMENTS

| | | | |
|---|---|---|---|
| 2010/0100392 A1 | 4/2010 | Rothman et al. | |
| 2011/0202359 A1* | 8/2011 | Rak .................. | G16H 70/00 705/1.1 |
| 2012/0083669 A1* | 4/2012 | Abujbara ............ | G16H 20/60 600/300 |
| 2013/0108993 A1* | 5/2013 | Katz .................. | G09B 23/28 434/127 |
| 2013/0216982 A1* | 8/2013 | Bennett ............. | A61B 5/7275 434/127 |
| 2014/0106312 A1* | 4/2014 | Klein ................ | G09B 19/0092 434/127 |
| 2014/0156308 A1 | 6/2014 | Ohnemus et al. | |
| 2014/0255882 A1* | 9/2014 | Hadad ............... | G16H 20/60 434/127 |
| 2015/0017614 A1* | 1/2015 | Stein ................. | G09B 19/0092 434/127 |
| 2015/0161910 A1* | 6/2015 | Bailor ............... | G09B 19/0092 434/127 |

* cited by examiner

FIG. 4 (400)

| DRI_name (401) | weight (402) | sensitivity (403) |
|---|---|---|
| Calcium | 0.02380952 | 2 |
| Carbohydrate | 0.02380952 | 2 |
| Food_Folate | 0.02380952 | 2 |
| Fiber | 0.02380952 | 2 |
| Iron | 0.02380952 | 2 |
| Magnesium | 0.02380952 | 2 |
| Niacin | 0.02380952 | 2 |
| Pantothenic_acid | 0.02380952 | 2 |
| Phosphorus | 0.02380952 | 2 |
| Potassium | 0.02380952 | 2 |
| Protein | 0.02380952 | 2 |
| Riboflavin | 0.02380952 | 2 |
| Thiamin | 0.02380952 | 2 |
| Vit_A | 0.02380952 | 2 |
| Vit_B12 | 0.02380952 | 2 |
| Vit_B6 | 0.02380952 | 2 |
| Vit_C | 0.02380952 | 2 |
| Vit_D | 0.02380952 | 2 |
| Vit_E | 0.02380952 | 2 |
| Water | 0.02380952 | 2 |
| Zinc | 0.02380952 | 2 |
| Saturated_Fat | 0.1 | 1 |
| Cholesterol | 0.1 | 1 |
| Sugar | 0.1 | 1 |
| Total_Fat | 0.1 | 1 |
| Sodium | 0.1 | 1 |

FIG. 5 (500)

| DRI_name | Units | Female 31-50 LHR | Female 31-50 UHR | Female 9-13 LHR | Female 9-13 UHR |
|---|---|---|---|---|---|
| Alpha_carotene | ug/d | 16800 | na | 14400 | na |
| Beta_carotene | ug/d | 8400 | na | 7200 | na |
| Beta_Cryptoxanthin | ug/d | 16800 | na | 14400 | na |
| Biotin | ug/d | 30 | na | 20 | na |
| Calcium | mg/d | 1000 | 2500 | 1300 | 3000 |
| Carbohydrate | % | 45 | 65 | 45 | 65 |
| Carbohydrate_g | g/d | 130 | na | 130 | na |
| Chloride | mg/d | 2300 | 3600 | 2300 | 3400 |
| Cholesterol | mg/d | 0 | 300 | 0 | 300 |
| Choline | mg/d | 425 | 3500 | 375 | 2000 |
| Chromium | ug/d | 25 | na | 21 | na |
| Copper | mg/d | 0.9 | 10 | 0.7 | 5 |
| Energy | % | 90 | 110 | 90 | 110 |
| Fiber | g/d | 25 | na | 26 | na |
| Floride | mg/d | 3 | 10 | 2 | 10 |
| Folic_Acid | ug/d | 240 | 600 | 180 | 3600 |
| Food_Folate | ug/d | 400 | 1000 | 300 | 600 |
| Histidine | mg/g | 18 | na | 18 | na |
| Iodine | ug/d | 150 | 1100 | 120 | 600 |
| Iron | mg/d | 18 | 45 | 8 | 40 |
| Isoleucine | mg/g | 25 | na | 25 | na |
| Leucine | mg/g | 55 | na | 55 | na |
| Lysine | mg/g | 51 | na | 51 | na |
| Magnesium | mg/d | 320 | 670 | 240 | 590 |
| Manganese | mg/d | 1.8 | 11 | 1.6 | 6 |
| Methoinine_cysteine | mg/g | 25 | na | 25 | na |
| Molybdenum | ug/d | 45 | 2000 | 34 | 1100 |

FIG. 6

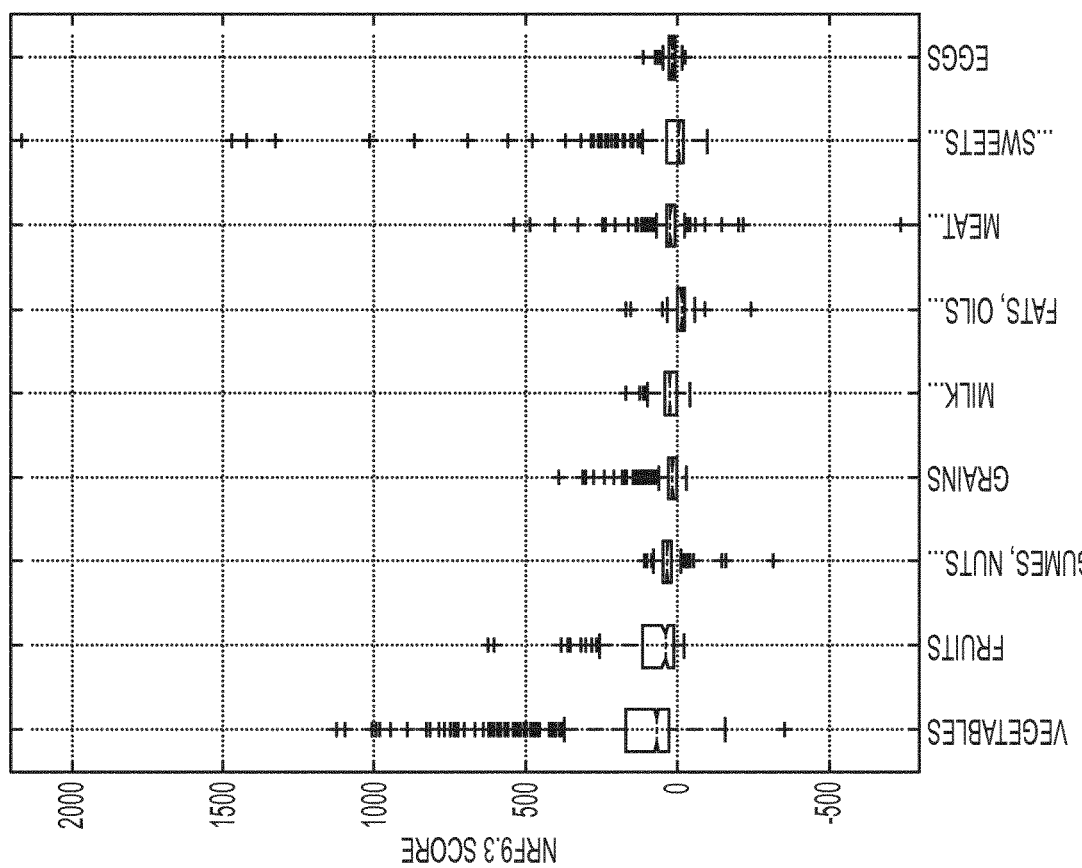
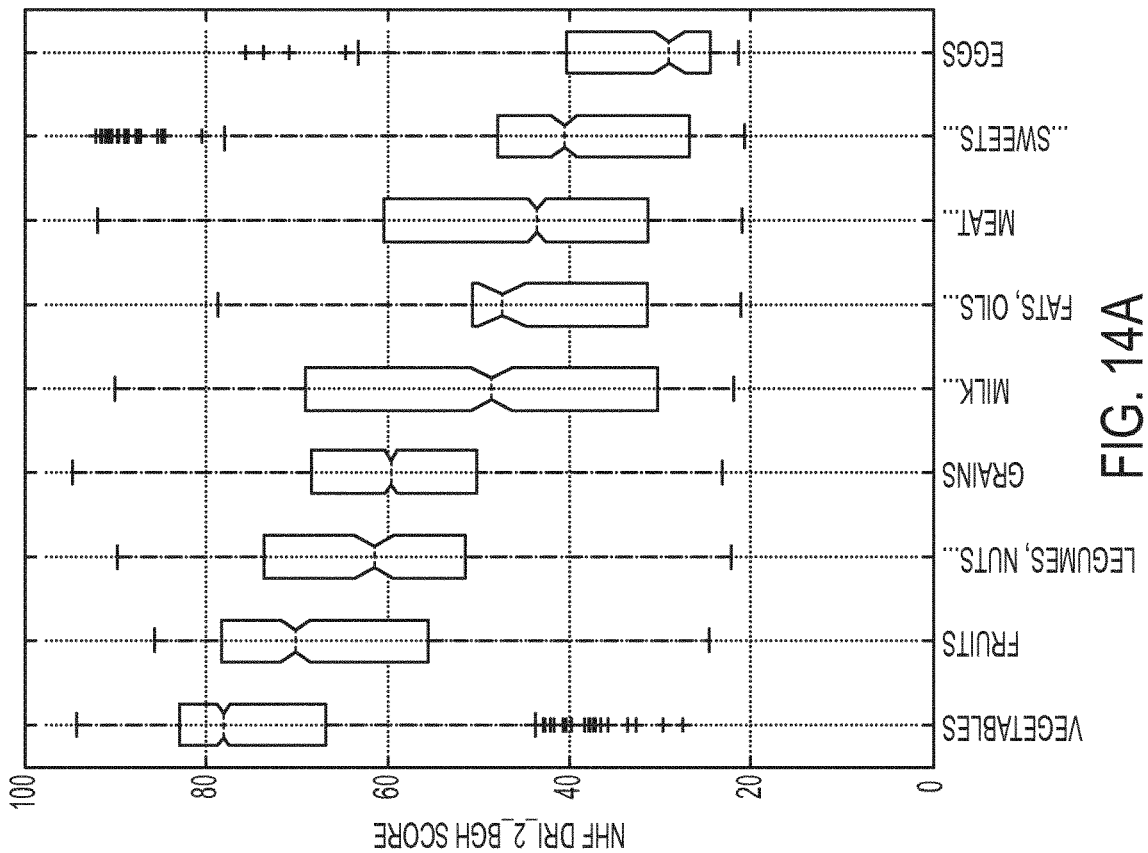
FIG. 14A
FIG. 14B

SYSTEM AND METHOD FOR CALCULATING, DISPLAYING, MODIFYING, AND USING PERSONALIZED NUTRITIONAL HEALTH SCORE

CROSS REFERENCE TO RELATED APPLICATIONS

The present application is a National Stage of International Application No. PCT/EP2015/072804, filed on Oct. 2, 2015, which claims priority to U.S. Provisional Patent Application No. 62/059,534, filed Oct. 3, 2014, and U.S. Provisional Patent Application No. 62/188,896, filed Jul. 6, 2015, the entire contents of which are being incorporated herein by reference.

PRIORITY CLAIM

This application is priority to and the benefit of U.S. Provisional Patent Application No. 62/188,896, filed Jul. 6, 2015, and U.S. Provisional Patent Application No. 62/059,534, filed on Oct. 3, 2014, the entire contents of which are incorporated herein by reference in their entirety.

COPYRIGHT NOTICE

A portion of the disclosure of this patent document contains material that is subject to copyright protection. The copyright owner has no objection to the photocopy reproduction of the patent document or the patent disclosure in exactly the form it appears in the Patent and Trademark Office patent file or records, but otherwise reserves all copyright rights whatsoever.

TECHNICAL FIELD

The present disclosure relates in general to systems and methods for calculating the impact of consumables on nutritional health of populations. More specifically, the present disclosure relates to systems and methods for determining whether the nutritional content or other trackable measurements of a particular consumable, such as an ingredient, a food, a meal, or a diet, falls within a plurality of so-called healthy ranges customized to an individual. The disclosed system can recommend consumables that help an individual meet his or her goals by ensuring that consumed nutrients are within a healthy range for a given time period, such as for a given day or week.

BACKGROUND

Making healthier food choices can help prevent non-communicable diseases such as obesity, cardiovascular disease, diabetes and some cancers. Guidelines, like the *Dietary Guidelines for Americans*, provide general population recommendations for healthful eating. Such guidelines can drive content for nutrition labels, health claims, nutrition education, menu planning, as well as marketing and advertising on food products. However, these generalized guidelines are not designed to provide personalized nutrition recommendations at the macro- or micronutrient level.

Substantial efforts have been made to quantify and track the impact of particular consumables, such as ingredients, foods, meals, or diets, on the overall health of individuals. For example, every five years since 1980, the United States Department of Agriculture (USDA) along with the Department of Health and Human Services (HHS) releases so-called Dietary Guidelines for Americans. The USDA states that these Guidelines provide advice about consuming fewer calories, making informed food choices, and being physically active to attain and maintain a healthy weight. (http://www.cnpp.usda.gov/DietaryGuidelines).

While the Dietary Guidelines provide a framework into which individuals can seek to fit themselves, the Guidelines are nonetheless an inadequate tool to enable individuals to track the actual impact of consumables on overall nutritional health. Specifically, because the Guidelines are nothing more than guidelines, it is difficult if not impossible for individuals to determine the actual nutritional goals they should be attempting to achieve, and whether/when those goals have been achieved. That is, it is difficult for individuals to determine healthy amounts of particular nutrients that should be consumed over a given time period and to track whether those healthy amounts have in fact been consumed.

Moreover, the Guidelines do not enable the determination of the impact of a particular consumable (e.g., an ingredient in a food or a food in a meal) on the overall nutritional health of an individual, and do not facilitate an advisory function whereby the items needed to reach an individual's nutritional health goals can be suggested based on items already consumed. To the extent the Guidelines provide any advisory function, they give heuristic recommendations, such as "eat more fruits and vegetables."

To assist nutrition professionals and individuals in navigating more specific nutrition intake goals, food scientists have attempted to develop scoring systems to rate the healthfulness or unhealthfulness of foods, meals, and diets. However, reviewers have noted these are often methodologically weak. In certain existing schemes that attempt to apply scores to foods, a single score is determined and applied to the food itself without consideration of the individual consuming the food or the amount of the food consumed. This is ineffective, as the nutritional health of a given food depends both on the individual consuming the food (e.g., the caloric or other nutritional needs of the individual) and the amount of the food consumed (e.g., a half-cup of ice cream versus a half-gallon of ice cream). Thus, the static, generic scoring functionality provided according to these known schemes is ineffective at providing a true indicator of the nutritional impact of a food item.

Nutritional health also depends on what has been consumed previously. For example, a single cookie is not inherently good or bad for nutritional health. In fact, that single cookie may, in the aggregate, be a healthy choice if a nutritionally balanced diet has already been consumed. Conversely, consuming 50 cookies is likely to be nutritionally unhealthy. Known systems do not recognize this fact; instead, they generally treat certain foods as either "good" or "bad."

Moreover, known nutrition profiling systems seek to calculate and apply points to foods or meals according to general guidelines. For example, some known systems add 5 points to a food or meal if the saturated fat content is above a certain threshold. Under these systems, the user adds these points up for a given time period (day, week) to determine a score. Such systems suffer from drawbacks in that they are not data driven but require an expert panel of nutritionist to heuristically set points/limits. As a result, in these systems, the final score has little meaning other than as a reflection of a general notion of the panel's opinion of health. Moreover, in such systems, the points are usually (if not always) rounded to integers to make the scoring system more interpretable to users. That the scores are thus discretized means that relatively large scoring changes can result from infinitesimally small changes in diet.

In other known systems, nutritional balance scores have been utilized to drive indications of the completeness of the nutrients consumed. These systems may utilize DRI values (i.e., daily reference intake limits based on a user profile) but only score a subset of nutrients (typically vitamins and minerals) with a desired minimal limit. The global completeness of consumed vitamins and minerals can be scored such that a score between 0 and 100 is given, where 100 is given if all vitamins and minerals are consumed above their limit and some fraction of 100 given based on the under-consumption of nutrients. These scoring systems do not take into account healthy ranges and are not capable of accounting for upper limits beyond which consumption is unhealthy. Many vitamins and minerals have toxic levels of consumption that are unhealthy and these systems cannot account for unhealthy high doses. Additionally macro nutrients like fats and sugars that may be beneficially limited are not taken into account. Finally, and importantly, the utilization of only lower limit thresholds to produce nutritional scores results in scores that cannot be optimized as a function of consumption, because the score only increases as consumption increases.

Existing systems and schemes have typically sought to classify nutrients as either so-called "qualifying" nutrients or so-called "disqualifying" nutrients. In general, qualifying nutrients have been viewed as having a lower limit, such that exceeding the lower limit is viewed as "good" and being below the lower limit is viewed as "bad." Similarly, disqualifying nutrients have been viewed as having an upper limit, such that remaining below the upper limit has been generally viewed as "good" while exceeding the upper limit has generally been viewed as "bad." These schemes are inadequate because they fail to provide a common mechanism for tracking the impact on all kinds of nutrients (or other measurable aspects of foods) that can account for overconsumption where appropriate.

Known systems and schemes are also deficient because they are not constructed at an appropriate level of granularity to improve scoring for heterogeneous populations or individuals. Instead, one set of values is used to define a single score for populations and all individuals. This lack of granularity prohibits known systems and schemes from being customized to different individual users with different individual nutritional needs.

What is needed is a system that calculates customized nutritional health scores based on adjustable sets of nutrients and adjustable weights/sensitivity values to design score profiles for a particular use case or purpose, such as for performance in athletics.

What is further needed is a system that calculates a plurality of values for this nutritional health score taking into account nutrient requirements specific to a particular individual, such that the score is customized to the individual for different amounts of foods consumed.

What is still further needed is a system that can calculate the impact of either adding or removing consumables on the individual's overall nutritional health score, such that the system can make recommendations of additional consumables the individual can consume (or can remove from his or her diet) to ensure that all necessary nutrients are consumed in healthy amounts for a given period, such as for a given day or week.

The present disclosure describes a nutritional health scoring system that satisfies the needs described above. Thus, the present disclosure describes a system and methods that overcome the shortcomings of prior nutritional management techniques described above.

SUMMARY

In various embodiments, the system disclosed herein calculates one or more nutritional health scores tailored to an individual based on the individual's caloric intake range and corresponding healthy ranges of nutrient intakes for a given time period. The calculated scores are based on whether nutrient intake falls within a healthy range, and are affected not only by under-consumption of nutrients but also by over-consumption of nutrients. These scores enable individuals to determine whether they are consuming enough nutrients, and to the extent they are not, to determine which additional nutrients need to be consumed. The disclosed system also makes suggestions for adding or removing consumables that, if consumed (or removed from a diet), will provide the individual with nutrients in amounts determined to be within healthy nutrient ranges for that individual.

In various embodiments, the nutritional health scores calculated by the disclosed system indicate the nutritional health of the individual for whom the scores are calculated. Nutritional health as used in these embodiments refers to the extent to which nutrients consumed by an individual are within the individual's healthy nutrient ranges over a specified period of time. In these embodiments, exemplary nutrients can include micro-nutrients (e.g., calcium, cholesterol, fiber) and/or macro-nutrients (e.g., carbohydrates, protein, and saturated fat).

Various embodiments of the disclosed system are based on the premise that all nutrients have healthy ranges for consumption. That is, embodiments of the disclosed system are based on the premise that there are no good or bad nutrients, and hence no intrinsically good or bad foods. Instead, for each nutrient (or food), a person either consumes an amount that is inside or outside a healthy range for consumption. In these embodiments, the healthy ranges of nutrients can be different for different individuals, meaning that an assessment of nutritional health depends on the needs of a specific individual. For example, the healthy ranges of particular nutrients can vary for different people depending on whether a person has diabetes, whether a person is obese, whether a person is a critical care patient, whether a person has allergies, or whether a person is an athlete. As described below, by varying the healthy range for different nutrients in a way that is customized to the person, the calculated nutritional health score provided by the disclosed system is also customized to each individual user.

Various embodiments of the disclosed system display a dashboard or other appropriate user interface to a user that is customized based on the user's nutritional needs, such as the user's caloric intake or a set of determined applicable DRI (daily reference intake) values. The disclosed system calculates scores indicative of the nutritional value of a consumable, such as an ingredient, a food, a meal, or a diet, and displays the scores to the user via the dashboard. In these embodiments, the calculated scores are functions of the amount of food (and therefore nutrients) consumed over a given time period and are also tailored to an individual user such that the scores indicate the nutritional value of the consumable to a single, particular individual as opposed to indicating the general nutritional value of a consumable to a group of individuals. In such embodiments, the disclosed system calculates nutritional value scores by determining whether nutrient content of a consumable is within a range tailored to the user for each nutrient contained in the consumable. The system then composes or aggregates the component scores into aggregate scores based on a personalized set of weighting parameters ascribed to each nutrient that reflect the overall nutritional health impact of the consumable for the individual. In various embodiments, therefore, it can be said that the nutritional health scores represent the extent to which nutrient consumption is within defined nutritional health ranges as a weighted average of individual nutrient scores outside nutrient healthy ranges.

In various embodiments, the disclosed system is configured to calculate and display multiple nutritional health scores to provide a complete picture of the nutritional impact of consuming certain consumables. In one embodiment, the scores are calculated according to an equation that takes into account the amount of the food consumed over a given time period and also characteristics of the individual for whom the scores are calculated. In one embodiment, for a particular individual, multiple scores could be given for different purposes. In one embodiment, the disclosed system calculates at least two different scores for a given consumable: one score indicating the nutritional content of the current or actual amount of food consumed, and one score that is a highest possible score for that food, where the amount of food consumed for a set period of time is variable. Thus, for example, the system may provide an indication that since an individual consumed ¼ pound of chicken in a day, his score is X, but his score for chicken would be at a maximum value of Y>X if he consumed an additional ¼ pound of chicken in the day. In other words, the disclosed system can provide the score of a meal as built, and can provide an optimal score that might be achieved if additional food items are consumed or if certain consumed foods are removed or reduced from a diet.

It should thus be appreciated that the disclosed system provides the advantage over known systems in that the particular food consumed does not have a single, static score, but rather has a scoring profile or function that is tailored to an individual that can be used to determine scores for the food under different conditions, such as different caloric intake requirements or different amounts of food consumed.

Various embodiments of the disclosed system also provide an advisory functionality. In these embodiments, after calculating a nutritional health score for a particular individual based on ranges that define that individual's nutrient and caloric needs for a given time period (e.g., a given day), the disclosed system suggests combinations of consumables that can be consumed for the remainder of the time period to result in the individual obtaining the nutrients he or she requires. For example, if an individual indicates that he or she has eaten certain foods for breakfast and lunch, the disclosed system can suggest a dinner menu that will ensure the individual gets all the nutrients he or she needs in the day while still consuming an amount of calories that falls within a caloric intake range applicable to the individual. In this embodiment, the recommendations provided by the disclosed system are optimized; the system determines the impact on the overall nutritional health score of a plurality of foods stored in its database, and suggests foods that result in an optimal increase to the nutritional health score.

For each consumable or group of consumables indicated by the individual, the disclosed system determines whether the tracked nutrients that make up an active nutrient profile that are present in that consumable or group of consumables are inside or outside the range for that nutrient that is ideal for the particular individual. In one embodiment, the system determines the total nutrient content of the consumable or group of consumables before determining a nutrient health score for each nutrient. In this embodiment, the nutrient health score for each nutrient is less than 1 (or some other maximum) if the nutrient content is outside the range for that individual, and is 1 (or some other maximum) if the nutrient content is in the range for that individual. The amount by which the nutritional health score differs from 1 (or some other maximum) indicates the extent to which the nutrient in a consumable is outside the range determined to be ideal for an individual. This scoring calculation also takes into account both the amount by which a nutrient is under-consumed (i.e., is consumed in amount less than a healthy range for the nutrient) and an amount by which the nutrient is over-consumed (i.e., is consumed in an amount greater than the healthy range for the nutrient).

Given the component nutritional health scores for the individual nutrients of a consumable, the disclosed system further calculates an aggregate nutritional health score by computing a weighted average of the scores for the nutrients. In various embodiments, this is done by assigning a weighting value to each nutrient in the scoring profile, multiplying the nutritional health score for that nutrient by the weight, and summing the scores of all the scores of the nutrients in the consumables. In an embodiment, the weighting scores sum to 100. As a result, the overall nutritional health score in this embodiment will be a number less than or equal to 100. If the component nutritional health scores for each nutrient in the consumable are each 1 (meaning that each nutrient of the consumable is within the healthy range for the individual), the overall nutritional health score will be 100 (i.e., the sum of the weights of the nutrient components). Thus, in one embodiment, a score of 100 indicates that each of the individual's nutrient requirements are being met, and a number less than 100 indicates they are not, with the difference representing an amount by which the nutrient needs are not being met.

In various embodiments, the disclosed system determines a range for each nutrient for a particular individual. In these embodiments, the range is defined by a so-called lower healthy range value and a so-called upper healthy range value. It should be appreciated that because these values indicate amounts of nutrients, it is necessary that the determination of these values be performed in a frame of reference defined by a caloric intake amount. That is, if a lower healthy range value and an upper healthy range value are determined for a particular nutrient for the period of a day, the optimal caloric intake for the individual in a given day determines the lower and upper healthy range values the nutrient.

In various embodiments, the disclosed system stores some or all of the values needed to calculate nutritional health scores in one or more databases. For example, the disclosed system may store a table of caloric intake ranges for individuals based on the age, gender, and weight or Body Mass Index (BMI) of the individuals. In this embodiment, to determine an individual's caloric intake range for a given time period, the individual must provide the system with his or her age, gender, and weight or BMI. By performing a database lookup or calculation, the disclosed system can thus determine a caloric intake range for a given time period for a given individual.

In one embodiment, the disclosed system also stores normalized nutrient intake values based on caloric intake ranges. For example, for each nutrient tracked by the disclosed system, the system may store an indication of a lower healthy range value and an upper healthy range value at a reference caloric intake value, and may augment or decrease the lower and upper healthy range values as the caloric intake goal for a particular individual changes. In an embodiment, this augmenting or diminishing is linear, such that if the caloric intake increases by, for example, 25%, the lower and upper healthy range values increase by 25% as well. In other embodiments, the augmenting of lower and upper healthy range values is non-linear, such that relatively large changes to caloric intake values may result in relatively smaller changes to lower or upper healthy range values, or vice versa.

In one embodiment, the disclosed system enables a user to customize the nutritional health score to suit him or her by indicating his or her age, gender, and weight/BMI. This affects the caloric intake range for the individual, and thus affects the lower and upper healthy range values for each nutrient tracked by the system. In another embodiment, the disclosed system provides for further customization by enabling the user to specify additional information, such as body type, physical activity level, and the like. In this embodiment, the disclosed system uses these additional inputs to adjust not only optimal caloric intake ranges for different individuals, but also lower and upper healthy range values for nutrients tracked by the system. For example, if an individual indicates that he or she is athletic with a relatively high amount of athletic activity, the system may adjust the carbohydrate nutrient range upward to account for the individual's need for additional carbohydrates.

Accordingly, various embodiments of the disclosed system advantageously enable the calculation of a nutritional health score for an individual by performing the following steps:

(1) Storing indications of a plurality of nutrients to be scored (2) Storing indications of healthy ranges for each of the stored nutrients (3) Storing score sensitivity and score weight values for each nutrient (4) For a particular consumable, compute a nutrient health score for each component nutrient (5) Compute the aggregate nutritional health score for the consumable by applying weight values for each nutrient Various embodiments of the disclosed system further advantageously provide nutritional advice to users based on calculated nutritional health scores. For example, embodiments of the disclosed system determine amounts of nutrients that would be needed to place an individual in the healthy amount range for those nutrients. These embodiments then analyze a database of consumables (e.g., foods or ingredients) to determine combinations of consumables that will provide the needed amounts of nutrients to place the user in the healthy amount ranges while still remaining within the optimal caloric intake range for that individual.

Various embodiments of the disclosed system also improve on known systems by scoring all nutrients (and other measurable characteristics of food consumption) using a single scheme, regardless of whether those nutrients would have been classified as so-called "qualifying" nutrients or so-called "disqualifying" nutrients under prior known schemes. The fact that embodiments of the system disclosed herein take into account the impact of nutrient consumption both below a lower healthy range value and above an upper healthy range value advantageously tracks the impact of any amount of consumption of nutrients (or other measurable characteristics) using a common scoring mechanism.

In several above-described embodiments, a person's consumption of a consumable (e.g., food) product not only has an impact on an individual's biological health, but also has environmental, financial, or other impacts that can be measured and scored. In various embodiments, scores calculated as described herein reflect an individual's nutritional health and/or one or more additional trackable impacts of consumption. In other embodiments, the disclosed system tracks the consumption of non-food items such as oxygen and generates scores indicative of the impact of such consumption on an individual's health or other, non-individualized factors.

In one embodiment, the disclosed system and methods represent a framework within which more powerful computational and analytical systems can be built and within which existing systems can be placed with minor modification. The framework disclosed herein is generally referred to as a nutritional health framework that can, in various i) be used for nutrient profiling and personalized nutritional scoring system, or for other scientific nutritional analysis; (ii) measure the general nutritional health of a nutritional consumable on an individual or population; (iii) be used across multiple hierarchical levels from personalized nutritional scoring/diet optimization to population level comparisons; (iv) remove qualitative design elements based on "good" and "bad" nutrients/foods; (v) incorporate design through direct correlation with multiple simultaneous health measures in a pure data driven approach; (vi) integrate arbitrary measurable components so the complete general health of nutritional consumables can be scored; and/or (vii) be used to understand the impact of foods, meals, and diets in the context of their consumption amount over time. The overall goal of this initiative is a unified framework that will enable more robust collaborative science across disciplines, countries and use cases within the nutrition community.

Further advantages of the instant disclosure will be apparent from the following detailed description and associated figures.

BRIEF DESCRIPTION OF THE FIGURES

FIG. 4 is a schematic representation of a table stored in memory of an embodiment of the disclosed system that contains weighting and sensitivity parameters usable to design a scoring profile for a particular use case.

FIG. 5 is a schematic representation of a table stored in memory of an embodiment of the disclosed system that contains lower and upper healthy values for various nutrients tracked by the disclosed system.

FIG. 6 is a screen shot showing an example of the interface provided to a user of the disclosed system in one embodiment before any daily diet information is entered.

FIG. 14 illustrates Food and Nutrient Database for Dietary Studies ("FNDDS") foods scored by an example scoring profile.

DETAILED DESCRIPTION

Figure 1:
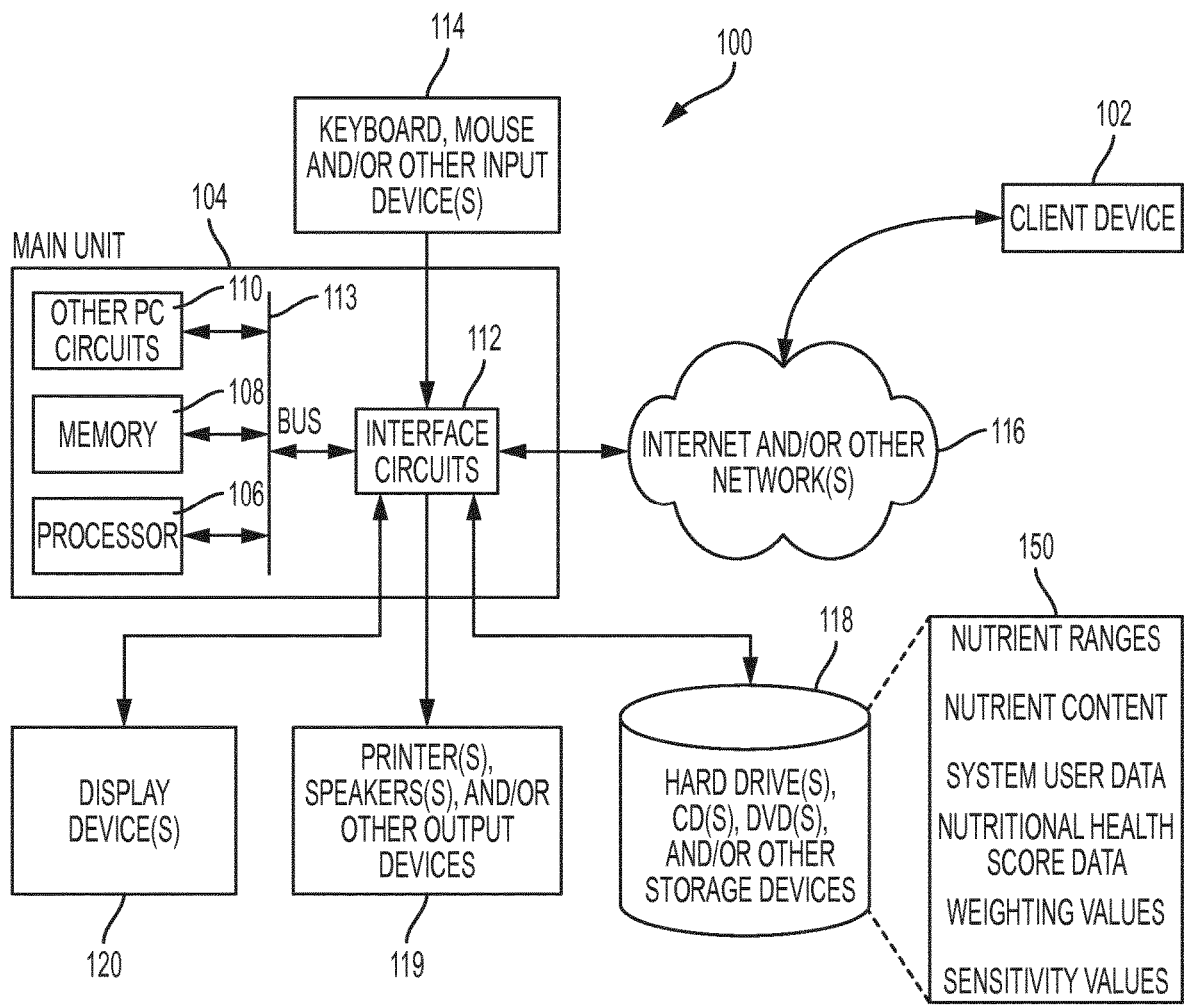
FIG. 1 is a block diagram illustrating an example of the electrical systems of a host device usable to implement the computerized nutritional health score system disclosed herein.

In general, the system disclosed herein calculates and displays scores indicating the impact of consumption of a consumable. These scores are tailored to the particular individual consuming the consumable, such that the score reflects the impact of the consumption given the individual's specific needs.

More particularly, in various embodiments, the system disclosed herein calculates and displays scores indicating the nutritional impact of consuming a consumable, such as a food, on the individual consuming the consumable. In these embodiments, the system determines and stores one or more indications of the needs of the individual for whom the scores are being calculated, such as by determining an optimal caloric intake range for an individual over a given period of time. The disclosed system may also determine and store indications of ranges of nutrients the individual should consume given the caloric intake range for a given period of time, such as by determining and storing a range of the amount of calcium (in mg) that the individual should consume in a day based on the caloric intake range for the day. The disclosed system then enables the user to indicate consumables (such as food items) that he or she has consumed or plans to consume. For each indicated food item, a database or datastore of the disclosed system stores an indication of the nutrient content per amount of that food item. The system uses the nutritional content information, multiplied by the amount of food item consumed over time, to determine the total nutritional intake over time for that particular food item.

In various embodiments, after determining the ranges of nutrients that are optimal for a particular individual at a particular caloric intake range in a particular time, and after knowing at least one consumed or to-be-consumed food item in that time period, the system calculates one or more nutritional health scores for the individual. These nutritional health scores indicate the nutritional impact of the indicated food item. In general, these scores are calculated by determining, for each nutrient tracked by the system, whether the nutrient content of the food item falls within the optimal or healthy range for that nutrient. In one embodiment, a nutrient health score is calculated for each nutrient contained in a food item. The system thereafter aggregates the nutrient scores using a weighting function to indicate the relative importance of each nutrient to the overall nutritional health of the individual. In an embodiment, the weighting function provides an aggregate nutritional health score on a scale of 0 to 100, where scores closer to 100 indicate greater fulfillment of the nutritional needs of the individual over a particular time period.

In one embodiment, the system calculates a plurality of scores for each food item indicated in the system. For example, the system may calculate one nutritional health score that shows the impact the indicated amount of a particular food item would have. The system may also calculate a nutritional health score that is determined to be the optimum score that can be achieved by consuming the particular food item. For example, if the indicated item is ¼ pound of chicken consumed in a day, the system may calculate and display a nutritional health score of 56 for ¼ pound of chicken in the day and may further indicate that an optimum score of 68 can be achieved by consuming more chicken, where that score can be achieved by consuming ½ pound of chicken in the day. As described in detail below, this optimum score may indicate that consuming more than ½ pound of chicken (i.e., over-consumption) results in a lower nutritional health score and thus constitutes achieving diminishing returns for the individual for whom the score is being calculated.

As further described in detail below, various embodiments the disclosed system also provide an advisory function, wherein the system suggests combinations of foods that will result in optimal nutritional health scores. For example, if a user accesses the system after breakfast and indicates the foods he or she had for breakfast, the disclosed system may calculate a nutritional health score for the breakfast foods, but may also determine what nutrients would need to be consumed over the remainder of the day for the individual to consume nutrients in the optimal ranges for all tracked nutrients that day. In this embodiment, the system uses these calculated nutrient amounts to determine combinations of food that can be consumed throughout the remainder of the day to ensure that the individual's nutritional goals are achieved as fully as possible while still consuming a number of calories within that individual's optimal caloric intake range. Thus, the system disclosed herein can operate not only as a tracking system, but also as a recommendation engine to recommend consumables to help individuals reach their nutritional goals.

Referring now to FIG. 1, a block diagram is illustrated showing an example of the electrical systems of a host device 100 usable to implement at least portions of the computerized nutritional health score and recommendation system disclosed herein. In one embodiment, the device 100 illustrated in FIG. 1 corresponds to one or more servers and/or other computing devices that provide some or all of the following functions: (a) enabling access to the disclosed system by remote users of the system; (b) serving web page(s) that enable remote users to interface with the disclosed system; (c) storing and/or calculating underlying data, such as recommended caloric intake ranges, recommended nutrient consumption ranges, and nutrient content of foods, needed to implement the disclosed system; (d) calculating and displaying component or aggregate nutritional health scores; and/or (e) making recommendations of foods or other consumables that can be consumed to help individuals reach optimal nutritional health scores.

In the example architecture illustrated in FIG. 1, the device 100 includes a main unit 104 which preferably includes one or more processors 106 electrically coupled by an address/data bus 113 to one or more memory devices 108, other computer circuitry 110, and/or one or more interface circuits 112. The one or more processors 106 may be any suitable processor, such as a microprocessor from the INTEL PENTIUM® or INTEL CELERON® family of microprocessors. PENTIUM® and CELERON® are trademarks registered to Intel Corporation and refer to commercially available microprocessors. It should be appreciated that in other embodiments, other commercially-available or specially-designed microprocessors may be used as processor 106. In one embodiment, processor 106 is a system on a chip ("SOC") designed specifically for use in the disclosed system.

In one embodiment, device 100 further includes memory 108. Memory 108 preferably includes volatile memory and non-volatile memory. Preferably, the memory 108 stores one or more software programs that interact with the hardware of the host device 100 and with the other devices in the system as described below. In addition or alternatively, the programs stored in memory 108 may interact with one or more client devices such as client device 102 (discussed in detail below) to provide those devices with access to media content stored on the device 100. The programs stored in memory 108 may be executed by the processor 106 in any suitable manner.

The interface circuit(s) 112 may be implemented using any suitable interface standard, such as an Ethernet interface and/or a Universal Serial Bus (USB) interface. One or more input devices 114 may be connected to the interface circuit 112 for entering data and commands into the main unit 104. For example, the input device 114 may be a keyboard, mouse, touch screen, track pad, track ball, isopoint, and/or a voice recognition system. In one embodiment, wherein the device 100 is designed to be operated or interacted with only via remote devices, the device 100 may not include input devices 114. In other embodiments, input devices 114 include one or more storage devices, such as one or more flash drives, hard disk drives, solid state drives, cloud storage, or other storage devices or solutions, which provide data input to the host device 100.

One or more storage devices 118 may also be connected to the main unit 104 via the interface circuit 112. For example, a hard drive, CD drive, DVD drive, flash drive, and/or other storage devices may be connected to the main unit 104. The storage devices 118 may store any type of data used by the device 100, including data regarding preferred nutrient ranges, data regarding nutrient contents of various food items, data regarding users of the system, data regarding previously-generated nutritional health scores, data representing weighting values for calculating nutritional health scores, sensitivity values for calculating nutritional health scores, and any other appropriate data needed to implement the disclosed system, as indicated by block 150. Alternatively or in addition, storage devices 118 may be implemented as cloud-based storage, such that access to the storage 118 occurs via an internet or other network connectivity circuit such as an Ethernet circuit 112.

One or more displays 120, and/or printers, speakers, or other output devices 119 may also be connected to the main unit 104 via the interface circuit 112. The display 120 may be a liquid crystal display (LCD), a suitable projector, or any other suitable type of display. The display 120 generates visual representations of various data and functions of the host device 100 during operation of the host device 100. For example, the display 120 may be used to display information about the database of preferred nutrient ranges, a database of nutrient contents of various food items, a database of users of the system, a database of previously-generated nutritional health scores, and/or databases to enable an administrator at the device 100 to interact with the other databases described above.

In the illustrated embodiment, the users of the computerized nutritional health score and recommendation system interact with the device 100 using a suitable client device, such as client device 102. The client device 102 in various embodiments is any device that can access content provided or served by the host device 100. For example, the client device 102 may be any device that can run a suitable web browser to access a web-based interface to the host device 100. Alternatively or in addition, one or more applications or portions of applications that provide some of the functionality described herein may operate on the client device 102, in which case the client device 102 is required to interface with the host device 100 merely to access data stored in the host device 100, such as data regarding healthy nutrient ranges or nutrient content of various food items.

In one embodiment, this connection of devices (i.e., the device 100 and the client device 102) is facilitated by a network connection over the Internet and/or other networks, illustrated in FIG. 1 by cloud 116. The network connection may be any suitable network connection, such as an Ethernet connection, a digital subscriber line (DSL), a WiFi connection, a cellular data network connection, a telephone line-based connection, a connection over coaxial cable, or another suitable network connection.

In one embodiment, host device 100 is a device that provides cloud-based services, such as cloud-based authentication and access control, storage, streaming, and feedback provision. In this embodiment, the specific hardware details of host device 100 are not important to the implementer of the disclosed system-instead, in such an embodiment, the implementer of the disclosed system utilizes one or more Application Programmer Interfaces (APIs) to interact with host device 100 in a convenient way, such as to enter information about the user's demographics to help determine healthy nutritional ranges, to enter information about consumed foods, and other interactions described in more detail below.

Access to device 100 and/or client device 102 may be controlled by appropriate security software or security measures. An individual user's access can be defined by the device 100 and limited to certain data and/or actions, such as inputting consumed food or viewing calculated scores, according to the individual's identity. Other users of either host device 100 or client device 102 may be allowed to alter other data, such as weighting, sensitivity, or healthy range values, depending on those users' identities. Accordingly, users of the system may be required to register with the device 100 before accessing the content provided by the disclosed system.

In a preferred embodiment, each client device 102 has a similar structural or architectural makeup to that described above with respect to the device 100. That is, each client device 102 in one embodiment includes a display device, at least one input device, at least one memory device, at least one storage device, at least one processor, and at least one network interface device. It should be appreciated that by including such components, which are common to well-known desktop, laptop, or mobile computer systems (including smart phones, tablet computers, and the like), client device 102 facilitates interaction among and between each other by users of the respective systems.

In various embodiments, devices 100 and/or 102 as illustrated in FIG. 1 may in fact be implemented as a plurality of different devices. For example, the device 100 may in actuality be implemented as a plurality of server devices operating together to implement the media content access system described herein. In various embodiments, one or more additional devices, not shown in FIG. 1, interact with the device 100 to enable or facilitate access to the system disclosed herein. For example, in one embodiment the host device 100 communicates via network 116 with one or more public, private, or proprietary repositories of information, such as public, private, or proprietary repositories of nutritional information, nutrient content information, healthy range information, environmental impact information, or the like.

In one embodiment, the disclosed system does not include a client device 102. In this embodiment, the functionality described herein is provided on host device 100, and the user of the system interacts directly with host device 100 using input devices 114, display device 120, and output devices 119. In this embodiment, the host device 100 provides some or all of the functionality described herein as being user-facing functionality.

As noted above, the system disclosed herein is premised, in various embodiments, on the idea of promoting nutritional health. The notion of nutritional health is built on the idea that all nutrients have healthy ranges for consumption. That is, the notion of nutritional health is built on the idea that there are no intrinsically good nutrients, and no intrinsically bad nutrients. Instead, for any possible nutrient, consumption of that nutrient can be either inside of a healthy range or outside of a healthy range. While the healthy range can vary for different individuals, consumption of a nutrient inside the healthy range is generally viewed as being healthy consumption of that nutrient.

With this understanding in mind, the disclosed system relies on a definition of nutritional health in which an individual is nutritionally healthy if the nutrients (either micro or macro) consumed by the individual are within the healthy ranges for those nutrients, which ranges are specific to the individual, over a specified period of time. By ascertaining and relying on the nutritional needs of an individual or group of individuals the system disclosed herein provides a personalized nutrition tracking and management system that enables individuals to optimize their nutritional intake. The disclosed system enables individuals to make actionable decisions based on nutritional scoring, and allows them flexibility in food consumption based on their individual nutrient requirements.

In various embodiments, the system disclosed herein is arranged as a plurality of modules, wherein each module performs a particular function or set of functions. The modules in these embodiments could be software modules executed by a general purpose processor, software modules executed by a special purpose processor, firmware modules executing on an appropriate, special-purpose hardware device, or hardware modules (such as application specific integrated circuits ("ASICs")) that perform the functions recited herein entirely with circuitry. In embodiments where specialized hardware is used to perform some or all of the functionality described herein, the disclosed system may use one or more registers or other data input pins to control settings or adjust the functionality of such specialized hardware. For example, a hardware module may be used that is programmed to analyze nutrient health scores based on a piecewise continuous function that is increasing in a first segment, flat in a second segment, and decreasing in a third segment. In this example, the hardware may be programmed to evaluate the function, and one or more inputs to the hardware may be configured to receive inputs of, for example, the input value at which the first segment meets the second segment, the input value at which the second segment meets the third segment, and parameters to indicate the rate at which the third segment is decreasing (e.g., a slope or a function defining the shape of the third segment). In still other embodiments, where the modules to perform various functionality described herein are software modules executable by hardware, the modules may take the form of apps or subsets of apps that may be designed to run on a processor executing a particular, predefined operating system environment.

Figure 2:
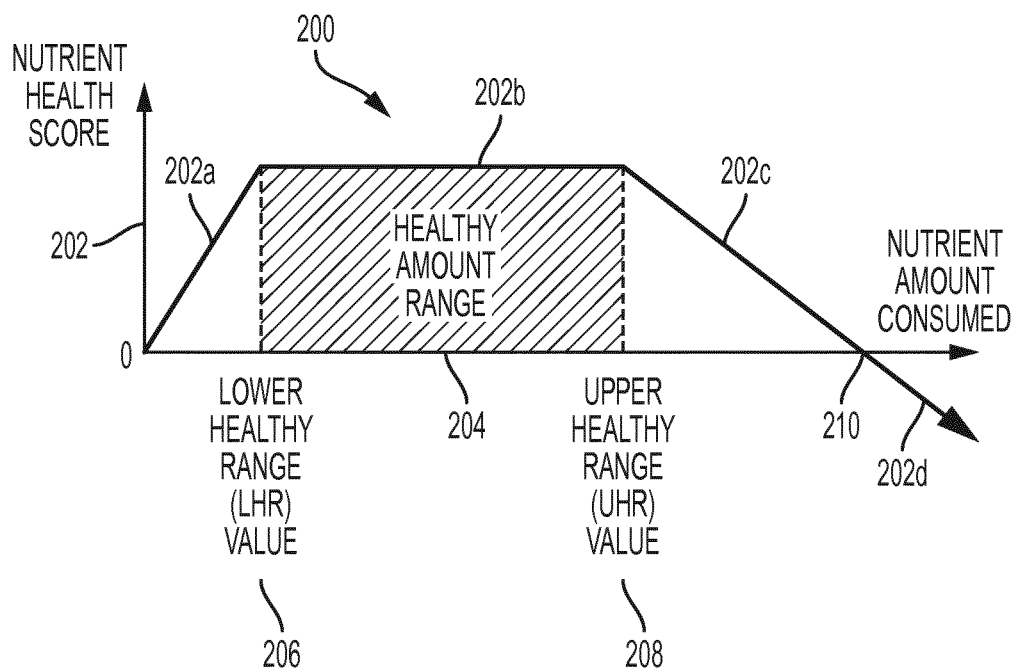
FIGS. 2 and 3 are each a schematic illustration of a generic curve representing the nutrient health scores for a particular nutrient as defined here.

FIG. 2 illustrates an example curve 200 that evidences in more detail the concept of healthy ranges of nutrient consumption. The curve 200 of FIG. 2 relates to a particular nutrient; a food item may include many nutrients, and thus may have many curves like curve 200 that are applicable to it. In the illustrated embodiment, the vertical axis 202 relates to the nutrient health score (discussed in detail below), while the horizontal axis 204 relates to the amount of a nutrient consumed.

Referring still to curve 200, it can be seen that if none of the nutrient represented by the curve is consumed (i.e., at the origin of the chart), the nutrient health score is 0. This means that consumption of the particular nutrient does not impact overall nutritional health in any way. As consumption of the nutrient increases from the origin point (i.e., as more of the nutrient is consumed), the nutritional health score increases as illustrated at curve portion 202a, representing an increasing benefit obtained by the consumption of the nutrient represented by the curve.

At a certain point 206, referred to in the chart of FIG. 2 as the Lower Healthy Range (LHR) value, the benefits of ingesting additional amounts of the nutrient stop increasing, as illustrated at curve portion 202b. The flat shape of the curve between point 206 and point 208, identified as the Upper Healthy Range (UHR) value in FIG. 2, indicates that the nutrient health score is not increasing as additional nutrient is being consumed, and thus no further benefit is being derived. It should be appreciated that while no additional benefit is being derived in this portion of the chart, additional calories are nonetheless being consumed.

At the Upper Healthy Range (UHR) value 208, additional consumption of a particular nutrient actually begins to have a diminishing positive impact on the nutritional health of a user. That is, further consumption of the nutrient, while not harmful, begins to become less helpful than consumption of the amount of the nutrient in the range corresponding to the flat portion of the curve 202b. The downward sloping portion of curve 202c, which is still above the horizontal axis (and thus still associated with a positive nutrient health score), indicates these diminishing returns in the form of a nutrient health score that is positive but decreasing as additional nutrient is consumed.

Eventually, as illustrated by portion 202d of the curve 200, enough of the nutrient is consumed that consumption is not just resulting in a diminishing return, but may actually be harmful to the individual. The point at which curve 200 crosses the horizontal axis, which is illustrated as point 210, illustrates that further consumption beyond the amount of nutrient at point 210 harmful to the individual. As described below, an overall nutritional health score is calculated in various embodiments by multiplying each component nutrient health score by a weighting value and summing the results; in the event the amount of a nutrient consumed corresponds to the portion 202$d$ of FIG. 2, the component part of the nutritional health score for that nutrient is actually a negative value.

In various embodiments, defining portion 202$d$ of curve 200 in such a way that the nutrient health score is negative reflects the fact that individuals are limited by the negative impacts of consuming none of something. In other words, the nutrient health score of consuming none of a nutrient is zero for that nutrient. However, to reflect the idea that there is not a limit to the harm that can be done by over-consuming a particular consumable, section 202$d$ of curve 200 has a negative value that continues to become a larger negative number as an individual consumes more and more of a nutrient.

It should be appreciated that existing nutritional tracking schemes do not take into account the impact of consuming nutrients in amounts more than the Upper Healthy Range (UHR) value. Thus, consumption of nutrients only had the ability, in known systems, to improve or increase nutritional scores, and never to decrease those scores. Since diminishing positive impacts on the score, and eventual negative impacts on the score, were not possible in known systems, these known systems did not fully account for the nutrients ingested by an individual. Accordingly, taking into account consumption of nutrients at the points of curve 200 labeled as 202$c$ and 202$d$ is a substantial advantage of the instant application.

It should be further appreciated that in one embodiment, the maximum nutrient health score provided for each nutrient tracked by the disclosed system has the same value, such as a value of 1, and that this maximum value corresponds to the horizontal portion of the curve wherein nutrient consumption is in the healthy amount range. Thus, when an individual is consuming an amount of a nutrient in the healthy amount range, the nutrient health score for that consumption is 1. By providing for the same maximum for each nutrient, the relative importance of the various nutrients can be reflected in the overall nutritional health score by applying weighting values to the various tracked nutrients as described in more detail below.

In various embodiments, the disclosed system stores an indication of a curve like curve 200 for each nutrient that it factors into an overall nutritional health score. In one embodiment, discussed in more detail below, the system stores an indication of the curve by storing a lower healthy range value, an upper healthy range value, a weighting value, and a sensitivity value for each individual or population of individuals to whom the nutritional health score is tailored. This embodiment is discussed in more detail below.

In other embodiments, the system stores indications of the information necessary to define curves like curve 200 for each nutrient by storing three values for each nutrient: a Lower Healthy Range (LHR) value, an Upper Healthy Range (UHR) value, and a value indicating a point where the curve 200 crosses the horizontal axis above the UHR value. In one embodiment, these values are stored as absolutes and are scaled as appropriate based on varying caloric intake values. In one embodiment, these values are stored as amounts of nutrient consumption per amount of calories. In one embodiment, the disclosed system stores the third value (i.e., the value regarding where the curve crosses the horizontal axis) as a slope and therefore calculates the value based on the stored UHR.

The disclosed system in various embodiments stores nutrient range consumption values that are as personalized as possible to individual people. The Institute of Medicine publishes recommendations of population-level daily reference intake (DRI) values for certain nutrients for populations based on gender and age. For example, the Institute of Medicine may specify a handful of recommended nutrient values for infants 0 to 6 months, infants 6 to 12 months, children 1-3 years, children 4-8 years, males 9-13 years, females 9-13 years, and so on. However, these specified values are insufficient for analyzing the overall nutritional health of an individual because they are not actually tailored to individuals. Specifically, they do not take into account a person's health level (e.g., whether the person is athletic or active), health conditions (e.g., obesity, diabetes, allergies), medical limitations (e.g., whether the person is a critical care patient), physiology (height and weight), or any other individual specific consideration. Instead, known recommended intake values are based on age and gender (for certain ages). The system disclosed herein provides a further advantage in that it allows for individuals to have their own, personal, healthy ranges for each nutrient depending on the particular situation for that individual. In further embodiments, individuals may have their own arrangement of weighting values and/or sensitivity values tailored to their own personal health conditions. With these personalized ranges and/or weighting/sensitivity values, the disclosed system can calculate a completely personalized nutritional health score. Indeed, for some individuals, a certain nutrient may not be needed at all, or there may be no negative impact of consuming additional amounts of a nutrient beyond a lower healthy amount of the nutrient. By defining the healthy range of a particular nutrient, the disclosed system can account for that lack of need of the nutrient in a way known systems simply cannot.

The curve 200 of FIG. 2 pertains to the healthy range of consumption of a single nutrient, such as calcium. It should be appreciated that a similar curve (albeit with different slopes and points of intersection with the horizontal axis) can be defined for each nutrient whose consumption is tracked by the disclosed system. In even more general terms, in various embodiments a curve like curve 200 is defined for each characteristic of a consumable that can be tracked. Thus, a curve like curve 200 can be defined for the energy intake of a user. In this case, a lower energy intake value and an upper energy intake value (e.g., in kcal) define an energy intake range for an individual over a given time period (such as over a given day). In addition, a weighting parameter and sensitivity parameter can be defined for energy intake for a particular person. The weighting parameter defines the impact of the individual energy health score on the overall nutritional health score, and the sensitivity parameter defines a particular individual's sensitivity to over-consuming calories. By defining these four values for energy intake, the system can be customized to a particular person. For example, if the system is being customized to a relatively athletic person, the weight value might be defined relatively high since caloric intake is important to the user's overall health, and the sensitivity parameter might also be defined relatively high since over-consumption of calories would not have a strong impact on the individual's overall health. These values may be adjusted, for example, when applied to an individual interested in losing weight such that the weighting parameter is still high (caloric intake is still important to overall nutritional health scores) but the sensitivity value is low (over-consumption of calories should have a large impact on the overall score).

In one embodiment, the disclosed system also stores curves like curve 200 for other trackable characteristics of food consumption, such as financial cost, $CO_2$ emissions associated with creating the food, and the like.

Figure 3:
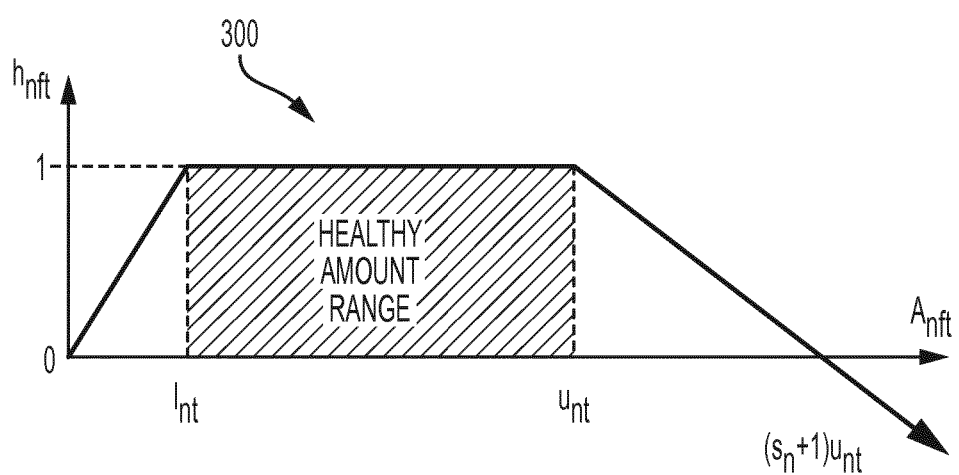

Referring now to FIG. 3, a more specific curve 300 (including more specific labeling of points on the curve) is illustrated for a particular nutrient. FIG. 3 is similar to FIG. 2 in that it illustrates the increasing returns of consuming a nutrient under a lower healthy range value, labeled in FIG. 3 as $l_{nt}$. FIG. 3, like FIG. 2, also illustrates the decreasing returns of consuming a nutrient above an upper healthy range value, labeled in FIG. 3 as $u_{nt}$. Finally, FIG. 3 illustrates the eventual negative returns of consuming a nutrient n.

In FIG. 3, the vertical axis is labeled $h_{nft}$, which is used to denote the nutrient health score for a nutrient "n" in units of food "f" per unit of time "t". Thus, the nutrient health score $h_{nft}$ could, for example, be an expression of a score for ingestion of vitamin A per food per day. FIG. 3 illustrates that the nutrient health value $h_{nft}$ has a maximum value of 1 when the amount of nutrient "n" being consumed is in the Healthy Amount Range. In FIG. 3, the horizontal axis is labeled $A_{nft}$, which is used to denote the amount of a nutrient "n" consumed in units of food "f" per unit of time "t". Thus, the amount $A_{nft}$ could, for example, be an expression of an amount of vitamin A per food per day.

In the embodiment illustrated in FIG. 3, the lower healthy range of is labeled as $l_{nt}$ and the upper healthy range is labeled as $u_{nt}$. These values each include the subscript "n" to indicate that the illustrated amounts are particular to nutrient "n", and the value "t" to indicate that the lower and upper healthy range is defined in terms of amount of nutrient "n" per time "t". Thus, the values $l_{nt}$ and $u_{nt}$ could define the range of healthy vitamin A consumption in a day.

FIG. 3 also illustrates a value at the point where curve 300 crosses the $A_{nft}$ axis labeled as $(s_n+1)u_{nt}$. In this embodiment, $s_n$ represents a so-called sensitivity parameter. In general, the sensitivity parameter is a representation of the severity or the extent of the impact of consuming too much of a particular nutrient. In the illustrated embodiment, the sensitivity parameter is added to one and multiplied by the $u_{nt}$ value to determine the point where additional consumption of a nutrient begins to have a negative impact on an individual. Accordingly, the larger the sensitivity parameter, the larger the product of the $u_{nt}$ value and $(s_n+1)$, and the more of nutrient "n" that needs to be consumed before it crosses the zero-axis and begins to become harmful to an individual. In one embodiment, the sensitivity value is a value greater than zero and less than 2, such that the point where the curve 300 crosses the $A_{nft}$ axis is at least 100% larger than $u_{nt}$ and at most 300% of $u_{nt}$. Put another way, in the embodiment illustrated in FIG. 3, if the sensitivity parameter $s_n$ is 1, the nutrient health score will go to zero if the amount consumed is 100% over the $u_{nt}$ value. Similarly, if the sensitivity parameter $s_n$ is 0.5, the nutrient health score will go to zero if the amount consumed is 50% over the $u_{nt}$ value. In this embodiment, the higher the sensitivity score, the less the score is affected by the amount; the score is inversely proportional to the sensitivity value.

In one embodiment, such as the embodiment described above, the disclosed system stores a sensitivity value in association with each nutrient tracked by the system. For example, the system may store a data structure or other database of nutrient information containing a "sensitivity" value for each nutrient. One example representation of such a data structure is illustrated in FIG. 4, where the first column 401 illustrates the name of the nutrient and the third column 403 illustrates the sensitivity value for the nutrient. It should be appreciated that in the table 400 of FIG. 4, the sensitivity for calcium is "2," while the sensitivity for saturated fat is "1." This indicates that more extra calcium (above the $u_{nt}$ value for calcium) is needed for the calcium to begin to have a negative impact on the individual's nutritional health (reducing the overall nutritional health score) than extra saturated fat. Put another way, it is less unhealthy for an individual to consume extra calcium than it is for an individual to consume extra saturated fat.

In other embodiments, the sensitivity value $s_n$ may be defined in any other suitable way, such as by being a number greater than 0 and less than 3, where the value at which the curve 300 crosses the An axis is simply calculated by multiplying $u_{nt}$ by $s_n$. In this embodiment, whereby the curve 300 could cross the $A_{nft}$ axis sooner than 100% of $u_{nt}$ past the $u_{nt}$ value. In other embodiments, $s_n$ could be stored as a slope, a value to be added to $u_{nt}$, a value to be scaled by recommended caloric intake and added to $u_{nt}$, a value to be scaled by recommended caloric intake, or any other suitable value for defining the point beyond the healthy range at which additional consumption of a nutrient becomes harmful. In one embodiment, for some nutrients, no $s_n$ value exists, meaning that additional consumption of a nutrient is not harmful and merely adds calories without adverse effect tied to the nutrient consumption. In another embodiment, for some nutrients, the system either assigns an infinite $s_n$ value or defines an infinite upper healthy range value to achieve the same outcome—namely, to indicate that overconsumption of a particular nutrient is not harmful.

It should be appreciated that in various embodiments, the negative score resulting from over consumption of a nutrient may potentially go to an infinitely negative value. Accordingly, in various embodiments of the disclosed system, a floor may be defined to prevent over-consumption of nutrients with a relatively low sensitivity score (i.e., a score that defines a relatively steeply sloped portion 202c and 202d of curve 200 of FIG. 2) to ensure that overall nutritional health scores are not unduly skewed by over consumption situations.

In one embodiment, the system disclosed herein stores indications of various groups of nutrients based on similar sensitivity scores of those nutrients. For example, in an embodiment, the sensitivity score for a first group of vitamins comprising Vitamin B1, Vitamin B2, Vitamin B12, Biotin, Pantothenic Acid, Vitamin K, and Potassium is chosen such that the zero-crossing point is 800% of the upper healthy limit. In this embodiment, the sensitivity score for a second group of vitamins comprising Vitamin B6, Vitamin C, Vitamin D, Vitamin E, Folate, Niacin, Phosphorous, Selenium, and Magnesium is chosen such that the zero-crossing point is 400% of the upper healthy limit. In this embodiment, the sensitivity score for a third group of vitamins comprising Vitamin A, Calcium, Iodine, Iron, Zinc, Copper, and Manganese is chosen such that the zero-crossing point is 200% of the upper healthy limit. In this embodiment, the relative zero-crossing points indicate that there is relatively low evidence of risk to health for exceeding the upper healthy limit of nutrients in the first group, low risk to health for exceeding the upper healthy limit of nutrients in the second group, and potential health risk for exceeding the upper healthy limit of nutrients in the third group.

The disclosed system in various embodiments calculates a nutrient health score for each nutrient consumed over a given time for a particular food. In these embodiments modules of the disclosed system calculate these values by determining the amount of the nutrient consumed, and determining height or value of the function defining the curve, such as curve 200 of FIG. 2 or curve 300 of FIG. 3, for the given amount of that particular nutrient consumed per unit of time. In this way, for a particular food consumed in a particular time, the disclosed system determines and stores a plurality of nutrient health values for the nutrients in the food. In one embodiment, the disclosed system stores this information in a specially designed data structure for aggregating nutrient health scores for a particular consumable item. In one embodiment, the system also displays some or all of the nutrient health values to a user of the system, as described in more detail below.

Referring again to FIG. 3, the nutrient health score for a particular nutrient can be calculated according to the following function, referred to herein as Equation 1:

$$h_{nft} = \begin{cases} \dfrac{A_{nft}}{l_{ct}} & \text{if } A_{nft} \leq l_{nt} \\ \dfrac{(s_n + 1)u_{nt} - A_{nft}}{s_n u_{nt}} & \text{if } A_{nft} \geq u_{nt} \\ 1 & \text{otherwise} \end{cases}$$

The function defined by Equation 1 may be referred to as a piecewise continuous function or as a stepwise continuous function. In some embodiments, the function has a defined value for each amount of food consumed, but the derivative (slope) of the function is not a continuous function. In some embodiments, there are no large, instantaneous changes in the value, even if the slope of the function changes instantaneously.

In Equation 1 above, the variable f refers to food (where food could be a single food or a set of foods consumed in arbitrary caloric consumption amounts). The variable n generally refers to a nutrient, such as a vitamin A, saturated fat, or calcium. The variable t generally refers to a time period to be used for a value's quantification. The variable $l_{nt}$ refers to a lower healthy range for nutrient n per time t, and the value $u_{nt}$ refers to an upper healthy range for a nutrient n per time t.

Throughout this disclosure, the variable "n" is used to refer to aspects of a particular nutrient when calculating a nutrient health score for that nutrient. While in some embodiments the disclosed system is configured to calculate nutrient health scores only for nutrients, the instant disclosure contemplates a broader applicability. For example, the discussion herein of determining scores for nutrient consumption could be broadened to include determining scores for any other measurable feature of a consumable, such as impact on the environment to produce the consumable, cost to obtain the consumable, difficulty to obtain the consumable, and shelf-life of the consumable. Depending on the measurable trait, the lower and/or upper range values may be zero or infinity. For example, if cost is a measured and tracked characteristic of a food, the lower range value may be 0 to indicate that purchasing food that costs as little as possible is "optimal." In this embodiment, the upper range value may also be zero, with decreasing scores for any amount greater than zero, indicating that for some consumers, low cost is paramount. The system herein also enables the impact of the financial cost on the overall score to vary by adjusting weight and sensitivity values such that more wealthy individuals may be less sensitive to higher priced foods. By applying Equation 1 to other measurable aspects of consumables, the disclosed system enables the calculation of a score that, for example, provides a diet optimized not only for nutrient consumption but for financial cost to obtain the component foods of the diet or for impact on the environment.

With regard to calculating the amounts of nutrient in foods, the instant disclosure focuses on a system that is based on the consumption of a certain number of calories in a certain time period, such as in a certain day. In other words, all nutrient and nutritional health scores calculated by the disclosed system are calculated for a given caloric intake level over a given amount of time. To reflect this, the variable $A_{nft}$ refers to the amount of nutrient n in food f per time t.

$A_{nft}$ is calculated by multiplying $\delta_{nf}$ by $e_{ft}$, where $e_{ft}$ is the amount of energy (e.g., kcal) consumed of a particular food f per time t. For example, if the food f is ground beef, $e_{ft}$ may be used to represent the number of calories of ground beef consumed in a given day. The variable $\delta_{nf}$ represents the nutrient density of a nutrient n in a food f, and can be calculated by dividing the amount of a nutrient n in a "portion" of a food f (sometimes represented as $a_{nf}$) by the energy (e.g., kcal) in a single "portion" of food f (sometimes represented as $k_f$). Using this division operation, the "portion" in the numerator cancels with the "portion" in the denominator, with the result being a nutrient density that, when multiplied by the energy of a particular food consumed, results in the amount of nutrient n in a food f per time t.

In the embodiment described above, the system calculates $A_{NFT}$ by multiplying energy by nutrient density. In one embodiment, the system calculates $A_{NFT}$ by multiplying the amount (e.g., in grams) of a food consumed by a stored value indicating nutrients per amount (e.g., nutrients per gram) for the food. For the various tracked consumables, calories are determined in a similar way: the amount of food consumed is multiplied by a stored ratio of calories to amount.

In some embodiments, the disclosed system relies on standards bodies' published nutrient content information as the basis for its stored nutrients per amount value discussed above. For example, in one embodiment the system stores data from the USDA indicating the amount of nutrients and calories in certain amounts of certain foods.

In various embodiments, the disclosed system includes a database of values needed to perform some of the calculations and required to solve Equation 1 above. For example, in an embodiment the disclosed system stores a database or other data store of food-related information for a plurality of types of food. This food-related information may include information about ingredients, foods, meals, or diets, and may include information about items selected from restaurant menus (e.g., a hamburger from a particular fast food chain) or information about commercially available products (e.g., a particular brand of soft drink). In these embodiments, the food-related information needed to solve Equation 1 includes the following:

A listing of foods f;
A listing of nutrients n;
A listing of amounts of nutrients n in a single, standardized, portion of food f, denoted herein as $a_{nf}$; and
A listing of amounts of energy in a single, standardized portion of food f, denoted herein as $k_f$;

In some embodiments, certain values (e.g., time period t and energy consumed of food f in time period t, denoted as $e_{ft}$) are alterable by the user and are thus provided by the user depending on the user's use of the system as described in more detail below. For example, the user in various embodiments specifies the amount of time for which the score is being calculated (e.g., in terms of a fraction of a number of days, such as 0.33 of a day for a single meal) and the amount of food consumed in that amount of time. From the entered amount, the system can determine the amount of energy (i.e., calories) of food consumed as well as the amount of nutrients consumed via that food.

In some embodiments, certain values that can be calculated from the values listed above, such as nutrient density of nutrient n in food f (denoted $\delta_{nf}$), are calculated as needed by the disclosed system based on stored information. In other embodiments, these values are stored in a database or data store in association with the various foods and/or nutrients to which they correspond rather than being calculated on-the-fly.

In various embodiments, the stored, user-entered, and calculated values indicated above enable the calculation of the value of $A_{nft}$ as described above, which value is needed to calculate the nutrient health score of Equation 1. According to Equation 1, if $A_{nft}$ is less than $I_{nt}$, the score is calculated to be the amount of nutrient consumed divided by the lower healthy range value, which is a point on the upward sloping line corresponding to segment 202a. If $A_{nft}$ is between than $I_{nt}$ and $u_{nt}$ (i.e., the consumed amount of nutrient "n" is in the healthy range), the score is 1. Finally, if $A_{nft}$ is greater than $u_{nt}$, the score is positive if the amount of nutrient consumed is less than the zero-crossing point as defined by sensitivity score $s_n$, and is negative if the amount of nutrient consumed is greater than the zero-crossing point as defined by sensitivity score $s_n$.

In the illustrated embodiment, it should be appreciated that all segments of the nutrient health score curve 200 or 300 are presumed to be linear. In some embodiments, one or more of the curve segments may not be linear. For example, non-linear curves such as exponential curves, Gaussian curves, and curves defined by other non-linear functions may be used to define either the behavior of the curve at nutrient consumption amounts smaller than the lower healthy range value or at nutrient consumption amounts larger than the upper healthy range value. It should be appreciated that functions defining the curves indicative of nutrient health score where $A_{nft}$ is less than $I_{nt}$ or where $A_{nft}$ is greater than $u_{nt}$ in the equation above is possible according to the disclosed system; linear segments were chosen for description here because of the ease of explanation and comprehension. In such alternative embodiments, where non-linear functions describe portions of the curve defining the nutrient health score, sensitivity values nonetheless can be used to describe or to enable appropriate modules to calculate the zero-crossing point where over-consumption causes the nutrient health score for that nutrient to have a value less than the value ascribed to a consumption of none of the particular nutrient.

Having stored the nutrient health scores for a plurality of nutrients in a given consumable as described above, the disclosed system in a next step aggregates these nutrient health scores into an overall nutritional health score for the consumable, designated here as $H_{ft}$. In one embodiment, the system performs this aggregation according to the following equation, referred to herein as Equation 2:

$$H_{ft} = \Sigma_{\forall n} w_n h_{nft}$$

In Equation 2, $h_{nft}$ represents the nutrient health score for a particular nutrient n, $w_n$ represents a weight value for a particular nutrient n, and the summation is performed over all nutrients tracked in the system. In this embodiment, if a particular consumable does not include a particular nutrient tracked in the system, the nutrient health score for that nutrient is zero and the nutrient does not increase or decrease the overall nutritional health score $H_{ft}$. Because $H_{ft}$ is an overall nutritional health score, it is non-specific to any particular nutrient. Accordingly, $H_{ft}$ is expressed for the consumption of a particular food f in a particular time t.

One of the substantial advantages provided by embodiments of the system disclosed herein is that the nutrient health scores (and thus the nutritional health scores) are calculated as a function of time. That is, a user can specify a caloric intake range for a designated period of time, and can specify an amount of time over which a particular food is consumed. The score assigned to that food based on its component nutrients is thus a function of time. Known schemes are not believed to have provided for scoring consumables as a function of time. This aspect of the instant disclosure is a substantial advantage over known systems because time can be used to determine what foods to consume to meet nutritional goals over the remainder of a period, such as over the remainder of a day. For example, if a user of the disclosed system goes out to dinner one night of a weekend, the user of the system can plan the remainder of his or her weekend diet around the foods consumed at dinner and thus still meet his or her nutritional goals despite having eaten a meal that, on its own, may not have been considered "healthy" under other known systems. As discussed below, various user interfaces disclosed herein provide the user with the ability to enter an indication of the time over which the food has been or will be consumed, such as by indicating a number of days or portions of days.

In various embodiments, the disclosed system stores a plurality of weight values, denoted as "w," for each nutrient that factors into the nutritional health score H. The weight value for a particular nutrient "n" is designated $w_n$, and indicates the impact that the nutrient health score for nutrient "n" has on the overall nutritional health score. In general, the larger the weight value for a particular nutrient, the bigger the impact the nutrient has on the nutritional health score.

In various embodiments, the disclosed system stores a plurality of weighting values in a table such as the table 400 illustrated in FIG. 4. In the table 400 of FIG. 4, column 402 includes a weight associated with each of the 26 nutrients having entries in columns 401. The relative weights for the various nutrients indicate the relative impact of each nutrient on the overall nutritional health score calculated according to the above equation. In the illustrated embodiment of FIG. 4, summing the weights results in a total of 1. Accordingly, the maximum nutritional health score that could be achieved using the weights of table 400 of FIG. 4 would be 1; this score is achieved if the nutrient health score for each nutrient of table 400 of FIG. 4 was 1. In some embodiments, it may be helpful to provide a nutritional health score H on a scale of 1 to 100; in these embodiments, such a result can be achieved by either multiplying each weight by 100 or by multiplying the overall nutritional health score calculated according to the above equation by 100.

In general, the larger the weight value for a nutrient, the larger an impact that nutrient will have on the overall nutritional health score. This holds true for under/over consumption as well as healthy consumption. In other words, if a nutrient is being under or over consumed, larger weight values will lower the nutritional health score to a larger extent than smaller weight values. Likewise, if a nutrient is being consumed in a healthy amount, larger weight values will increase the nutritional health score to a larger extent than smaller weight values.

For example, if a nutrient such as "sugar" is given a relatively high scoring weight comparative to vitamins, a food that is low in sugar will in general receive a high nutritional health score. This will be true even if the food is low in other nutrients, as the overall nutritional health score is more dependent on the sugar score. Accordingly, appropriate balancing of weights for different nutrients when personalizing the disclosed system to an individual is of substantial importance.

As noted above, in one embodiment four parameters must be defined for each nutrient being score: Lower Healthy Range (LHR) value, Upper Healthy Range (UHR) value, scoring sensitivity (i.e., upper zero-crossing), and scoring weight (relative amount of contribution of nutrient to overall score). In one embodiment, these parameters are stored as two separate files, databases, or data structures in the storage devices or other storage solutions relied on in the disclosed system.

In one embodiment, a first file stores weight and sensitivity values for each of a plurality of tracked nutrients. FIG. 4, discussed above, is an example representation of the table contained in such a file. As can be seen from FIG. 4, for each of a plurality of nutrients tracked by the disclosed system, a weight value and a sensitivity value are stored in columns 402 and 403, respectively. As discussed above, the weight value indicates the relative importance or impact of the nutrient health score for a particular nutrient on the overall nutritional health score, while the sensitivity value indicates the impact of consuming additional nutrients beyond the UHR on the nutrient health score (and thus the overall nutritional health score).

In one embodiment, a second file stores LHR and UHR values for each of the nutrients tracked by the system. In this embodiment, LHR and UHR values are stored for each of a plurality of different people or profiles of people. Thus, for example, the LHR/UHR file may store a plurality of LHR/UHR pairs for each of a plurality of nutrients, where one pair applies to a 18-20 year old male athlete weighing between 180 and 220 pounds, one pair applies to a 20-25 year old male diabetic weighing between 250 and 300 pounds, one pair applies to a 45-50 year old female intensive care patient weighing between 100 and 125 pounds, and so on. In further embodiments, where nutrient ranges are personalized on an individual basis, the disclosed system stores a pair of LHR and UHR values for each nutrient for a particular individual, such as person X. In this embodiment, a database or other data store contains a LHR/UHR pair for each nutrient for each individual using or being tracked by the disclosed system.

In a presently preferred embodiment, the disclosed system stores two separate data structures (such as tables) to enable nutrient health scores and nutritional health scores to be calculated. In this embodiment, a first table stores lower healthy range and upper healthy range for each tracked nutrient, and a second table stores weighting parameters and sensitivity parameters for the tracked nutrients. The reason such an arrangement is presently preferred is that it most readily facilitates creation of scoring profiles for individuals, and thus customization of scores to individuals. One way to customize the scores to particular individuals is to adjust the weighting parameters to reflect the importance of different nutrients to a particular person's health, and to adjust the sensitivity parameters to reflect the impact of overconsumption of various nutrients on the particular person's health. Thus, for example, a relatively young athlete may use a table where weighting values emphasize protein and simple carbohydrate intake where overconsumption of sugar is relatively unimportant, whereas a relatively older diabetic person may use a table where sugar is weighted very high because of a high impact on that person's health, and where sensitivity values are chosen to reflect a relatively large impact of overconsumption of sugar. By breaking the stored data into two tables, the appropriate weighting/sensitivity parameters can be chosen while using relatively more standardized lower and upper healthy range values. These sets of weighting/sensitivity parameters are referred to in various embodiments as "scoring profiles," and provide for the ability for an individual to select a scoring profile customized to that individual and to his or her dietary needs and goals.

FIG. 5 illustrates an excerpt 500 from a table of LHR/UHR values that pertain to populations of people based on age. In the excerpt 500, ranges of consumption of various nutrients (identified in the left-most column of the table excerpt) each include a pair of values (illustrated in the table of FIG. 5 as LHR and UHR) for each population group in the table (females 31-50 and females 9-13). Of course, in the full table from which excerpt 500 is taken, each tracked nutrient for which daily reference intakes are stored is listed in the DRI_name column, and several additional pairs of columns will be included to reflect the different personalization in terms of recommended consumption amounts are included to the right of the DRI_name column. In some embodiments, the granularity of the pairs of columns of populations of people is more detailed, such that the table may include several pairs of columns for females aged 31-50 based on weight, activity level, health conditions, weight loss goals, etc.

It should be appreciated that for some nutrients listed in the excerpt 500 of FIG. 5, one or more of the values is listed as "na." In the illustrated embodiment, this means that either there is no health benefit derived from consuming the nutrient (where no lower healthy range value is defined) or that there is no decreasing benefit or detriment to consuming additional amounts of the nutrient (where no upper healthy range value is defined).

The data stored in the table of FIG. 4 and the table of FIG. 5 enables the calculation of the nutrient health scores for each tracked nutrient and the subsequent summation of weighted nutrient health scores to determine the overall nutritional health score, as described above. It should be appreciated that in other embodiments, more than or fewer than two tables may be used. For example, a single table may be used for each of LHR, UHR, weight, and sensitivity. Alternatively, a single table may be used for LHR and UHR, a single table may be used for weight, and a single table may be used for sensitivity. It should be appreciated that the particular data structures used to store the various data needed to calculate nutritional health scores are not critical to the calculation of the nutritional health score so long as the four categories of data (LHR, UHR, weighting parameters, sensitivity parameters) are stored in some form.

In various embodiments, personalization is achieved by providing specific combinations of LHR, UHR, weight, and sensitivity for a particular person. In some such embodiments, as part of building the tables storing this data in the disclosed system, an individual may consult with a nutritionist, answer survey questions, or otherwise provide information about himself or herself to enable the creation of customized healthy ranges, weights, and sensitivities. For example, a person may indicate that he or she is anemic; this may impact healthy range of iron intake, the sensitivity to iron intake, and the weight given to the iron nutrient health score when aggregated into the overall nutritional health score. In some embodiments, the disclosed system enables users to enter certain parameters about themselves, such as age, weight, Body Mass Index (BMI), activity level, and gender. The system uses these parameters to determine which portion of a data structure (such as the particular columns of the table of FIG. 5) to use when determining what that user's healthy ranges are for the various tracked nutrients. In other embodiments, the system uses information entered about the individual to calculate healthy ranges, such as by determining a multiplier and multiplying a baseline set of ranges by the multiplier.

In various embodiments, the data stored in FIG. 5 relating to weighting parameters and sensitivity parameters enable the selection and/or development of scoring profiles for particular individuals or populations of individuals. That is, by specifying different combinations of weighting/sensitivity parameters, such as following discussions with nutritionists or other trained nutrition professionals, the disclosed system enables individuals or populations to create profiles that emphasize important scores to those individuals or populations of users. The use of the phrase "scoring profile" in various embodiments refers to the values that can be stored to customize nutrient health scores and nutritional health scores for particular people.

Much of the discussion above has focused on calculating various scores for a particular food. One of the substantial improvements provided by the system disclosed herein is the ability to calculate nutritional health scores for differing quanta of consumables, such as for a particular ingredient, food, saleable item, meal, or diet. The disclosed system thus advantageously provides the ability to combine varying quantities of food into a single, scoreable quantity.

In one example, a vector $f_x$ represents M sub meals as follows:

$$\underline{f_x} = [f_1, f_2, \ldots, f_M],$$

The caloric energy consumed by each portion of the M sub-meals can be expressed as a vector as follows:

$$\underline{e_{f_x t}} = [e_{f_1 t}, e_{f_2 t}, \ldots, e_{f_M t}],$$

In this expression, the total energy from the meal $e_{f_x t}$ consumed over time t will be the sum of all sub-meal energies, represented by the following:

$$e_{f_x t} = \sum_{i=1}^{M} e_{f_i t}$$

The nutritional density of nutrient n for each meal can be expressed in a vector as follows:

$$\underline{\delta_{nf_x}} = [\delta_{nf_1}, \delta_{nf_2}, \ldots, \delta_{nf_M}].$$

For nutrient n, then, the total amount of the nutrient n consumed in food $f_x$ is the sum of the product of the caloric energies of each sub-food and nutritional densities of each sub-food, which can be expressed as follows:

$$A_{nf_x t} = \underline{\delta_{nf_x}} e_{f_x t}^T = \sum_{i=1}^{M} \delta_{nf_i} * e_{f_i t}$$

In one example embodiment, the energy values are expressed in terms of grams, and the density is expressed in terms of energy per gram. Thus, the nutrient density of nutrient n for the meal is calculated as follows:

$$\delta_{nf_x} = \frac{A_{nf_x t}}{e_{f_x t}}.$$

This nutrient density and/or the amount of nutrient consumed can be used in Equation 1 (and consequently in Equation 2) above to calculate first the nutrient health score for each tracked nutrient in a meal $f_x$ and then to calculate a nutritional health score for the meal $f_x$ by summing the weight-adjusted nutrient health scores for each tracked nutrient. The disclosed system can perform the above calculations to advantageously calculate nutritional health scores of varying quantities of food, including foods that are the combinations of ingredients, meals that are the combination of foods, and diets that are the combination of meals.

In various embodiments, the disclosed system enables users to build foods or meals out of sub-foods or components of foods. For example, by indicating to the disclosed system what the user's "normal breakfast" is, the user can store a "breakfast" meal and simply select that one meal when entering an indication of foods he or she plans to eat or has already eaten. That is, the disclosed system enables users to build meals from foods or diets from meals, and to store those multi-component consumables for easy selection and entry at a later time. In some embodiments, the system also enables the user to adjust the amount of a particular multi-component consumable consumed, such as by indicating that the user ate half of his or her normal breakfast.

Figure 6:
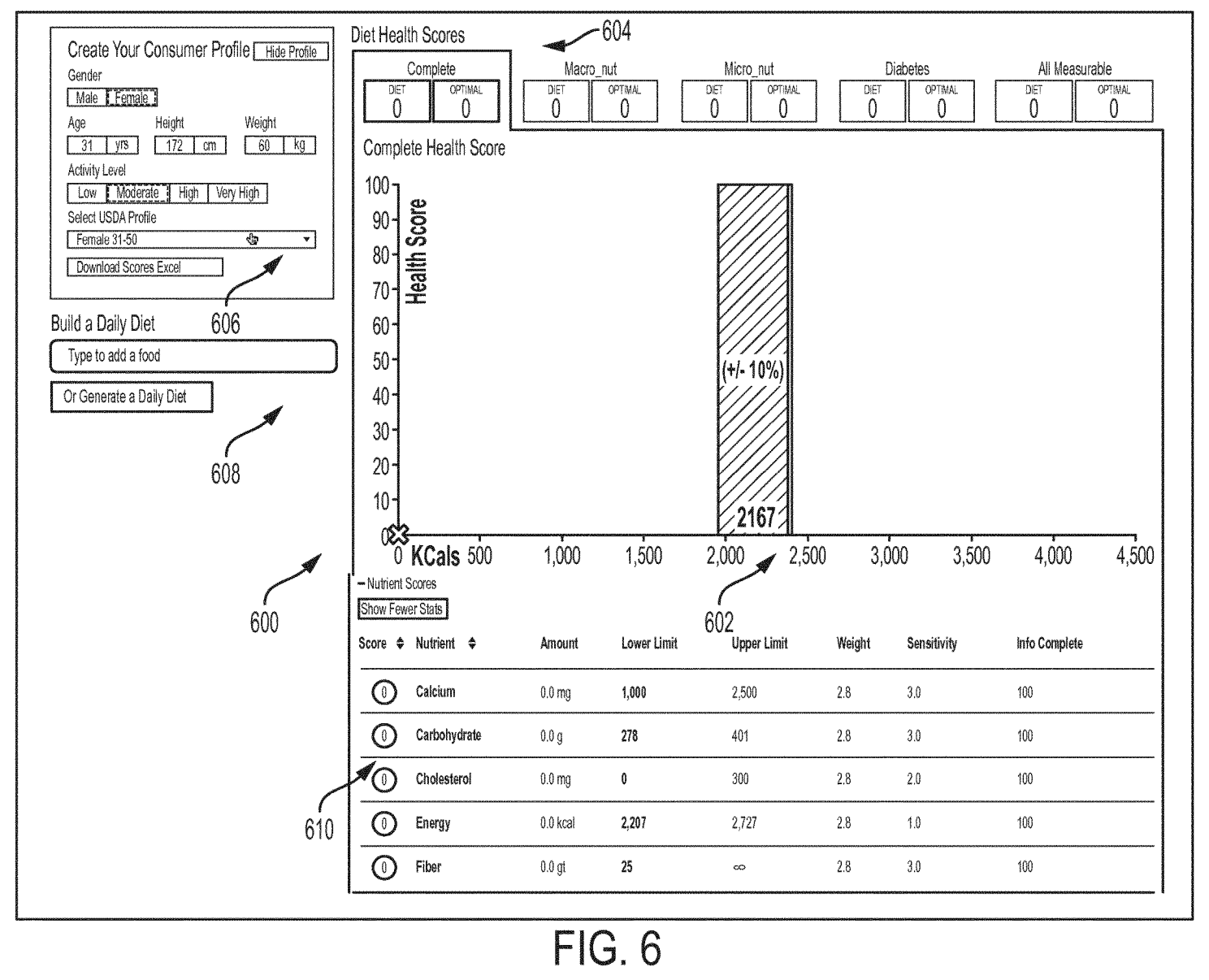

In various embodiments, the disclosed system provides users with a dashboard or other graphical user interface to view nutritional and nutrient health scores, track nutrient intake over time, and obtain advice about what food to eat to meet nutritional health goals. FIG. 6 is a screen 600 illustrating a portion of the dashboard interface provided by one embodiment of the disclosed system. In the illustrated embodiment, the screen 600 enables users to interact with the nutritional health scoring system described herein to explore the impact of eating certain foods, to view the nutritional health scores and component nutrient health scores for certain foods, and to obtain advice about what foods to eat to meet specific nutritional goals.

In the FIG. 6 embodiment, screen 600 includes a plurality of areas that provide different functionality, interaction, and/or displays to users of the instant system. Area 602 is a nutritional health score display area, and in various embodiments one or more calculated nutritional health scores for one or more consumables is displayed in area 602. In various embodiments, this area 602 also displays the caloric intake range for a user and the curve of nutritional health scores represented by consuming different amounts of a selected combination of foods. Area 604 is a selection area that includes a plurality of controls to enable users to select which scores should be active, and thus displayed, in the screen 600. In the illustrated embodiment, the different controls of area 604 take the form of different tabs, each of which displays an actual score and an optimal for a subset of the totality of the nutrients tracked by the disclosed system. Area 608 includes a plurality of controls to enable a user to enter consumed foods or to generate a daily diet. Area 610 displays numerical information about the amount of various nutrients indicated by consumed foods as indicated by the user. The functionality of these areas will be discussed in more detail below.

Area 606 is a personal information input area that enables a user to input information about himself or herself, including gender, age, height, weight, activity level, and applicable USDA profile. Depending on the information input via the various illustrated controls in area 606, the disclosed system personalizes the calculated nutritional health score(s) by adjusting lower healthy values, upper healthy values, weighting values, and/or sensitivity values to be a as specific as possible to the user. More specifically, depending on the information provided by the user in area 606, particular sets of lower/upper healthy values, weighting values, and/or sensitivity values will be calculated or selected for use from the appropriate database or data store. The information entered in area 606 may, for example, be used to select from among the plurality of population groupings illustrated in FIG. 5.

Referring still to FIG. 6, and specifically to area 602 of FIG. 6, a chart is displayed in which health score is illustrated on the vertical axis and Kcals (La, caloric intake) is illustrated along the horizontal axis. A block "X" is illustrated at the origin of the chart of area 602, indicating a score of 0 at a caloric intake of 0. This point is illustrated because, at the point in time illustrated in FIG. 6, food information has been provided to the disclosed system as part of a current diet. In the center area of the chart of area 602, a wide bar is illustrated. This bar illustrates the range of caloric intake determined to be optimal for the individual whose information is provided in area 606 over the one-day period reflected by the screen 600. Specifically, for a 31 year old female, 172 cm tall, weighing 60 kg, who is a moderate exerciser, the optimal caloric intake as suggested by the USDA is 2167 Kcals/day. It should be appreciated that in various embodiments, other sources for the suggested caloric intake could be used as appropriate. The thick bar in area 602 of FIG. 6 illustrates a range of caloric intake values for the person defined in area 606, where the range is defined as the optimal caloric intake plus and minus 10%. Accordingly, the illustrated bar spans approximately 1950 Kcal/day to approximately 2383 Kcal/day. In various embodiments, this range illustrates a target caloric consumption range for a given day. In one embodiment, the disclosed system enables the user to select and drag on the edges of the thick bar to adjust the width of the bar; this indicates that the user wishes to either expand or reduce the daily caloric intake range used in performing the various functions described below.

Referring to area 604 of FIG. 6, a control is provided which enables a user to select from a plurality of scores to display in area 602. In the illustrated embodiment, the "Complete" tab is selected, meaning that a score for all nutrients tracked by the system is presently being displayed. The illustrated embodiment also provides the option for the user to select a tab titled Macro_nut, in which the scores for only macro nutrients (e.g., saturated fat, cholesterol, sugar, total fat, and sodium) are displayed, a tab titled Micro_nut, in which the scores for only micro nutrients (e.g., Calcium, Carbohydrates, Fiber, Iron, Vitamins A, B, C, D, and E, etc.) are displayed, a tab titled Diabetes, in which the scores for only nutrients related to diabetic conditions (e.g., sugars) are displayed, and a tab titled All Measurable, in which scores for all measurable aspects of selected foods are displayed. Additional tabs could be provided to address different nutritional goals, such as goals related to weight loss or training for rigorous athletic events such as marathons. Additionally, in some embodiments, one or more controls could enable the user to select which nutrients to include in the health score when such control or controls are selected.

In the embodiment of FIG. 6, the various tabs in area 604 have different subsets of nutrients tracked in the implemented database of DRI values, an excerpt of which is shown in FIG. 5. Specifically, the "All Measurable" tab contains all the nutrients for which a DRI is stored in the database. Also in the embodiment of FIG. 6, the "Complete" tab contains all DRIs for which range values are stored, but weights the nutrients equally. In the other columns (e.g., the Diabetes column), different weighting values are applied and fewer than all of the tracked nutrients factor into the calculated nutritional health scores. Thus, it should be appreciated that in the illustrated embodiment, the tabs in area 604 enable a user to select a scoring regime particular to a specific nutritional goal or nutritional need.

Area 610 of FIG. 6 illustrates a portion of the screen 600 that displays numerical information about the nutrient contents of various foods either entered by the user or suggested by the system as part of a diet. In the illustrated embodiment the user has not indicated that any food has been consumed, so all the values in the Amount column of area 610 are 0.0. However, as will be described below, the numbers in the Amount column increase as foods are entered into area 608 that contain the various nutrients displayed in area 610.

Moreover, as can be seen from FIG. 6, for each displayed nutrient, the lower healthy amount (lower limit) and upper healthy amount (upper limit) are indicated in area 610. Also illustrated in the embodiment of FIG. 6 are the weighting values and sensitivity values ascribed to the various nutrients listed. As discussed above, these values are determined, in various embodiments, so as to be customized to a particular user or population of users based on those users' needs. In one embodiment, selecting the "Show Fewer Stats" will cause the last three columns displayed in area 610 of FIG. 6 to be hidden.

The values illustrated in area 610 are determined based on the personalization information provided in area 606. In the embodiment illustrated in FIG. 6, the upper limit for Fiber is infinity; this means that consuming additional fiber will not have a negative or downward impact on the overall nutritional health score, regardless of the amount consumed. It should be appreciated that in the embodiment of FIG. 6, the particular nutrients listed in area 610 depend upon which tab is selected in area 604. That is, if Macro_nut were selected in area 604 of FIG. 6, the listed nutrients would change accordingly by displaying, for example, carbohydrate, protein, saturated fat, and total fat.

In one embodiment, the disclosed system detects when a user has hovered over, moused over, or otherwise selected one of the nutrients listed in area 610 of FIG. 6. In this embodiment, when the system determines that the user has selected one of the nutrients, the disclosed system randomly selects a set of foods that would both improve the user's overall nutritional health score and also improve the nutrient health score for the selected nutrient. In this way, if a user sees that his or her diet is deficient in calcium while viewing the information in area 610, the system provides the user with a plurality of suggested ways to improve his or her calcium intake. In a further embodiment, each time the user hovers over or otherwise selects a particular nutrient, the system randomly generates a new listing of foods rich in the selected nutrient, such that the user can repeatedly see suggestions of different foods that would help increase the user's consumption of that nutrient.

Figure 7:
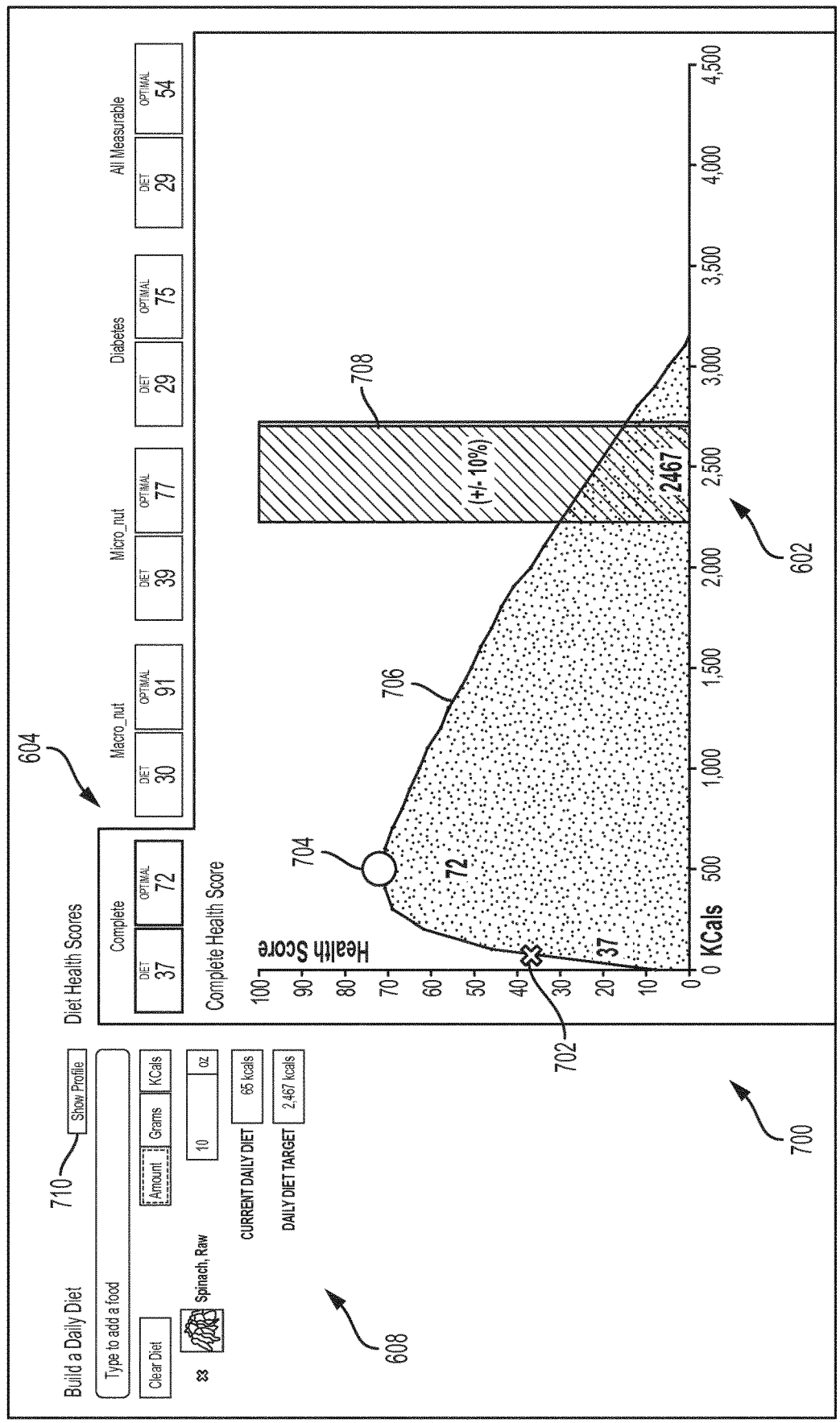
FIG. 7 is a screen shot showing an example of the interface provided to a user of the disclosed system in one embodiment after a single item has been added to a daily diet.

FIG. 7 illustrates a screen 700 of the embodiment of FIG. 6 after a food (spinach, raw) has been selected and added to the "daily diet" by the user. It should be appreciated that in the screen 700, areas 602, 604, and 608 are displayed, but area 606 from FIG. 6 has been hidden. In one embodiment, the disclosed system is configured to hide area 606 after the user has provided his or her personal information, as changes to the personal information of the individual using the system (and thus changes to lower and upper healthy ranges, weighting values, and sensitivity values) are unlikely after initial configuration. In another embodiment, the system provides a control (such as control 710 of FIG. 7) that toggles between displaying and hiding the user profile adjustment area of the screen 700. In another embodiment, the area 606 is displayed as a pull-down drawer that hides automatically when the user has not moused-over or otherwise provided an input to indicate a selection of the area 606.

As can be seen on screen 700, the user in FIG. 7 has illustrated in area 608 that he or she has consumed 10 ounces of raw spinach. Area 608 thus displays a calculated amount of calories for the spinach (65 Kcal) calculated as described above by multiplying a stored indication of the calories per unit by the amount of spinach indicated. This value is displayed as the "Current Daily Diet" since at this point in the usage, the only thing the person has eaten is 10 ounces (65 Kcal) of raw spinach. For convenience, the system also displays the person's daily diet target.

Referring still to FIG. 7, area 602 has changed from the illustration of that area in FIG. 6. Specifically, in area 602, the "X" icon 702 has moved away from the origin, to a point that corresponds to 65 Kcal and a Health Score of 37. In this embodiment, the "X" icon 702 in area 602 indicates the nutritional health score calculated for the current diet (i.e., 10 ounces of raw spinach) consumed in a one-day period. This nutritional health score for the actual diet consumed is calculated as described above.

Area 602 also contains a large circle indicator 704 that is at the peak of the curve 706 in area 602. In this embodiment (and in the other embodiments discussed with regard to FIGS. 8, 9, and 10) the illustrated curves are determined by calculating the nutrient health scores for each component nutrient using Equation 1 above, and aggregating the contributions of the nutrients in the diet using Equation 2 above. Moreover, the curve shape is achieved by adjusting the amounts of component foods consumed to result in the different caloric intake values illustrated along the horizontal axis of FIGS. 7, 8, 9, and 10. Accordingly, in various embodiments, the curves illustrated in FIGS. 7, 8, 9, and 10 are determined by repeatedly calculating nutritional health scores as disclosed elsewhere herein. Moreover, for each caloric intake value on the horizontal axis of FIGS. 7, 8, 9, and 10, the disclosed system determines an optimal nutritional health score for the foods then present in the diet by selecting the optimal resulting score for the various amounts of food in the diet that, if consumed together result in that particular caloric intake value. For instance, in a situation where the two foods indicated as being consumed are spinach and chocolate, and the amount to be plotted on the curve corresponds to 1000 calories ingested in a day, the system disclosed herein determines the nutritional health score for consuming 1000 calories of spinach, 1000 calories of chocolate, and every combination of spinach/chocolate that results in 1000 calories, and plots the score the combination with the highest overall nutritional health score. In embodiments where the user has indicated an amount of spinach and chocolate consumed, the system in one embodiment does not calculate nutritional health scores for combinations of spinach/chocolate where the amount of either item is less than the indicated amount. In a prospective embodiment, where the user indicates the intention to consume amounts of spinach and chocolate, the disclosed system calculates nutritional health scores for all combinations of spinach/chocolate and if an optimal score can be achieved by reducing one of the two indicated intended amounts, the system suggests that the intake of that food be reduced to maximize score.

Referring again to the embodiment illustrated in FIG. 7, indicator 704 represents a maximum health score/caloric intake that could be achieved by eating more of the current diet in the given time period of one day. That is, given that the current diet consists of spinach, a maximum health score of 72 could be achieved by eating approximately 550 kcal worth of raw spinach in a day. If the person eats more spinach up to the approximately 550 kcal amount indicated as providing a maximum health score, the health score will continue to increase. Likewise, if the person eats more spinach in a given day than the approximately 550 kcal amount indicated as providing the maximum health score, the health score will begin to decrease and will eventually reach a value of 0 at approximately 3100 kcal worth of spinach. Accordingly, the embodiment of FIG. 7 illustrates one aspect of the advisory functions provided by the disclosed system, in that it illustrates the amount of a particular food (i.e., the current diet) that would need to be consumed in a given time to obtain an optimal health score.

The data in area 602 also indicates to the user of the system that even if the optimal amount of the current diet (i.e., raw spinach) was consumed over a given time period to obtain an optimal score, the user's daily caloric intake would not be in the suggested range illustrated by bar 708. Accordingly, the user can tell at a glance that if he or she were consume the daily recommended amount of calories in the form of the current diet, the user would have a nutritional score far below the optimal nutritional score that could be achieved eating the current diet.

Referring now to area 604 of FIG. 7, it can be seen that the controls of area 604 have been updated in FIG. 7 to reflect the current entered diet of 10 ounces of raw spinach. Specifically, in the illustrated embodiment, the active tab (La Complete) lists the current score for the actual diet (a value of 37) and the optimal value that could be obtained by eating more of the current diet (a value of 72). The other tabs of area 602 have been updated as well, indicating the diet score and optimal score when only the subsets of nutrients for each tab are used to calculate health scores. In one embodiment, the unselected tabs (and therefore the scores associated with the combinations of nutrients for the unselected tabs) are translucent or faded to readily illustrate which tab is currently selected.

Figure 8:
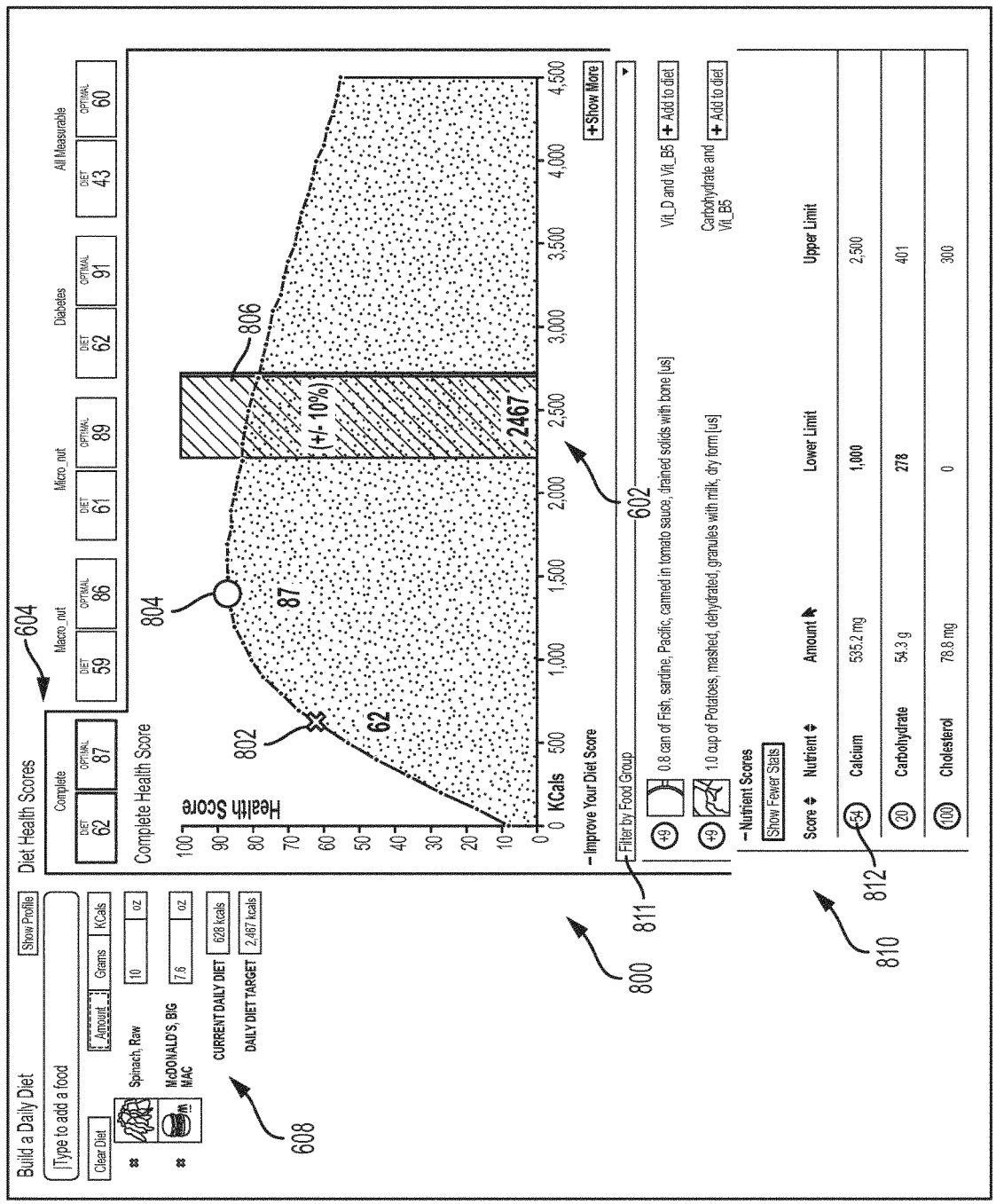
FIG. 8 is a screen shot showing an example of the interface provided to a user of the disclosed system in one embodiment after multiple items have been added to a daily diet.

FIG. 8 illustrates a screen 800 provided by the disclosed system in which the user has added a hamburger to his or her daily diet, which as can be seen from area 608, now consists of 10 ounces of raw spinach and a 7.6 ounce hamburger. "X" icon 802 indicates that the person's nutritional health score for the current daily diet is 62, and the total amount of calories consumed is 628. Circular icon 804 indicates that the maximum health score that can be achieved by eating the indicated daily diet is a score of 87, and that approximately 1500 calories worth of the indicated diet would need to be eaten in a day to achieve that result. The scores in area 604 are correspondingly updated to reflect the diet score and optimal score of the new diet. From analyzing the screen 800, the user can readily tell that he or she is well under his or her daily caloric intake range, and that if he or she were to eat enough of the diet to fall within the desired daily caloric intake range, he or she would be experiencing diminishing returns in terms of nutritional health score from the diet.

Having discussed FIGS. 7 and 8, one of the important advantages of the disclosed system can be seen. Namely, the disclosed system enables a user to visually see, at a glance, whether the diet they have chosen satisfies their nutritional needs in terms of calories per day and whether the diet they chose could have provided additional nutritional benefits (i.e., a higher health score) if eaten in different amounts. In one embodiment, using the paradigm illustrated in FIGS. 7 and 8, a user tries to maximize his or her diet by selecting foods that provide for a diet score and an optimal score are identical or nearly identical, wherein the amount of calories consumed to reach this result is within the person's optimal caloric intake range. Graphically, this would appear in the form of icons 802 and 804 of FIG. 8 being on top of one another and located within the bar 806 indicating the person's ideal caloric intake.

If the icons are nearly on top of each other but to the left of the bar 806, that indicates to the user that while he or she is getting the optimal nutritional value out of his or her food, he or she is not eating enough calories in a given day. If the icons are nearly on top of each other but to the right of the bar 806, that indicates to the user that while he or she is getting the optimal nutritional value out of his or her food, he or she is consuming too many calories in a given day.

If the icons are not on top of one another, the user can tell at a glance that he or she is not consuming an amount of his or her current diet to get the optimal nutritional value out of that diet. If the "X" icon 802 (representing the score for the actual diet) is to the left of the circle icon 804, that indicates to the user that eating more of the same diet would provide better nutritional value to the user. If the "X" icon 802 is to the right of the circle icon 804, that indicates to the user that eating less of the same diet would provide better nutritional value.

Accordingly, one of the advantages of the instant system is to provide a visual display to the user that quickly and easily indicates whether the user is consuming the right amount of his or her current diet and whether the user is consuming the enough calories in a given period of time.

In one embodiment, the disclosed system enables the user to click on or otherwise select the icon representing the optimal score to cause the other (actual diet score) icon to move to the optimal icon position on the curve. In this embodiment, the system updates the amounts of food in the current diet accordingly. In this way, the system enables the user to determine how much of a given diet to eat to achieve the optimal nutritional health score for that diet. Thus, if a user determines that in a given day he wants to eat eggs, a sandwich, a piece of chicken, and rice, the user can enter those four menu items and determine the amount of each to consume to achieve the optimal health score. The user can also quickly see whether those optimal amounts, if consumed, would result in a caloric intake within or outside his optimal caloric intake range for the day. In other embodiments, the user can drag the icon indicating the score for the actual diet to any point on the curve of nutritional health scores, enabling the user to see the amounts of various foods in the diet that would need to be consumed to achieve various scores along the curve.

Referring still to FIG. 8, area 810 is illustrated as appearing below area 602. Area 810 in the illustrated embodiment includes two collapsible menus titled "Improve Your Diet Score" and "Nutrient Scores."

With regard to the "Improve Your Diet Score" menu of area 810, one embodiment of the disclosed system displays one or more food items in that area that, if consumed, would boost the user's nutritional health score by a given amount. For example, in the embodiment of FIG. 8, consuming the recommended fish (sardines), which is indicated as containing Vitamin D and Vitamin B5, would improve the user's nutritional health score by 9 points. Likewise, consuming the listed potatoes, which include carbohydrates and vitamin B5, would also improve the user's score by 9 points. The system in one embodiment provides an "Add to diet" control next to each of the foods listed in area 810 that allows the user to add the item to his current active diet and updates the scores displayed in areas 602 and 604 accordingly.

In one embodiment, one or more items that are currently a part of the user's entered diet are listed in the "Improve Your Diet Score" menu of area 810. In this embodiment, the listing of a currently included item includes a control to allow the user to remove that item from his or her diet. In this embodiment, if an item is listed for removal in the "Improve Your Diet Score" menu, it means that the system has determined that removing (or reducing the quantity of) the item would actually result in a higher nutritional health score. Put another way, adding that item caused the overall nutritional health score to be reduced. This provides the user with an easy visual indication that one or more items in his or her diet are actually reducing the nutritional health of the diet because those items' calories were added without corresponding benefit being obtained from whatever nutrients are contained in the items.

In an embodiment, the disclosed system may suggest to the user that by reducing the amount of a particular food consumed, the user would improve his or her overall nutritional health score. In this embodiment, the disclosed system displays an appropriate control to enable the user to reduce (but not remove) the amount of a particular consumable that is being consumed.

In one embodiment, the user can select a control, such as "Filter by Food Group" control 811, to provide the user with control over the suggested foods displayed in the "Improve Your Diet Score" section. For example, if the user does not eat meat, the user could select control 811 to select "Vegetables" and thereafter only see suggestions of vegetables that could be added to the diet to improve the overall nutritional value score.

The information and controls provided in area 810 of screen 800 are one example of the advisory function provided by the disclosed system; by suggesting foods that can be either added or removed to improve the user's nutritional health score, the system has the potential to positively affect the user's food choices rather than serving simply as a reporting tool in which the user merely enters foods he or she has already consumed. Moreover, by enabling the user to filter the suggested foods to add, the system enables the user to augment his or her food consumption while still consuming foods the user enjoys eating.

The disclosed system advantageously enables a user to dynamically alter the contents of his or her diet by adding and/or removing items from the area 608 and quickly and easily seeing, in a visual way, the impact of those additions or subtractions on his or her overall health score. By selecting suggested foods from the "Improve Your Diet Score" section of the display, the system is able to suggest foods to the user that may optimize gains in nutritional health score that the user might not necessarily have realized. Thus, the system does not rely on the user alone to add or delete foods of his or her own choosing to the current diet.

With regard to the "Nutrient Scores" menu of area 810, similar information to that discussed with regard to FIG. 6 is being displayed, although the numbers are updated to reflect the food consumed by the user. For example, in the diet of spinach and a hamburger entered by the user, it can be seen that 532.2 mg of calcium have been consumed. In the illustrated embodiment, the displayed lower and upper limits (1,000 mg and 2,500 mg, respectively) readily indicate to the user that he or she is not yet in the healthy range of calcium consumption. As further evidence, the disclosed system in one embodiment displays a nutrient score dial 812 that contains the nutrient health score (i.e., the score for a particular nutrient, before weighting values area applied) for the particular nutrient (in this case, a value of 54 for calcium). In the illustrated embodiment, the score dial 812 displays a value calculated in the way described in Equation 1 above.

In one embodiment, the score dial 812 is also color-coded, for example with a red color to indicate that a nutrient health score is relatively low, a yellow color to indicate that the nutrient health score is medium, and a green color to indicate that the nutrient health score is good. These features all enable users, at a glance, to discern which nutrients they are consuming enough of and which need to be consumed in additional amounts.

It should be appreciated that the information displayed in the "Nutrient Scores" menu of area 810 advantageously enables a user to determine which nutrients are being consumed in healthy amounts and which are being consumed in unhealthy amounts. Particularly given the ability to sort nutrients by nutrient health score, which is provided in certain embodiments of the system disclosed herein, a user can readily see which nutrients he or she is either under-consuming or over-consuming, and which nutrients are being consumed within a health range for those nutrients.

It should be appreciated that because the different tabs in area 604 of the embodiments illustrated in FIGS. 6, 7, and 8 calculate nutritional health scores by aggregating different sets of nutrients, it is possible that the scores for the different tabs could be different. Moreover, it is possible that for some subsets of nutrients, the actual diet score and the optimal score may be relatively close together, and for other subsets, the scores may be very far apart. For example, in a diet high in sugar content, it is possible for an optimal macro nutrient score to be very near an actual macro nutrient score, while an actual diabetes score may be very disparate from an optimal diabetes score. This may reflect the fact that reducing items high in sugar may reduce the actual macro nutrient score while improving the actual diabetes score.

Referring again to FIG. 6, the illustrated embodiment of area 608 includes a plurality of controls. The text entry control of this embodiment has already been described with regard to the user's ability to enter the word "spinach" to add spinach to his or her daily diet. In the illustrated embodiment, another control in the form of a button titled "Generate a Daily Diet" is also provided in area 608. In this embodiment, clicking or otherwise selecting the "Generate a Daily Diet" button results in the display of the screen 900 of FIG. 9. In other embodiments, the disclosed system provides controls for generating diets or meal plans over different periods of time, such as on a meal-by-meal basis, weekly, or monthly.

When the user selects the "Generate a Daily Diet" button, the disclosed system selects a plurality of foods for which the optimal health score occurs at the low end of the caloric intake range for a person over a given period of time. In other words, the disclosed system selects combinations of foods to determine an optimal nutritional health score without the user needing to eat more calories than necessary. In one embodiment, if the user has already manually added certain foods by typing their names into the search control or by selecting the "Add to diet" control, the disclosed system maintains those foods in the selected amounts, and attempts to add additional foods to maximize the nutritional health score. In another embodiment, the system is able to remove certain added foods if the user has indicated that he or she has not yet eaten those foods, but rather that he or she intends to eat those foods. If the added foods are intended to be eaten, the system may reduce the amount of those foods or remove them altogether to maximize the recommended diet. In one embodiment, this functionality is achieved by providing a lock icon or other similar control to allow the user to indicate that a particular food cannot be removed (i.e., that the user has already eaten it).

In various embodiments, the disclosed system uses one or more guidelines in generating a daily diet. For example, in one embodiment, the system uses one or more preferences provided by the user (such as a preference for beef) to build a cornerstone or baseline meal for the period of time. From that point, the disclosed system may attempt to pick main courses for the other meals of the day, and thereafter fill in the caloric and nutrient needs with side items for the three meals.

In another embodiment, the system randomly selects one or more food items to base a diet on and fills in around those items. In one embodiment, the system keeps track of past days' food items and tries not to repeat items that have been eaten recently. In one embodiment, the system maintains an inventory of items in a user's home, and suggests a diet based only on what the user has at his or her disposal. In one embodiment, the system is configured to automatically place orders for the delivery of food needed to prepare the diet; in this embodiment, the system places orders based on what is indicated as being in stock at a local grocer. In one embodiment, the system tracks the cost of food items and attempts to provide a diet that not only maximizes health score at an acceptable caloric intake, but attempts to do so while minimizing the cost of the ingredients in the diet.

Figure 9:
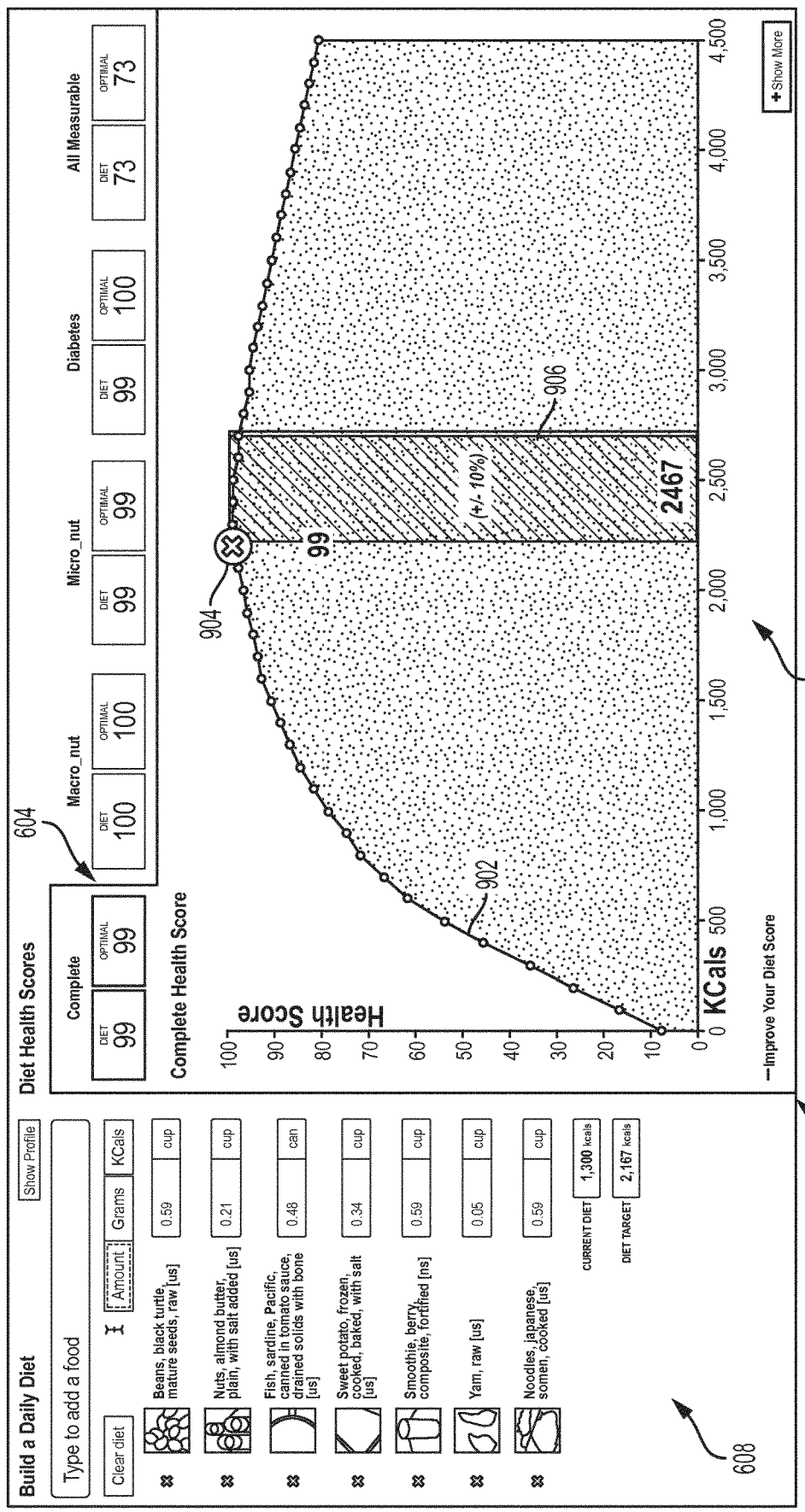
FIG. 9 is a screen shot showing an example of the interface provided to a user of the disclosed system in one embodiment after the system has been used to generate a suggested daily diet to meet the individual's nutritional health needs.

Referring now to FIG. 9, the illustrated screen 900 (generated by selecting the "Generate a Daily Diet" button) includes a curve 902 similar to the curve discussed with regard to FIGS. 7 and 8 above. Moreover, in the screen 900 of FIG. 9, a plurality of food items selected or suggested by the disclosed system are displayed as being part of the daily diet. In this embodiment, the curve 902 reflects the nutritional health score of the displayed diet at different amounts of consumption of those foods.

As can be seen in area 602 of FIG. 9, the diet health score icon and the optimal health score icon are both illustrated at the same point 904 on the curve 902; that point 904 is the maximum value of the curve 902. Moreover, FIG. 9 illustrates that the optimal point 904 of the curve 902 is located at the lower end of the caloric intake range 906. Further, area 608 includes a plurality of food items that were generated by the system upon the user selecting the "Generate a Daily Diet" control of FIG. 6. The curve 902 is the curve indicating the nutritional health score of the items of the generated diet for various different caloric intake values from 0 to approximately 4500 kcal/day.

Accordingly, the disclosed system provides an additional advisory function by suggesting foods, meals, or diets to a user to meet specific caloric goals while optimizing nutritional health scores over a given period. This also represents a substantial improvement over known schemes, where users must select foods in a trial-and-error use case, examining the impact of those foods on the diet only after the foods have been selected.

In the embodiment of FIG. 9, once the user has generated a daily diet whose health score is at an optimal point at the low end of the caloric intake range for a given day, the user can interact with the system in the ways described above. For example, if the user does not like one of the foods listed as part of the daily diet, the user can remove that food item and see the impact on health score of such removal. At that point, the system can suggest foods to add to further increase the nutritional health score. The user can also manually add items to the menu, and the system displays the impact on the nutritional health score and the actual caloric intake for the given time period as described above.

In one embodiment, the disclosed system generates a diet that optimizes the particular health score for the tab of area 604 that is currently selected. Thus, if the macro nutrients tab is selected, a diet may be selected to optimize the nutritional health score for nutrients considered to be macro nutrients, even though other tabs (such as the Complete tab) show nutritional health scores that are sub-optimal.

Figure 10:
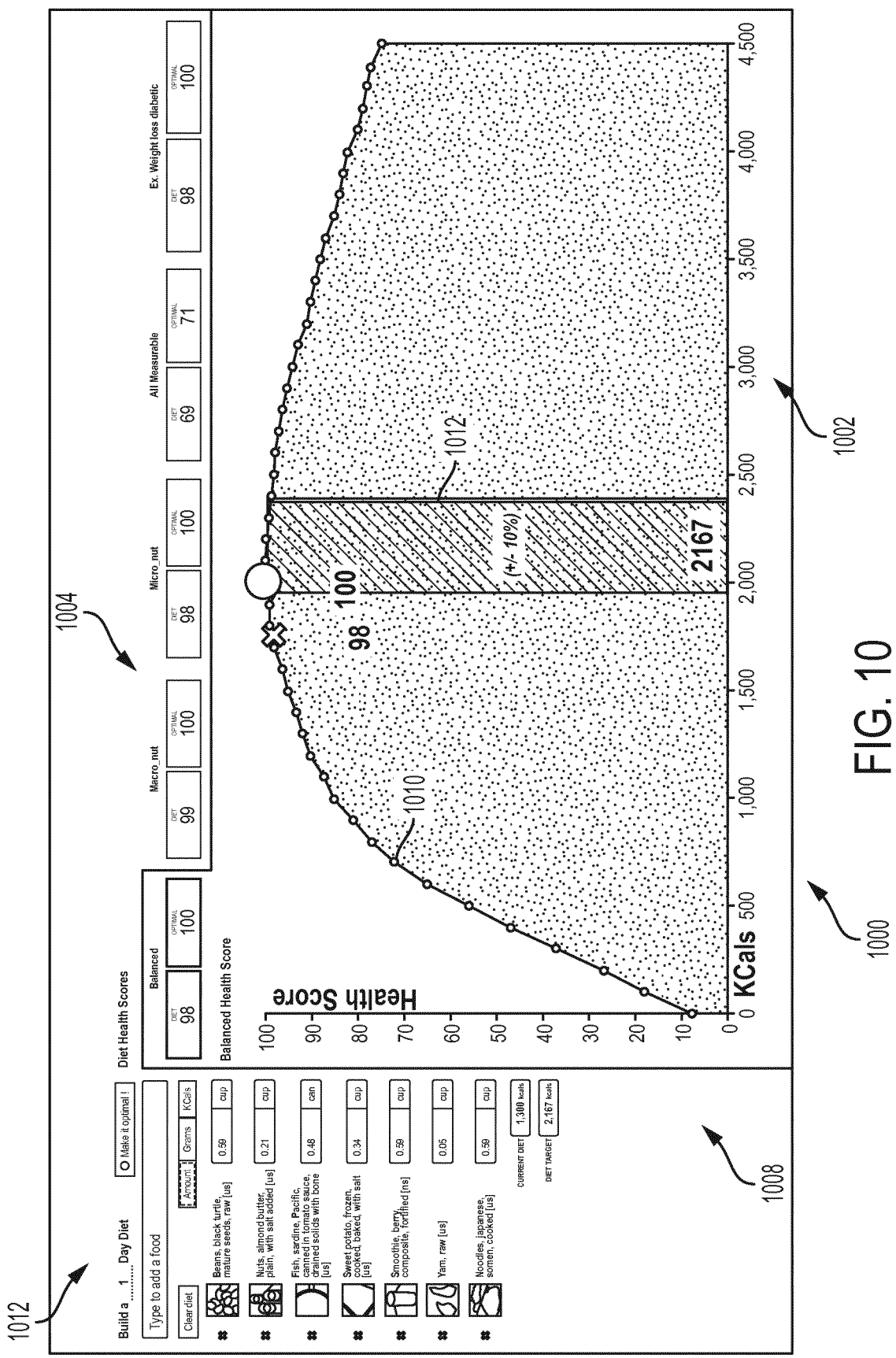
FIG. 10 is a screen shot showing an example of the interface provided to a user of the disclosed system in an alternative embodiment to that illustrated in FIG. 9.

FIG. 10 illustrates an alternative embodiment of a user interface provided by the system disclosed herein. In the embodiment of FIG. 10, screen 1000 illustrates an area 1002 displaying a curve 1010 plotted against a caloric intake range 1012. These features are similar to those features described in area 602 of the previously discussed embodiments of the user interface.

Area 1004 of FIG. 10 illustrates a plurality of tabs, each of which includes a pair of scores calculated for different combinations of nutrients, similar to the discussion of area 604 of the previously discussed embodiments of the user interface of the disclosed system.

Area 1008 of FIG. 10 is an area of the user interface in which the disclosed system displays a plurality of foods that are contributing to the nutritional health scores indicated by the curve 1010. In the illustrated embodiment, for each of the foods listed in area 1010, the user has the option to select an "X" icon to the left of the food, which causes the disclosed system to remove that food from the area 1010 and to re-calculate the nutritional health score based on the remaining food. Area 1010 also displays a plurality of input controls which enable a user to adjust the amount of a particular food that is contributing to nutritional health score, without removing the food entirely.

Area 1010 of FIG. 10 differs from the previously discussed dashboard user interface in part because of the diet building information displayed in area 1012. Specifically, in the embodiments illustrated in FIGS. 6 to 9, the disclosed system is configured to perform all calculations and recommendations for food consumed in a single day. Thus, the caloric intake range of FIGS. 6 to 9 is calculated for a single day, and each of the foods added to the calculation of the nutritional health score are presumed to be consumed in a single day. In the embodiments illustrated in FIGS. 6 to 9, therefore, all scores, amounts of caloric intake, and nutrient amounts are entered, manipulated, and determined as a function of time; the time for which the data of FIGS. 6 to 9 applies, however, is static at one day.

FIG. 10 represents an embodiment with additional functionality from that of FIGS. 6 to 9 in part because the area 1010 enables a user to specify the time period (i.e., the number of days) for which the screen 1000 applies and for which the diet is to be built. This can be seen by the number "1," which is alterable by the user, in the section of the screen 1000 labeled "Build a 1 day diet." In the illustrated embodiment, the user can adjust the number 1 to specify a desire to build a diet spanning multiple days, and can also specify numbers of days less than 1. For example, in one embodiment, if a user wishes to build a single meal of a three meal day, the user can enter the number 0.33 in the area 1012. If the user wishes to build a diet for a full week, the user can enter the number 7 in area 1012.

In the illustrated embodiment, the number entered in area 1012 provides a scaling factor that is used to scale the caloric intake range for a user to match the number of days (or fractions of days) for which a diet is to be built. This scaling, in one embodiment, results in the scale across the horizontal axis of area 1002 and also to change the recommended caloric intake range indicated in bar 1012 to reflect the entered amount of time. Also in this embodiment, the number entered in area 1012 is used to scale the lower and upper healthy range numbers for the various nutrients tracked by the disclosed system. In one embodiment, the scaling is a direct, linear scaling, such that stored values representing daily intake amounts are simply multiplied by the number entered in area 1012. In another embodiment, the system is configured to weight certain values, such as caloric intake values, to reflect a user's preference to consume calories in different proportions for different meals. For example, if a user wishes to consume 75% of his or her calories at breakfast and dinner, the system may be configured to ask the user which meals he or she would like to plan, and multiply the range values by an appropriate weighting value. In some embodiments, the system provides selection controls in area 1012 that enable the user to select which particular meals he or she would like to plan or track.

It should be appreciated that in the embodiment of FIG. 10, therefore, different periods of time can be used other than a single day. Specifically, the disclosed system in the embodiment of FIG. 10 provides a user with one or more controls to input the amount of time for which the user wishes to indicate food consumption and see nutritional health scores. This may allow the user to plan meals, daily menus, or weekly or monthly diets, depending on the amount of time indicated by the user.

Referring still to FIG. 10, the "Make It Optimal" control of area 1012 in one embodiment runs a simulation by calculating the impact on overall nutritional health score of each food item in a food database. In one embodiment, the first foods that are selected are randomly selected, and a meal or diet is built around the selected foods. In one embodiment, the disclosed system stores data indicating a common serving size for various foods in its database; in this embodiment, the system ensures that it does not exceed a single serving size by more than a set amount, such as by more than 20%, for a given food. Thus, in one embodiment, the system starts by selecting one or more primary foods for a given meal or diet, and fills in with secondary foods without substantially exceeding recommended serving sizes.

In one embodiment, the "Make It Optimal" functionality causes the disclosed system to calculate nutritional health scores for each food in the database in three different serving sizes. For example, the system may calculate the impact on nutritional health score for an amount under the serving size, an amount equal to the serving size, and an amount in excess of the serving size. Using these three scores for each food item, the system iteratively locates combinations of foods that contain approximately the right number of servings/meals while at the same time maximizing nutritional health score.

The system in various embodiments executes the "Make It Optimal" functionality by optimizing the existing diet through additions and reductions in amount of foods in the existing diet toward a perfect or optical score given the particular scoring profile that is being applied for the individual. Scoring profiles may in various embodiments apply different healthy ranges, weighting parameters, and/or sensitivity parameters depending on the individual to whom the scoring profile applies. Accordingly, scoring profiles may be different for different clicks of the "Make It Optimal" button. In this situation, the recommendations that will make a score optimal may be different depending on the scoring profile being applied at the time of optimization.

In one embodiment, the disclosed system determines a caloric intake range to apply for a particular individual by performing a database lookup, such as by searching a database or data structure of caloric intake ranges recommended by the USDA. In another embodiment, the disclosed system calculates caloric intake ranges by applying one or more equations that takes into account the user's age, weight, Body Mass Index (BMI), gender, activity level, and other appropriate considerations. In this embodiment, the equation may be one provided by a governmental agency, such as the USDA. In other embodiments, the system calculates optimal caloric intake ranges by considering data from external sources, such as fitness trackers, activity bands, exercise logs, or other indicators of activity levels of an individual. In one such embodiment, if data from one of these other sources indicates that the individual is very active and is burning more calories a day than the USDA guidelines indicate, the disclosed system may adjust the user's caloric intake range upward accordingly. Likewise, if data obtained from one of the listed sources indicates the user is relatively sedentary, the system may adjust his or her caloric intake range downward.

In one embodiment, the disclosed system enables a user to select from among a plurality of databases of lower and upper healthy range values, such as by selecting databases of lower and upper healthy range values sourced from different organizations or different countries. For example, in one embodiment the disclosed system enables users to select from databases of healthy range information provided by the USDA on the one hand and governmental bodies in New Zealand on the other hand.

In one embodiment, the disclosed system displays a slider or other control that enables a user to indicate the percentage of day the actual diet applies to. For example, if a user had a relatively small breakfast and a relatively small lunch, he or she may enter the food items in those meals and indicate, via the slider, than 66% of the day's meals have been consumed. Using that indication, the system in one embodiment knows that it is recommending foods only for a single meal, and thus may recommend relatively higher-calorie options or larger amounts of food that it otherwise would. Alternatively, if a user wishes to build an optimal breakfast that only uses 25% of his or her daily calories, one embodiment of the percentage control enables the user to indicate that he or she would like an optimally arranged breakfast totaling 25% of his or her total daily calorie intake. In still another embodiment, if a user has a particularly heavy eating day, the user may indicate via a percentage slider that he or she consumed 200% of the user's daily calorie intake. The system can then take that extra consumption into account in creating a diet for the remainder of the week.

In one embodiment, the system disclosed herein enables a user to design a score for a particular application. In this embodiment, a single user may have multiple scores for the same meal. For example, the disclosed system calculates and displays a "complete" score that attempts to optimize all measurable features in the food (i.e., all nutrients in the food), and also calculates and displays a "weight loss" score that attempts to optimize a subset of measurable features (e.g., minimizing carbohydrate and saturated fat intake) or a different set of measurable features that, when optimized, drives the loss of weight. In this embodiment, a single consumable may have a "complete" score of 95, indicating that it is a relatively good contributor to overall health, but a "weight loss" score of 70, indicating that it is a sub-optimal consumable if the goal is losing weight. One mechanism for implementing this ability to generate multiple scores for multiple functions is illustrated in area 604 of FIG. 6 in the form of a plurality of different tabs, with each tab including scores calculated from different subsets of the tracked nutrients. Similarly, area 1004 of FIG. 10 provides for the ability to select from a plurality of different tabs, with each tab resulting in a different nutritional health score based on a different set of nutrient health scores contributing to the overall score and/or based on the application of different weighting values. In area 1004 of FIG. 10, it can be seen that one of the tabs is labeled "Ex. Weight loss diabetic." This tab, when selected, displays scores that are optimized for individuals who are diabetic and wish to lose weight; for this reason, the impact of sugar may be heightened and the importance of staying near the low end of the caloric intake range may also be emphasized.

Another possible mechanism includes a plurality of controls to enable the user to specify a custom subset of nutrients to include in a nutritional health score designed for a particular application. In still other embodiments, one or more nutrition professionals can provide inputs to the disclosed system to define various templates that may be useful to different individuals, such as by defining a "weight loss" template that calculates nutritional health score for a plurality of nutrients known to be especially important for achieving weight loss goals.

FIG. 11(*a*) graphically depicts one embodiment of the measurable component ("MC") scoring function of nutritional health for a single MC in a NC. In this embodiment, each MC score is combined into a single aggregate scoring function for a nutritional consumable ("NC") through a weighted average of MC scoring functions. The aggregate score for a NC is termed the Health score or "H-score" in various embodiments herein. In this embodiment, the higher the H-score, the higher the GNH and conversely, the lower the H-score, the lower the GNH. In the embodiment illustrated in FIG. 11(*a*), the MC scoring function is defined by 3 parameters: 1) a Lower Healthy Range (LHR), 2) an Upper Healthy Range (UHR), and 3) a tolerance 0-crossing (tolerance).

In the embodiment of FIG. 11, weighting of individual measurable components are used to create a total nutritional consumable score. In this embodiment, a NHF measurable component (MC) scoring function is used for any nutritional consumable. "Healthy Eating Index" or "HEI" scoring functions are used for food components in diets. So-called HEI-2010 scores are produced for diets by selecting the score at 1000 kcal along the function for any diet. In this embodiment, nutrient profiling scoring functions are used for nutrients in foods such as those used by NRF9.3, SAIN, LIM. Nutrient profiling scores are produced for foods by selecting the score at a specified amount for all foods (100 kcal, 100 g, serving size, etc.).

In one embodiment, instead of a NC having only a single score at a single amount (i.e. 100 kcal, 100 g, 1000 kcal, one serving), the MC score (and correspondingly the score for a NC) is a function of amount. In this embodiment, an overall single score is still produced for a given amount of the MC, but the amount need not be the same for each food or for all diets. In this embodiment, two invariant H-scores exist for a NC as a function of amount: 1) Hmax: the maximum H-score attainable and 2) Hx: the H-score when any MC crosses the first of any UHRs. While the amounts may be different between foods or diets in these two scores, the scores themselves in this embodiment may have the same meaning. The meaningful scoring of foods and diets at different amounts addresses many challenges facing nutrient profiling today.

In the embodiment of FIG. 11, LHRs and UHRs are the points at which the MC-score begins to decrease; that is, the score decreases below the LHR and decreases above UHR. In general, LHR and UHR values can be set to any appropriately defined value and can also be set to 0 or infinity if they do not exist or are unknown. Ideally, these values would be evidence-based. The tolerance defines the slope of the scoring function after crossing the UHR. The higher the tolerance the slower the score decreases after crossing the UHR (decreased impact on general health score). The lower the tolerance the faster the score decreases after crossing the UHR (increased impact on general health score).

Figure 11A:
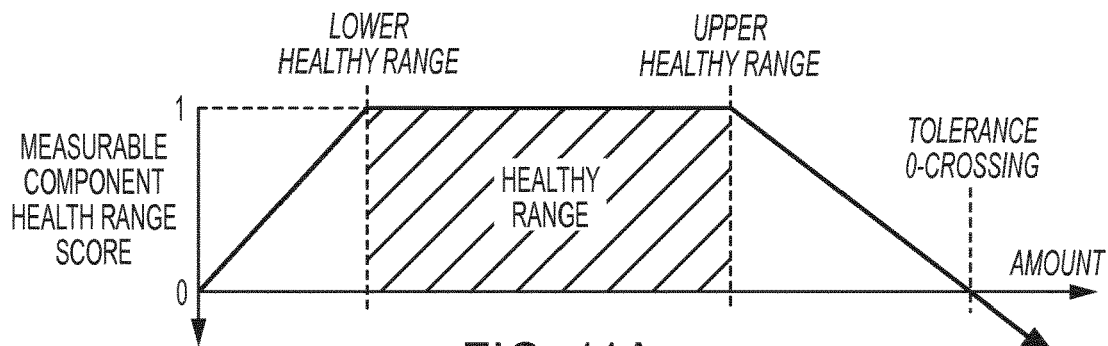
FIG. 11 illustrates scoring functions used in various embodiments of the disclosed nutritional scoring tools to score measurable components.
Figure 11B:
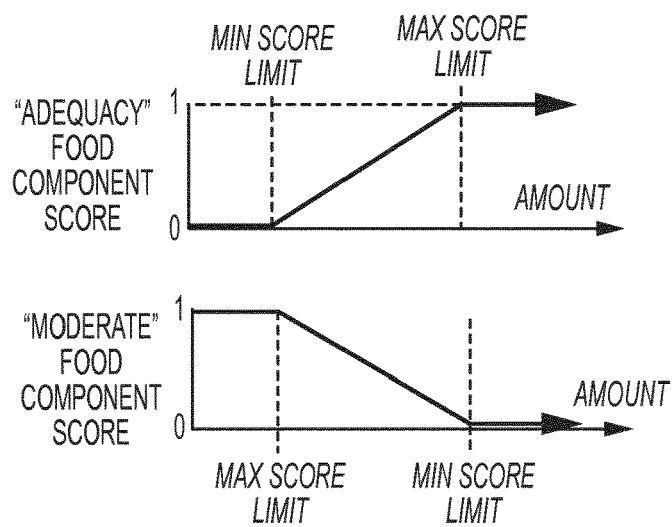
Figure 11C:
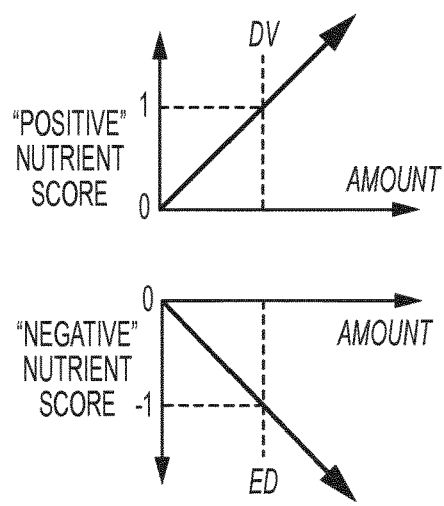

The NHF MC-scoring function can be partially viewed as a hybrid between DQI scoring functions in FIG. 11(b) that saturate and nutrient profiling scoring functions in FIG. 11(c) that are unbounded. In the illustrated embodiment, the NHF combines the best of each into a single function with both saturation and unbounded components, but the NHF does not distinguish between different types (i.e. positive/negative) measurable components. Scores are viewed simply as within or outside a healthy ranges which importantly enables all MCs to be treated equally in a single scoring function. The result of using healthy ranges for the scoring is to remove the subjectivity of classifying nutrients or food components and open the possibility of utilizing any MCs that can not be classified but have ranges of intake (further discussion can be found in the supplementary material).

In the embodiment of FIG. 11(a), the following discussion of a mathematical notation defines a score for a particular individual or population. In various embodiments, the following definitions apply to various embodiments described herein.

Definitions n=nutritional consumable.
c=measurable component.
t=time period (e.g., t=30 min, t=1 day, t=1 year).
$A_{nt}$=amount (grams) of nutritional consumable n measured over time period t.
$\delta_{cn}$=density of measurable component c in nutritional consumable n=amount (grams) of measurable component c per gram of nutritional consumable n (e.g., the nutrient weight density).
$A_{cnt}=A_{nt}\delta_{cn}$=amount (grams) of measurable component c consumed in nutritional consumable n over time period t.
$l_{ct}$=lower healthy range for measurable component c over time period t.
$u_{ct}$=upper healthy range for measurable component c over time period t.
$r_{ct}$=tolerance of measurable component c over time period t. The tolerance, in the illustrated embodiment, is defined as the number of times above UHR when the $h_c$-score is equal to 0. In other words, if $r_{ct}$=0.2 then the score will go to zero when $A_{cnt}$ is 20% above the UHR (i.e., when $A_{cnt}$=1.2 $u_{ct}$).
$w_c$=scoring weight of nutritional consumable c. Weights, in the illustrated embodiment, are relative weights; hence their interpretation is relative to other defined weights in the score. For example, $w_a$=2 and $w_b$=4 is exactly the same as $w_a$=1 and $w_b$=2, meaning that "b" will have 2 times the weight on the score as "$_a$".

Equation 11a: MC h-Score $$h_{cnt}(A_{cnt}) = \begin{cases} \dfrac{A_{cnt}}{l_{ct}} & \text{if } A_{cnt} < l_{ct} \\ 1 & \text{if } l_{ct} \leq A_{cnt} \leq u_{ct} \\ \dfrac{(r_{ct}+1)u_{ct} - A_{cnt}}{r_{ct}u_{ct}} & \text{if } A_{cnt} > u_{ct} \end{cases} =$$

general health score of measurable component c in nutritional consumable n over time period t, where $l_{ct} <= u_{ct}$.

Equation 11b: NC H-Score
$H_{nt}(A_{nt})=100*\Sigma_{\forall c}w'_c h_{cnt}(A_{cnt})$=H-score=General nutritional health score of nutritional consumable n over time period t, where, by convention, the defined weights, $w_c$, are normalized as $$w'_c = \frac{w_c}{\Sigma_{\forall c} w_c}.$$

As a result, the score has a maximum score of 100 and weights can be specified in relative terms.

Equation 12a: MC Uhr-Score $$uhr\{0,1\}_{cnt}(A_{cnt}) = \begin{cases} \{0,1\} & \text{if } A_{cnt} < l_{ct} \\ 1 & \text{if } l_{ct} \leq A_{cnt} \leq u_{ct} \\ \dfrac{(r_{ct}+1)u_{ct} - A_{cnt}}{r_{ct}u_{ct}} & \text{if } A_{cnt} > u_{ct} \end{cases}.$$

Equation 12b: NC UHR-Score
$UHR\{0,1\}_{nt}(A_{nt})=100*\Sigma_{\forall c}w'_c uhr\{0,1\}_{cnt}(A_{cnt})$, where $UHR\{0,1\}$ is the upper healthy range score. Also referred to as the UHR0 or UHR1 score. Note UHR{0, 1} is simply the H-score setting all LHR scores to 0 or 1.

Equation 13a: MC Lhr-Score $$lhr\{0,1\}_{cnt}(A_{cnt}) = \begin{cases} \dfrac{A_{cnt}}{l_{ct}} & \text{if } A_{cnt} < l_{ct} \\ 1 & \text{if } l_{ct} \leq A_{cnt} \leq u_{ct} \\ \{0,1\} & \text{if } A_{cnt} > u_{ct} \end{cases}.$$

Equation 13b: NC LHR-Score
$LHR\{0,1\}_{nt}(A_{nt})=100*\Sigma_{\forall c}w'_c lhr\{0,1\}_{cnt}(A_{cnt})$, where $LHR\{0,1\}$ is the lower healthy range score. This may also be referred to as the LHR0 or LHR1 score. Note that $LHR\{0,1\}$ is simply the H-score setting all UHR scores to 0 or 1.

Invariant Scoring Positions
$Hmax=max_{\forall A_{nt}} H_{nt}(A_{nt})$=in one embodiment, this represents the maximum H-score attainable across all amounts.
$Hx=H_{nt}(A_{nt})@min(A_{nt})$ s.t. UHR1<100=H-score at the amount when the first upper healthy range u is crossed for any measurable component c.

The use of UHR1/LHR1 may be more appropriate when analyzing/visualizing nutritional components scored at a fixed amount (i.e. 100 kcal, 100 g), since UHR1/LHR1 describe the proportion of the NC over or under UHRs and LHRs at some amount. The use of UHR0/LHR0 may be more appropriate when analyzing/visualizing nutritional components when scored at Hmax or Hx, since UHR0/LHR0 describe the relative magnitude of UHR and LHR scores independent of the contribution of other components.

In one embodiment, a NHF score is an H-score that is fully determined by a selection of MCs with corresponding weight, tolerance, LHR, and UHR defined for each MC. The definition of a NHF score in this embodiment is separated into scoring profiles and healthy range profiles to further improve utility in various embodiments.

In one embodiment, a scoring profile defines only the MCs, weights, and tolerances. In one embodiment, a healthy range profile defines the LHR and UHR for each MC.

By separating scoring profiles and healthy range profiles, the systems and method disclosed herein enable combinatorial use of a single scoring profile with multiple healthy range profiles, and multiple scoring profiles with a single healthy range profile. The combinatorial use of scoring profiles and health range profiles in these embodiments may be particularly useful when scoring nutrient intakes for heterogeneous populations with different target goals/measures. In embodiments of the disclosed system, all available MCs defined in food databases may be included along with Daily Recommended Intake (DRI) values given by the Institute of Medicine (IOM). In these embodiments, LHR values are set to RDA values and UHR values are set to ULs based on age and gender of each individual, or to a range if specified as such.

In the unique and special case of an H-score definition where all weights and tolerances are set to 1, then 100 minus the H-score (Equation 11b above) can be interpreted as "the average percentage outside healthy ranges of measurable components in the nutritional consumable." In other words, the H-score in this embodiment depicts "on average how far outside healthy ranges" is the NC as a function of amount. This NHF "A" (for average) scoring profile is a special case and its distinct interpretation should be of great benefit to the nutrition community for interpretability and simplicity.

For the validation of the NHF, embodiments of the disclosed system relied on data from the National Health and Nutrition Examination Survey (NHANES) 2011-2012. Respondents in the age range 12 to 79 were selected to create a comprehensive data set with clinical measurements. The NHANES study collected two independent 24 hr dietary recalls for all participants. The first 24 hr recall was conducted in person and the second by phone 3 to 10 days later. A respondent was included for analysis when two dietary 24 hr recalls and the clinical measures for height, weight, BMI, glycohemoglobin %, and HDL cholesterol were reported. Respondents who reported more than 8000 kcal of intake on either dietary recall was excluded to limit extreme outliers. These inclusion criteria identified 4639 respondents in NHANES whose data were subsequently used for analysis. Dietary data of the two 24 hour recalls was averaged for each participant.

Healthy range profiles were created for all DRI gender/age combinations of males and females between 12 and 79 to use for the analyses. For MCs with energy dependent healthy ranges, the IOM defined Expected Energy Requirements (EER) was computed for each respondent given their age, gender, height and weight. The target healthy range for energy was set to +/−5% of the EER. All target macronutrient (MC's) DRI healthy ranges were defined as the % of EER. Total sugar is the only MC that does not have an explicit DRI value given by the IOM. The DRI of <25% of energy consumption of added sugars was used as the UHR for total sugars which is a conservative bound since total sugars include added sugars.

The comparison of both HEI-2010 scores and nutrient profiling scores required a single dietary data set with both food components (for HEI) as well as nutrients based on the NHANES dietary data. Each food item in the NHANES 2011-2012 24 hr recall corresponds to a single food item in the Food and Nutrient Database for Dietary Studies (FNDDS) 2011-2012. The FNDDS contains the nutrient density information for dozens of nutrients, but does not contain the food components used to compute HEI scores. The Food Patterns Equivalents Database (FPED) 2011-2012 provided the corresponding food components for each food item in the FNDDS 2011-2012. The FNDDS and FPED databases were merged into a single master food database then individual food items in each 24 hr recall were consolidated into a 24 hr diet for every respondent. The final dataset included dietary and clinical data for each respondent.

In one embodiment of the system and methods disclosed herein, a general and powerful data driven methodology was used to design NHF scores that may be maximally predictive of clinical measures of healthfulness. Specifically, a form of Sequential Quadratic Programming (SQP) optimized the sum of correlations between the H-score (equation 11b) and any set of other measurements. The advantage of SQP is its ability to solve constrained non-linear optimization problems. The single function fmin_slsqp was implemented in the open-source Python SciPy optimization package. The optimization is a formal mathematical method that changes parameters (weights and tolerances) in an existing score to maximize the correlation of (in this case) the H-score (scored on respondent dietary data) with clinical measures. SQP was utilized to constrain the final weights (0 to 50) and tolerances (0.2 to 100). The function, f(x), that was optimized is the sum of output correlations between the H-score and other measures stated as:

$f(x) = \Sigma_{\forall M}$ corr(H(x),M), where corr( ) is the Pearson correlation function, H( ) is the set of H-scores produced for dietary data of all respondents, M is a set of measurements (e.g., BMI or HEI scores) on the same set of respondents, and x is a vector of weights and tolerances defining the H-score output.

By maximizing the sum of correlations, a single measure M or to multiple measures M can be optimized simultaneously. In this particular case, the LHR and UHR values are constant for each respondent, but in practice they could be included in x and optimized simultaneously. After each optimization, the extremely small MC weights ($<\frac{1}{50}^{th}$ of the largest weight) are set to zero since they will not contribute to the H-score's correlation. This process simultaneously selects MCs and optimizes weights. The final weights are normalized by the smallest remaining weight, which results in the smallest weight in a H-score design to be 1.

NHF scores generated using the disclosed system and methods were validated by measuring the correlation (r) and explained variance ($R^2$%) between a NHF score produced on respondent dietary data and respondent measures of BMI, glycohemoglobin %, and HDL cholesterol. For purposes of comparison with existing tools, validation measures were computed with HEI-2010 dietary scores. As a further validation of the NHF as a nutrient profiling tool, all foods in the FNDDS database were scored and plotted to visualize food ranking. The NHF H-scores of FNDDS foods were also compared to the same foods with the Nutrient Rich Foods Index (NRF9.3) profiling nutrients at 100 kcal.

Two NHF scoring profiles were created manually for analysis and comparison: NHF DRI, and NHF HEI. The remaining scoring profiles were all derived through data driven parameter optimization from the NHF DRI. NHF DRI was defined with the NHF "A" definition above. NHF HEI was defined with MCs and healthy ranges selected to minimize changes to the existing HEI-2010 DQI. The supplementary information provided herewith further discusses these results.

Specifically, the data and code used to generate the data referred to above is provided as supplementary Appendix A hereto. Using this data and code, results can be generated with fully open-source software (Python) and be executed with a single command by any researcher.

Results generated according to the discussion above (including using the data and code provided in Appendix A hereto) are described in more detail below and with reference to the following Table 1 and Table 2.

Table 1 below shows the set of the NHF scoring profiles and a subset of healthy range profiles created and used in this study. In the embodiment illustrated in Table 1, scoring profiles are defined by non-zero weights and tolerances. The MCs that were selected during the optimization and the magnitude of their weights and tolerances are provided for the optimized profiles "DRI_2_...". Tolerances that remain at a value of 1 after optimization are largely due to a configuration when a change in the tolerance value causes minimal/no change in the H-score for the particular MC. Two primary causes explain this behavior: (i) the UHR is infinite (does not exist), or (ii) most or all respondent data are below the UHR.

TABLE 1

Scoring profiles/healthy ranges to generate results.

| measurable component (MC)[3] | Units | Scoring Profiles | | | | |
|---|---|---|---|---|---|---|
| | | NHF DRI | NHF DRI_2_BMI | NHF DRI_2_Glyco | NHF DRI_2_HDL | NHF DRI_2_BGH |
| | | | | weight (tolerance) | | |
| 18:2 | % eer/d | 1 (1.0) | 4 (0.2) | | | 7 (0.2) |
| 18:3 | % eer/d | 1 (1.0) | | | | |
| Calcium | mg/d | 1 (1.0) | | 8 (2.6) | | |
| Carbohydrate | % eer/d | 1 (1.0) | | | | |
| Carotene, alpha | ug/d | 1 (1.0) | 4 (1.0) | 1 (1.0) | 3 (1.0) | 10 (1.0) |
| Carotene, beta | ug/d | 1 (1.0) | | | 6 (1.0) | |
| Cholesterol | mg/d | 1 (1.0) | 7 (1.0) | 4 (0.7) | 6 (0.7) | 16 (0.7) |
| Choline, total | mg/d | 1 (1.0) | | | 11 (1.0) | |
| Copper | mg/d | 1 (1.0) | | | | |
| Cryptoxanthin, beta | ug/d | 1 (1.0) | 2 (1.0) | 1 (1.0) | 3 (1.0) | 3 (1.0) |
| Energy | % eer/d | 1 (1.0) | | | | |
| Fatty acids, total saturated | % eer/d | 1 (1.0) | 9 (1.7) | | 11 (2.6) | 20 (2.0) |
| Fiber, total dietary | g/d | 1 (1.0) | | | 8 (1.0) | |
| Folate, total | ug/d | 1 (1.0) | 1 (4.7) | | | |
| Folic acid | ug/d | 1 (1.0) | 17 (7.7) | 11 (5.1) | | 15 (5.6) |
| Iron | mg/d | 1 (1.0) | | | | |
| Magnesium | mg/d | 1 (1.0) | | 3 (1.8) | 7 (0.2) | 44 (2.8) |
| Niacin | mg/d | 1 (1.0) | | | | |
| Phosphorus | mg/d | 1 (1.0) | | | | |
| Potassium | mg/d | 1 (1.0) | | | | |
| Protein | % eer/d | 1 (1.0) | | | | |
| Riboflavin | mg/d | 1 (1.0) | | | | |
| Selenium | ug/d | 1 (1.0) | | | | |
| Sodium | mg/d | 1 (1.0) | | 4 (0.2) | | |
| Sugars, total | % eer/d | 1 (1.0) | | | 8 (0.6) | |
| Thiamin | mg/d | 1 (1.0) | | | | |
| Total Fat | % eer/d | 1 (1.0) | | 3 (0.2) | | 1 (0.2) |
| Vitamin A, RAE | ug/d | 1 (1.0) | | | 1 (0.2) | |
| Vitamin B-12 | ug/d | 1 (1.0) | | | | |
| Vitamin B-6 | mg/d | 1 (1.0) | | 8 (1.0) | | |
| Vitamin C | mg/d | 1 (1.0) | 5 (1.0) | 2 (1.0) | | 8 (1.0) |
| Vitamin D (D2 + D3) | ug/d | 1 (1.0) | 12 (1.0) | | | 1 (1.0) |
| Vitamin E (alpha-tocopherol) | mg/d | 1 (1.0) | 21 (1.0) | 5 (1.0) | | 9 (1.0) |
| Vitamin K (phylloquinone) | ug/d | 1 (1.0) | 6 (1.0) | 1 (1.0) | 21 (1.0) | 39 (1.0) |
| Water | ml/d | 1 (1.0) | | | | |
| Zinc | mg/d | 1 (1.0) | | | | |
| D_TOTAL | cup_eq | | | | | |
| EMPTY_CALORIES | sum | | | | | |
| FA_RATIO | ratio | | | | | |
| F_TOTAL | cup_eq | | | | | |
| GREENS_AND_BEANS | cup_eq | | | | | |
| G_REFINED | oz_eq | | | | | |
| G_WHOLE | oz_eq | | | | | |
| SEA_PLANT_PROT | oz_eq | | | | | |
| TOT_PROT_FOODS | oz_eq | | | | | |
| TOT_VEG | cup_eq | | | | | |
| WHOLE_FRUIT | cup_eq | | | | | |

TABLE 1-continued

Scoring profiles/healthy ranges to generate results.

| measurable component (MC)[3] | Scoring Profiles | | Healthy Range Profiles | | |
|---|---|---|---|---|---|
| | NHF DRI_2_HEI weight (tolerance) | NHF HEI | Female 31-50 | Male 9-13 LHR (UHR) | NHF HEI |
| 18:2 | | | 5 (10) | 5 (10) | ( ) |
| 18:3 | | | 0 (1) | 0 (1) | ( ) |
| Calcium | | | 1000 (2500) | 1300 (3000) | ( ) |
| Carbohydrate | | | 45 (65) | 45 (65) | ( ) |
| Carotene, alpha | 2 (1.0) | | 16800 ( ) | 14400 ( ) | ( ) |
| Carotene, beta | 5 (1.0) | | 8400 ( ) | 7200 ( ) | ( ) |
| Cholesterol | | | 0 (300) | 0 (300) | ( ) |
| Choline, total | 1 (1.0) | | 425 (3500) | 375 (2000) | ( ) |
| Copper | | | 0 (10) | 0 (5) | ( ) |
| Cryptoxanthin, beta | 5 (1.0) | | 16800 ( ) | 14400 ( ) | ( ) |
| Energy | | | 95 (105) | 95 (105) | ( ) |
| Fatty acids, total saturated | 18 (1.2) | | 0 (7) | 0 (7) | ( ) |
| Fiber, total dietary | 35 (1.0) | | 25 ( ) | 31 ( ) | ( ) |
| Folate, total | | | 400 (1000) | 300 (600) | ( ) |
| Folic acid | | | 240 (600) | 180 (360) | ( ) |
| Iron | | | 18 (45) | 8 (40) | ( ) |
| Magnesium | 1 (2.1) | | 320 (670) | 240 (590) | ( ) |
| Niacin | | | 14 ( ) | 12 ( ) | ( ) |
| Phosphorus | | | 700 (4000) | 1250 (4000) | ( ) |
| Potassium | 29 (1.0) | | 4700 ( ) | 4500 ( ) | ( ) |
| Protein | | | 10 (35) | 10 (30) | ( ) |
| Riboflavin | | | 1 ( ) | 0 ( ) | ( ) |
| Selenium | | | 55 (400) | 40 (280) | ( ) |
| Sodium | | 2 (1.8) | 1500 (2300) | 1500 (2200) | 0 (1100) |
| Sugars, total | 8 (0.6) | | 0 (25) | 0 (25) | ( ) |
| Thiamin | | | 1 ( ) | 0 ( ) | ( ) |
| Total Fat | | | 20 (35) | 25 (35) | ( ) |
| Vitamin A, RAE | | | 700 (3000) | 600 (1700) | ( ) |
| Vitamin B-12 | | | 2 ( ) | 1 ( ) | ( ) |
| Vitamin B-6 | | | 1 (100) | 1 (60) | ( ) |
| Vitamin C | 5 (1.0) | | 75 (2000) | 45 (1200) | ( ) |
| Vitamin D (D2 + D3) | 11 (1.0) | | 15 (100) | 15 (100) | ( ) |
| Vitamin E (alpha-tocopherol) | 1 (1.0) | | 15 (1000) | 11 (600) | ( ) |
| Vitamin K (phylloquinone) | 6 (1.0) | | 90 ( ) | 60 ( ) | ( ) |
| Water | | | 2700 ( ) | 2400 ( ) | ( ) |
| Zinc | | | 8 (40) | 8 (23) | ( ) |
| D_TOTAL | | 2 (1.0) | 1 ( ) | 1 ( ) | 1 ( ) |
| EMPTY_CALORIES | | 4 (2.6) | 0 (19) | 0 (19) | 0 (19) |
| FA_RATIO | | 2 (1.0) | 2 ( ) | 2 ( ) | 2 ( ) |
| F_TOTAL | | 1 (1.0) | 0 ( ) | 0 ( ) | 0 ( ) |
| GREENS_AND_BEANS | | 1 (1.0) | 0 ( ) | 0 ( ) | 0 ( ) |
| G_REFINED | | 2 (2.4) | 0 (1) | 0 (1) | 0 (1) |
| G_WHOLE | | 2 (1.0) | 1 ( ) | 1 ( ) | 1 ( ) |
| SEA_PLANT_PROT | | 1 (1.0) | 0 ( ) | 0 ( ) | 0 ( ) |
| TOT_PROT_FOODS | | 1 (1.0) | 2 ( ) | 2 ( ) | 2 ( ) |
| TOT_VEG | | 1 (1.0) | 1 ( ) | 1 ( ) | 1 ( ) |
| WHOLE_FRUIT | | 1 (1.0) | 0 ( ) | 0 ( ) | 0 |

In Table 1 above, scoring profiles consist of a set of non-zero weight MCs with tolerance. NHF DRI and NHF HEI were constructed by hand. All other profiles were derived in an optimization from NHF DRI. Also in the above table, an undefined (blank) LHR is assumed to be 0 and an undefined UHR is assumed to be infinity. Only two DRI healthy range profiles are shown, where the complete set of healthy range profiles discussed herein are provided in Appendix A hereto. In the above table, measurable components include all nutrients/food components from the intersection of FNDDS/FPED databases that have defined healthy ranges as DRI or HEI values.

Figure 12A:
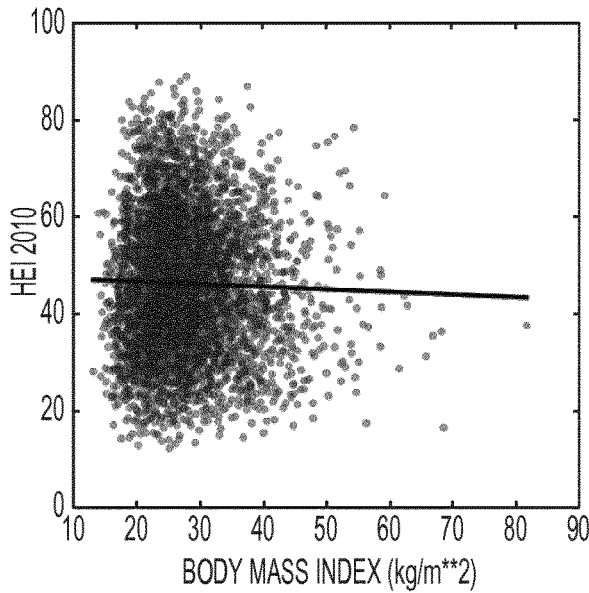
FIG. 12 hereto illustrates correlation and linear fit of scores in various embodiments of the disclosed system with the clinical health measure Body Mass Index ("BMI") in the National Health and Nutrition Examination Survey ("NHANES") data.
Figure 12B:
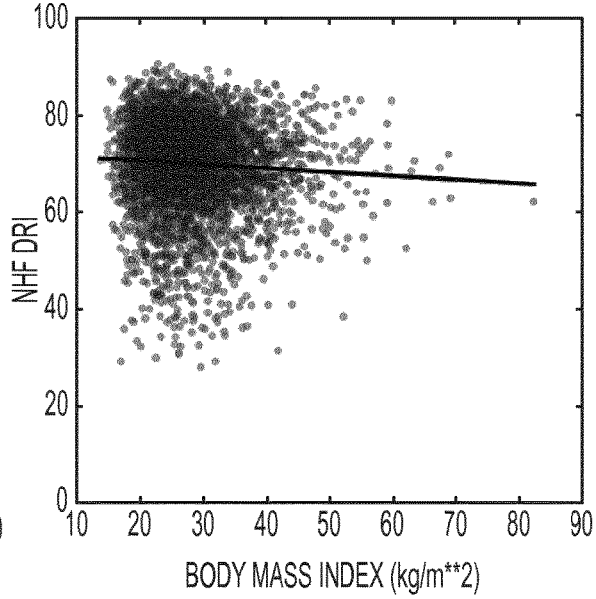
Figure 12C:
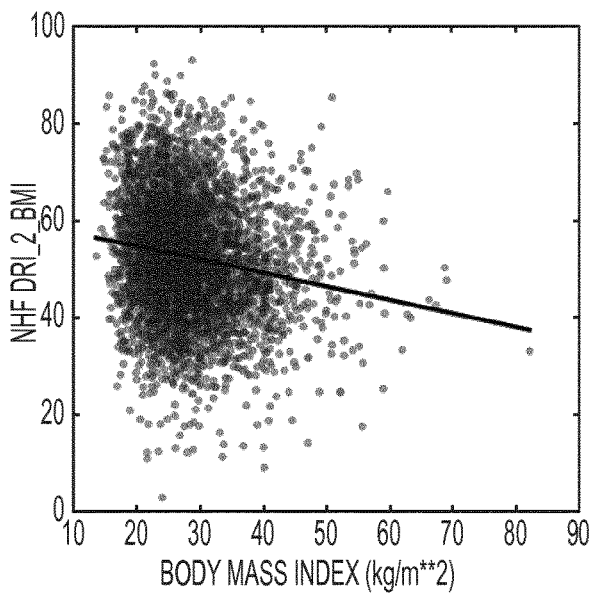
Figure 12D:
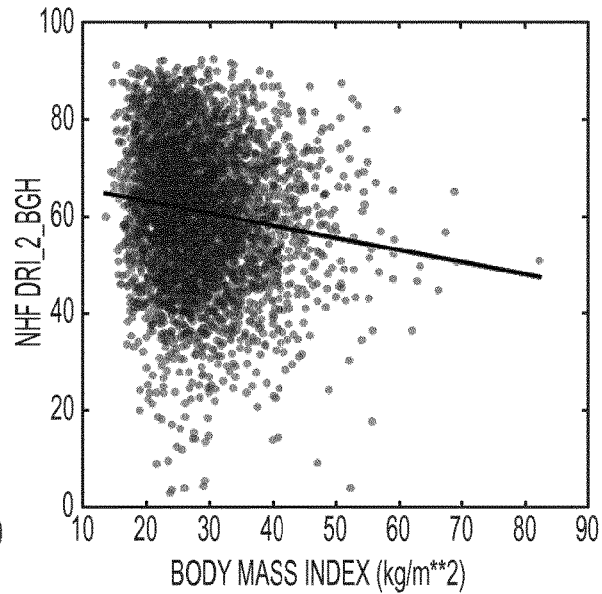

FIG. 12 hereto illustrates a plurality of scatter plots showing examples of the measured correlation of various dietary scoring methods with BMI for respondents using HEI-2010 (FIG. 12(a)) or NHF DRI scores (FIG. 12(b)). Both the HEI-2010 and NHF DRI have minimal (r<−0.06) correlation with BMI explaining <0.3% of the variance. The optimization of NHF DRI score with BMI yields the NHF DRI_2_BMI score (FIG. 12(c)). The improved NHF DRI_2_BMI explains 2.6% of the variance (8 fold increase from 0.3% in nonoptimized score) in respondent BMI from dietary data alone. FIG. 12(d) shows the correlation with BMI of the NHF DRI_2_BGH score that was simultaneously optimized to three clinical measures (BMI, glycohemoglobin %, HDL). The explained variance drops to 1.6% (5 fold increase from 0.3% in nonoptimized score). The decrease of the correlation with BMI alone is a result of the need for NHF DRI_2_BGH to also correlate simultaneously with glycohemoglobin and HDL. While the correlations and explained variances are small, the analysis demonstrated that the optimization works to improve predictive power on BMI. The same analysis was performed on all clinical variables.

Table 2 below shows a matrix of the explained variance between all scores and all clinical health measures. The higher the variance explained, the more highly correlated are the values, which also gives a measure of similarity when comparing different scores. The NHF score that best explains variance for any individual clinical measure occurs when optimized to the single clinical measure. NHF DRI_2_Glyco explained 1.2% of glycohemoglobin (12 fold increase) and NHF DRI_2_HDL explained 2.6% of HDL cholesterol (13 fold increase). The NHF DRI_2_BGH is the only score to explain >0.5% variance of all three clinical health measures (average 6 fold increase), which demonstrated that the optimization improves predictive power across all three clinical health measures simultaneously.

dietary fiber/total sugars (only in DRI_2_HDL). These results are (of course) affected by the set point of healthy ranges which impacted the optimization and thus selection of MCs and parameters. For example, if the healthy range for a MC spans the intake measurement for all the participants, then that MC will not distinguish variance between respondent dietary data scores and clinical measures. Therefore, that MC will be dropped by the optimization. Improvement of experimental data for determining healthy ranges is a beneficial topic for future research.

TABLE 2

NHANES dietary scoring $R^{2\%}$ matrix between all dietary scores and clinical health measures

| | NHF DRI | NHF DRI_2_BMI | NHF DRI_2_Glyco | NHF DRI_2_HDL | NHF DRI_2_BGH | NHF DRI_2_HEI |
|---|---|---|---|---|---|---|
| NHF DRI | 100 | 59.6 | 56.6 | 44.9 | 57.8 | 47 |
| NHF DRI_2_BMI | 59.6 | 100 | 70.6 | 28.3 | 69.2 | 34.6 |
| NHF DRI_2_Glyco | 56.6 | 70.6 | 100 | 18.8 | 58 | 22.8 |
| NHF DRI_2_HDL | 44.9 | 28.3 | 18.8 | 100 | 62.1 | 63.2 |
| NHF DRI_2_BGH | 57.8 | 69.2 | 58 | 62.1 | 100 | 50.3 |
| NHF DRI_2_HEI | 47 | 34.6 | 22.8 | 63.2 | 50.3 | 100 |
| NHF HEI | 18.2 | 10.3 | 6 | 31.6 | 21.1 | 53.9 |
| HEI 2010 | 15 | 8.5 | 3 | 34 | 19.4 | 56 |
| Body Mass Index (kg/m**2) | 0.3 | 2.6 | 1.1 | 0.3 | 1.6 | 0.3 |
| Glycohemoglobin (%) | 0.1 | 0.8 | 1.2 | 0 | 0.7 | 0 |
| Direct HDL-Cholesterol (mg/dL) | 0.2 | 0 | 0 | 2.6 | 1.2 | 0.8 |

| | NHF HEI | HEI 2010 | Body Mass Index (kg/m**2) | Glycohemoglobin (%) | Direct HDL-Cholesterol (mg/dL) |
|---|---|---|---|---|---|
| NHF DRI | 18.2 | 15 | 0.3 | 0.1 | 0.2 |
| NHF DRI_2_BMI | 10.3 | 8.5 | 2.6 | 0.8 | 0 |
| NHF DRI_2_Glyco | 6 | 3 | 1.1 | 1.2 | 0 |
| NHF DRI_2_HDL | 31.6 | 34 | 0.3 | 0 | 2.6 |
| NHF DRI_2_BGH | 21.1 | 19.4 | 1.6 | 0.7 | 1.2 |
| NHF DRI_2_HEI | 53.9 | 56 | 0.3 | 0 | 0.8 |
| NHF HEI | 100 | 92.6 | 0.1 | 0.1 | 1.4 |
| HEI 2010 | 92.6 | 100 | 0.1 | 0.2 | 1.6 |
| Body Mass Index (kg/m**2) | 0.1 | 0.1 | 100 | 5.6 | 7.4 |
| Glycohemoglobin (%) | 0.1 | 0.2 | 5.6 | 100 | 2.3 |
| Direct HDL-Cholesterol (mg/dL) | 1.4 | 1.6 | 7.4 | 2.3 | 100 |

In the above table, R2% percentage of variance is explained by a linear fit between different scores produced by scoring the 4639 respondents in NHANES data.

Since optimization selects MCs that are most useful in predicting clinical health measures, the MCs identified by optimization provide information between nutrients and specific health measures. For example, the NHF DRI_2_BMI score is composed of 11 MCs (from the original 36 in the NHF DRI—Table 1). The NHF DRI_2_Glyco score has 12 MCs, while NHF DRI_2_HDL had 11 MCs. The combined optimization NHF DRI_2_BGH is composed of 12 MCs. Only 4 MCs were selected by the optimization in these four overall scores: alpha-carotene, dietary cholesterol, beta-cryptoxanthin, and vitamin K. Given the fixed LHR/UHR values, these 4 MCs were more predictive as dietary markers simultaneously across the three clinical measures than any of the other 36. Another 5 nutrients were selected by DRI_2_BGH but were left out in one scoring profile: magnesium (not in DRI_2_BMI), saturated fat (not in DRI_2_Glyco), folic acid/vitamin E/vitamin C (not in DRI_2_HDL). That is, these MCs are selected as most predictive by 2 of the 3 clinical health measures. Alternately, nutrients are selected only for a particular clinical measure but not optimized in the 3 other scores: total folate (only in DRI_2_BMI), calcium/sodium (only in DRI_2_Glyco), The correlation of developed nutrient profiling tools with HEI scores has been found to be usable as a typical validation of nutrient profiling systems. The NHF DRI_2_HEI score maximized correlation with HEI-scores directly for comparison to this past research. The NHF DRI_2_HEI explained 56% of the variance in HEI scores on the dietary data (Table 2). Others showed that NRF9.3 explained 44.5% of the HEI and the highest best-fit method explained 65%. To further explore the explanatory power of the NHF to HEI scores, manual minor adjustment of some LHR/UHR values (e.g., total sugar) resulted in explanation of >60% of the variance in HEI scores after optimization. LHR/UHR value selection is therefore important in the final variance explained by any model toward any measure, which could be a direction for future research. The difference between HEI scores and other scores is largely due to the saturation that occurs when calculating HEI scores. The HEI saturation functions in FIG. 11(b) limit the variance explainable by nutrient profiling tools that utilize unbounded functions as in FIGS. 11(a) and 11(c).

In one embodiment, the disclosed system and methods were used to create an NHF HEI score to assess the transferability of other methods into the NHF. (Table 1). The NHF HEI score utilized the same food components as defined in the HEI with weights, tolerances, and healthy ranges converted from the HEI-2010 specification, but retain the NHF scoring function. Weights were normalized to the minimum weight since weights are relative in the NHF. As an example of converting HEI-2010 specifications to ranges and tolerances, the HEI sodium range of 1.1 g/1000 kcal (max score) to 2.0 g/1000 kcal (min score) was converted into a UHR=1.1 g and a tolerance of 2.0/1.1=1.8, with LHR=0. By definition, the MC score for sodium will be maximum at 1.1 g and be zero at 2.0 g just as in the HEI-2010, but will continue to decrease after 2.0 g in the NHF HEI in contrast to the HEI scoring method. The NHF HEI score was analyzed at 1000 kcal to match with the LHR/UHR specification at 1000 kcal. NHF HEI explains 92.6% of the variance of HEI-2010 scores on NHANES data (Table 2). Therefore, the NHF scoring function can be utilized with existing HEI-2010 parameters with minimal alterations and provide nearly the same metric with all benefits of the NHF scoring function.

A final optimization was done starting from a new scoring profile defined as the intersection of NHF DRI and NHF HEI scoring profiles. This profile was then optimized to HEI scores and explained 98.4% of HEI variance. Interestingly the optimization selected all HEI components as well as 4 nutrients previously identified (alpha-carotene, beta-cryptoxanthin, total saturated fat, and potassium—see supplementary material for tables). These 4 nutrients provided the 6% increase in variance explained by HEI, adding to the evidence that alpha-carotene and beta-cryptoxanthin may be important nutrients to include in measuring a healthful diet.

NHF score DRI_2_BGH was tested for its ability to produce invariant scores as a nutrient profiling model independent of the metric of measurement (grams or kcals). The DRI_2_BGH H-score for 5 NCs is shown as a function of amount in both grams in FIG. 13(a) and kcals in FIG. 13(b). Each food has a score at all intake amounts. The upper graph shows the score as a function of grams and the lower graph shows the score as a function of kcals. In the illustrated embodiments, the two meaningful invariant scores as functions of amount are marked, where the O represents the Hmax score (maximum attainable score) and the X represents the Hx score (score when first UHR is crossed for any measurable component).

Figure 13A:
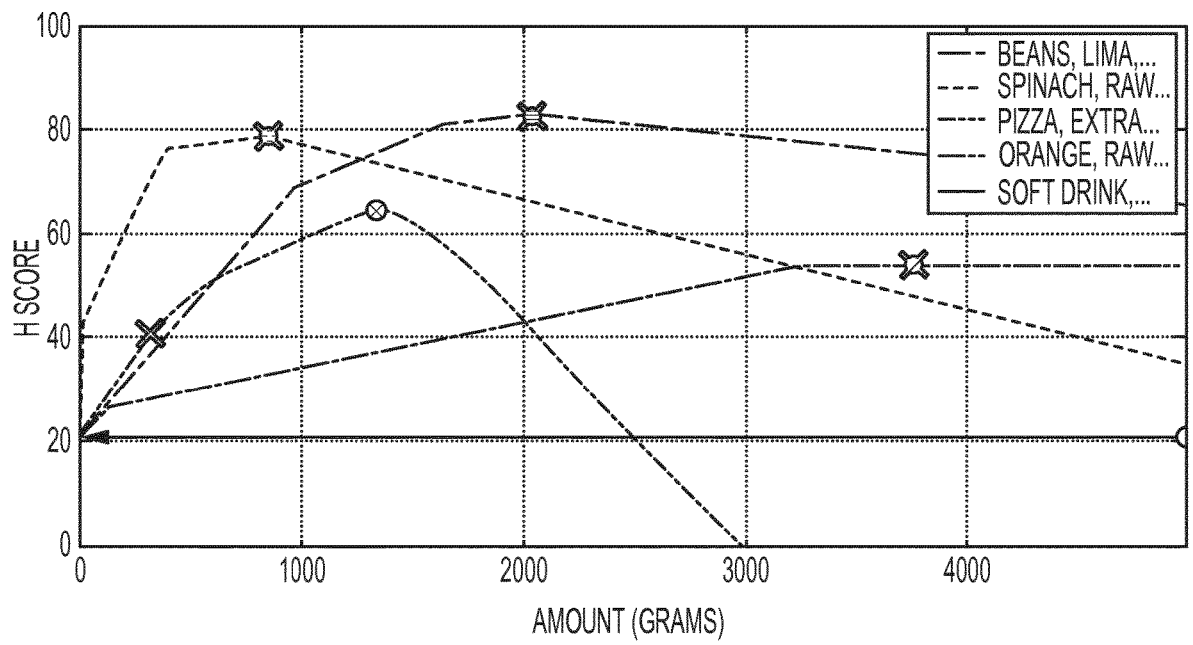
FIG. 13 illustrates set of health scores for 5 foods selected from the FNDDS database in one embodiment of the system disclosed herein.
Figure 13B:
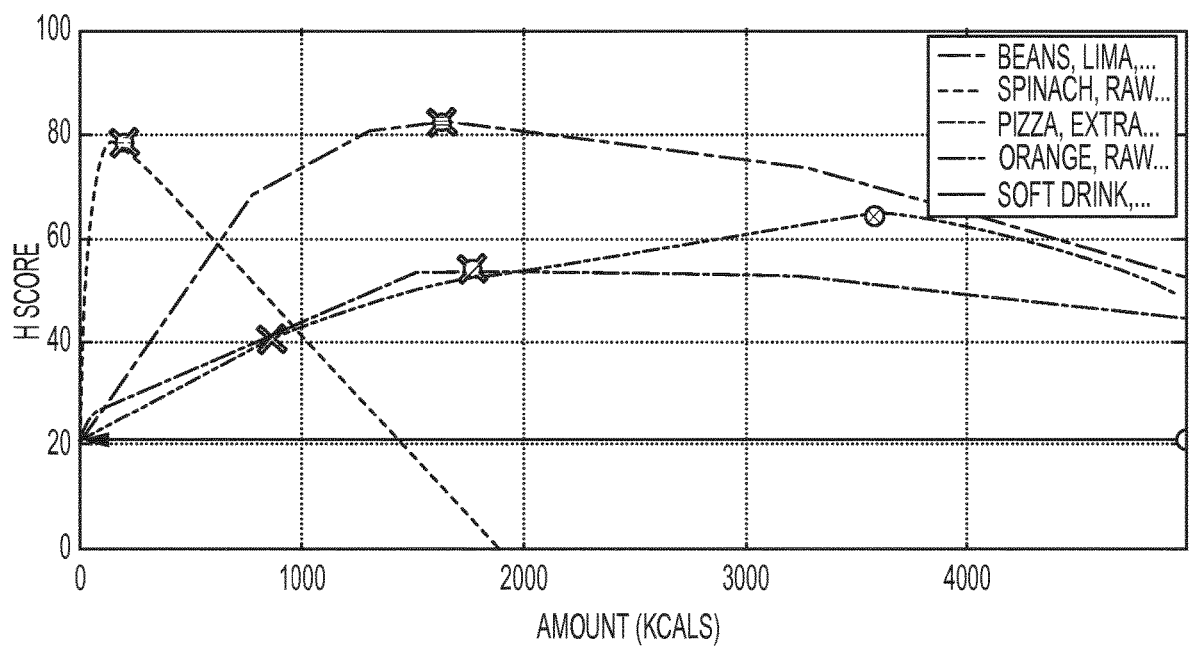

The 5 NCs selected from the FNDDS are: canned low sodium lima beans (75204120), raw spinach (72125100), extra cheese regular crust pizza (58106255), raw orange (61119010), and cola-type soft drink (92410310). All NCs were scored with DRI values from "Female 31-50" demonstrating that foods can be scored toward a specific individual based on individual nutrient needs. Different healthy range profiles will produce different results. The circle "o" marker shows the position of the Hmax score for each NC. The "x" shows the position of the Hx score for each NC. Sometimes these scores overlap and sometimes they do not. The resulting H-score (y-axis value) is identical for Hmax or Hx whether scoring in grams (FIG. 13(a)) or kcals (FIG. 13(b)) and would be for any other metric of amount measured. It should be appreciated that the graphs in FIG. 13 are specific to the definition of DRI_2_BGH. It should be further appreciated that the same foods scored with different NHF scoring profiles will have different curves.

In various embodiments, analyzing graphs in the NHF delivers significantly more information about the nutrient profile of a NC than just the score. For example, in the FIG. 13 embodiment, spinach achieved both Hmax and Hx=78.5 just below 1000 grams and at 200 kcals. These results demonstrated that this food has a higher energy (kcals) nutrient density and a lower weight (grams) nutrient density.

In contrast, pizza reaches Hmax=64.4 at approximately 1300 grams and 3600 kcals, but reaches Hx=41.4 at approximately 400 grams and 900 kcals. Hence, in the embodiment illustrated in FIG. 13, pizza has a higher weight (grams) nutrient density and a lower energy (kcals) nutrient density. In addition, 900 kcals of pizza would be considered the upper limit of a healthful diet that keeps MCs under defined UHRs for Females 31-50. As is also apparent from the embodiment of FIG. 0.13, the shape of food curves and the relationship between Hmax and Hx positions delivers visual information on the balance of positive/negative contribution of nutrients in the food. Sugary cola-type soda received a score slightly above 20 regardless of the amount with the minimum consumption close to 0 for grams or kcals at Hx. Similar analysis can be performed for any food. In addition, the same analysis can be performed for diets or meals as well, because foods, diets and meals are all NCs.

FIG. 14 illustrates a comparison of all FNDDS foods scored by NHF DRI_2_BGH with NRF9.3 100 kcal. In this embodiment, boxplots display average and notched interquartile ranges by food groups as listed in FNDDS database. The boxplots of the FIG. 14 embodiment of all FNDDS foods scored using the NHF DRI_2_BGH where the score given for each food was Hmax (FIG. 14(a)) compared to the same foods scored with NRF9.3 100 kcal (FIG. 14(b)). The boxplot is ordered by food groups in maximum to minimum average value of DRI_2_BGH scores as follows: "vegetables", "fruits", "legumes, nuts, and seeds", "grain products", "milk and milk products", "fats, oils, and salad dressings", "meat, poultry, fish, and mixtures", "sugars, sweets, and beverages", "eggs". In the illustrated embodiment, it is apparent that vegetables score highest with fruits, legumes, and grains with average scores above 59. A drop occurs to the milk group, but the milk group's interquartile range is still well above 60. While the fats and oils have a higher average value than meats, the interquartile range of fats are biased below the average. Sweets follow with an average at 40.9 and eggs are lowest largely due to the inclusion of the cholesterol MC by the optimization. The minimum and maximum range for all scores is between 20 and 100. The NRF9.3 plot in the FIG. 14(b) embodiment have different average score values, detailed as follows: vegetables [132.4], fruits [70.8], sweets [41.3], legumes [30.5], milk [24.8], meat [24.1], grain [20.4], eggs [19.2] and fats [−9.3]. In the illustrated embodiment, the minimum value of any food is −737.4 and the maximum value is 2167.8. For interpretability and display purposes, the scores generated by the DRI_2_BGH in FIG. 14(a) are much clearer and more intuitive.

Figure 15:
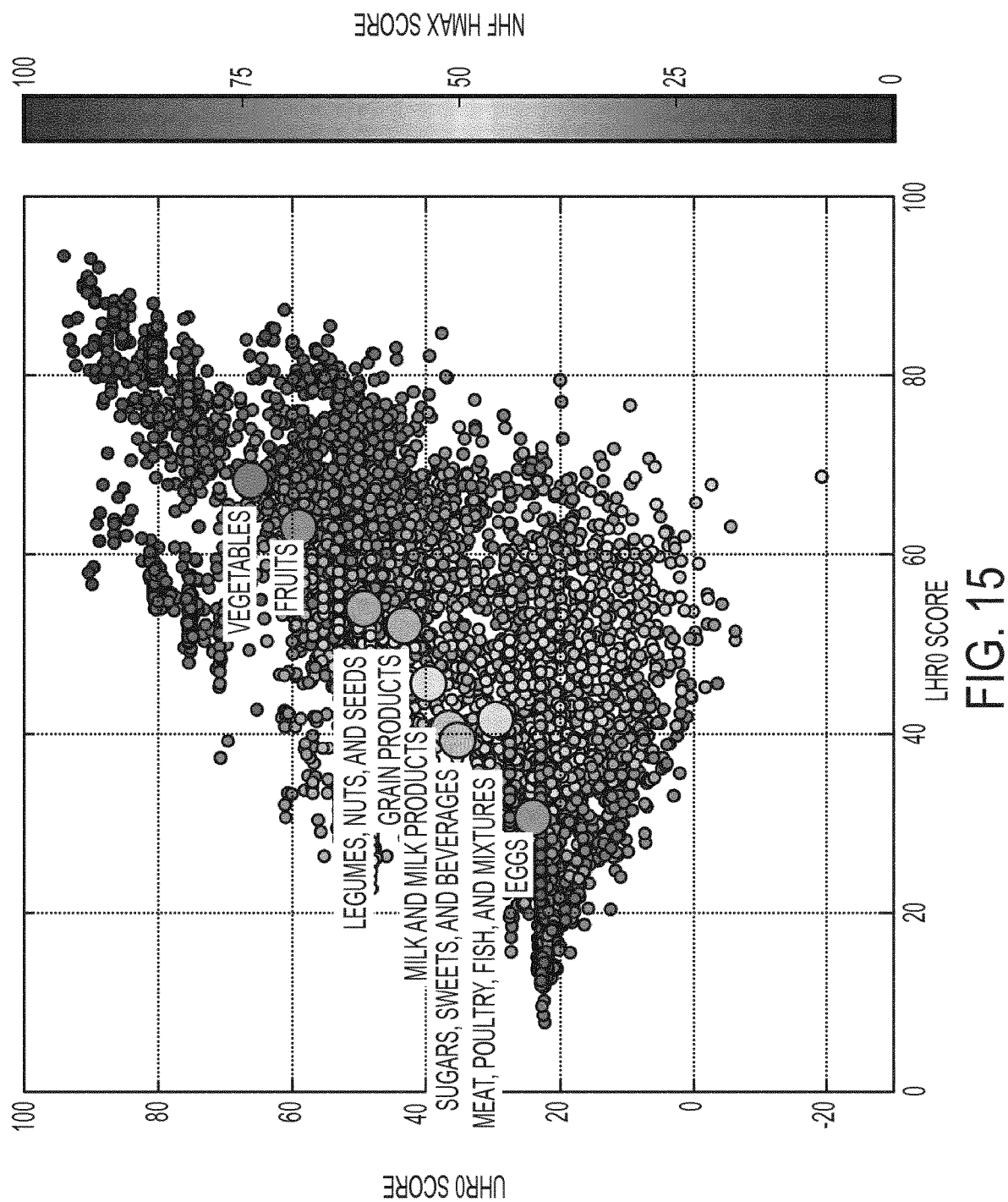
FIG. 15 is a two-dimensional ("2-D") plot of all FNDDS foods scored by one embodiment of the disclosed system.

In a further embodiment, all FNDDS foods from FIG. 14 are re-plotted on a 2-dimensional grid where the color of the food represents the Hmax score in FIG. 15. Specifically, in FIG. 15, the NHF MAX score is plotted using the NHF DRI_2_BGH scoring profile. The average of each food group is plotted and labeled. In this embodiment, foods are plotted along UHR0 and LHR0 axes representing estimates of food composition and balance related to "not too much" (bottom of y-axis) and "not too little" (left side of x-axis) respectively. Average values for each food group are also plotted and labeled. The y-axis represents the UHR0 score for each food, which gives an estimate of the contribution of MCs above UHR to a lower score. The x-axis represents the LHR0 giving an estimate of the contribution of MCs below the LHR to a lower score. A perfectly balanced NC within all defined healthy ranges will be in the upper right corner ("not too much and not too little"). A NC in the upper left quadrant is unlikely to contribute to a poor score by crossing UHRs but will also not contribute to improving the score by pushing MCs above LHR ("not too much, but too little"). A NC in the lower right quadrant contributes to positively covering needs by crossing LHRs, but does so in a way that will also cross many UHRs ("too much, but not too little"). A NC in the lower left quadrant will contribute little positive while significantly going over UHRs ("too much and too little").

Referring now to the embodiments generally illustrated above, and specifically with regard to the embodiments illustrated in FIGS. 11-15, the disclosed system is believed to represent a novel nutritional scoring framework termed the Nutritional Health Framework. The NHF is general in that it can be used as a dietary quality indicator or equally well as a nutrient profiling tool, or as a personalized nutritional scoring system for an individual. The NHF is believed to be the first demonstration of a scoring system designed without subjective opinion in a data driven manner directly on clinical health measures.

As a result of the development of the disclosed systems and methods, several interesting nutrients emerged that provide predictive power toward multiple clinical measures of health using the population level data of the NHANES 24 hour diet intakes and levels of metabolites in the blood. Three of these nutrients were vitamin K, beta-cryptoxanthin and alpha-carotene. These nutrients are not believed to have been included in any previous nutrient profiling systems. Vitamin K is largely found in dark leafy greens and plays a significant role in the binding of calcium ions, impacting bones and tissues and has been linked to long term health. Beta cryptoxanthin, commonly found in egg yolk and orange vegetables, is converted to vitamin A in the body and has been directly linked as a chemopreventative agent against lung cancer. Alpha-carotene, found in yellow and orange vegetables has also been directly inversely associated with multiple risks of death. Vitamin A metabolites (e.g., retinol, cis-retinoic acid, and others) are involved in many different physiological and health processes.

The use of data driven analytic approaches is extremely powerful in removing wide sources of subjective bias that can be introduced in expert defined tools. As a comprehensive framework, the NHF described in various embodiments above is capable of simultaneously addressing multiple existing challenges in the nutritional scoring field:

Nutrients/food components/etc. need not be classified into separate categories of positive or negative: addressed through the use of healthy ranges.

An output score has an intuitive maximum at 100, but still provides for continuous measurement across all diet compositions: addressed through the scoring function shown, for example, in FIG. 11(a).

Dietary scoring parameters can be selected in a purely data driven manner by correlating with arbitrary numbers of clinical measures of health: addressed by using SQP non-linear optimization techniques.

Foods and diets can be meaningfully scored in comparison at different amounts and do not need to be scored at single amounts of nutrient density: addressed through the use of Hmax and Hx invariant scores.

The NHF scores NCs in a general manner so that individual foods, meals, and diets can be analyzed with a single score using the same methods.

Heterogeneous populations can be analyzed in the context of their needs/goals: addressed through the use of scoring profiles and healthy range profiles.

Incremental improvement in meals or diets can be measured and visualized easily: addressed by the visual display of foods moving in a 2-d graph toward the 'optimal' upper right location of FIG. 15 or improvements in dietary curves in FIG. 13.

A concrete definition of general nutritional health can be measured given the validity of LHR and UHR that exist in the literature for each food.

Consumption amount vs. time is addressed explicitly which allows the analysis of the impact of consumption of foods over varying timeframes.

Alternate measures such as the CO2 or financial impact (both MCs with definable healthy ranges for individuals and the environment) of the food/diet can be blended into a single NHF score. The optimization methods can be used on these variables in the same manner as nutrients creating measures of holistic health: addressed by using the general notion of measurable components with healthy ranges.

The inclusion of existing scoring tools into a single framework to enable cross-comparison and to help minimize the diversity of tools in the field.

In addition, development of the disclosed system and methods involved developing multiple scoring profiles that can be immediately used as dietary indicators of clinical health measures. However, in various embodiments the concept of the NHF is that there is not one and only one definition of general nutritional health suitable for all situations and purposes. Rather, the concept of an NHF provides a rigorous framework within which an unlimited number of definitions of GNH can be defined to achieve predefined goals. Hence, the NHF is capable of being adapted and used in different fields and for varying purposes including national nutrition guidelines or for individual personalized nutrition. The adaptability of NHF is believed to be able to impact dietary recommendations for individuals as they progress through different life stages (infant to elderly) with different needs (e.g., diabetics, elite athletes). Since the NHF uses a single robust framework to directly measure and score nutritional intake, it may serve researchers, populations and individuals to improve nutritional health.

Various embodiments discussed above refer or relate to nutritional health scores in the context of scoring nutrients in foods. In the majority of embodiments discussed above, therefore, scores are calculated based on nutrients found in food. In some embodiments, the concept of nutritional health scores is broader, and encompasses not only the impact of a consumable on the health of an individual, but also on the health of the environment. In such embodiments, "nutritional health" can be defined to include both the health of the individual and the health of the planet, and the concepts disclosed herein apply with "measurable features" of the consumable as opposed to "nutrients" of the consumable. For example, measurable features can include features like carbon dioxide emissions associated with creating/consuming the consumable. In one such example, the disclosed system tracks the carbon dioxide emissions per gram of a consumable consumed, and provides a score indicative of that environmental impact. Thus, the disclosed system can provide scores that indicate not only the impact of the consumption of a consumable on an individual's nutritional health, but also on the environment. Moreover, the system can take these environmental impacts into consideration when calculating an overall score, such that consumption of foods that have a relatively high impact on the environment can have lower scores than foods having a relatively low impact on the environment with all nutritional factors being equal.

In various embodiments, the disclosed system may take into account certain "taste" aspects of food when recommending what food to build into a generated diet. For example, if a user indicates he or she would like to have Mexican food for dinner, the system may recommend steak tacos and rice with certain spices to complement the steak tacos. The system in various embodiments also remembers previously recommended foods that the user indicated he or she enjoyed, and tries to recommend foods with similar ingredients or taste profiles. In some embodiments, the system makes recommendations by first trying to select a "main course," such as a chicken breast, and then selecting complementary side items, such as vegetables and rice. In one embodiment, one or more food items are classified by the type of meal they are typically a part of, and recommendations are made based on that classification. For example, scrambled eggs may be classified as a "breakfast" food, and when recommending meals, the system may recommend one or more "breakfast" foods to eat in the mornings.

In one embodiment, the system is configured to integrate with one or more input devices 114 that are personal mobile devices carried by users. For example, a user wearing a pedometer or activity tracker could provide data from those devices to the system, which could adjust the caloric intake range values accordingly. In this way, if a user has a particularly active day, the system may adjust the caloric intake range upward.

In another embodiment, one or more devices carried by the user could provide real-time information to the system when the user is in a food purchasing establishment such as a grocery store or a restaurant. Devices such as RFID readers, NFC readers, wearable camera devices, and mobile phones could receive or determine (such as by scanning RFID tags, reading bar codes, or determining the physical location of a user) foods that are available to a user at a particular grocery store or restaurant. The disclosed system could then make recommendations taking into account what foods could be immediately purchased or consumed by the user. In one such embodiment, when a user sits down at a restaurant, the disclosed system may push information to the user's mobile phone recommending that the user select certain items from the menu to optimize the user's nutritional health score for a given time period.

In one embodiment, the disclosed system enables a user to determine whether or not to eat foods that do not have complete nutrient content data in the stored database. For example, if a particular entry for syrup in the USDA database does not include stored data indicating how much sugar is present in the syrup, in one embodiment the system displays an icon indicating that data is not present in the database for that syrup. Thus, the system enables a user to see, at a glance, if the score being provided by the system is inaccurate based on a clear lack of data. In the syrup example, if the user's sugar nutrient health score is low, the user may know that the lack of data in what the user knows to be a sugar-rich food is causing the score to appear artificially low.

As used herein the term "consumable" is intended to encompass any item consumed by an individual, such as ingredients, foods, meals, or diets.

In some embodiments, the term "nutrient" as used herein refers to compounds having a beneficial effect on the body e.g. to provide energy, growth or health. The term includes organic and inorganic compounds. As used herein the term nutrient may include, for example, macronutrients, micronutrients, essential nutrients, conditionally essential nutrients and phytonutrients. These terms are not necessarily mutually exclusive. For example, certain nutrients may be defined as either a macronutrient or a micronutrient depending on the particular classification system or list. The expression "at least one nutrient" or "one or more nutrients" means, for example, one, two, three, four, five, ten, 20 or more nutrients.

In other embodiments, the term "nutrient" as used herein refers more broadly to any measurable component in a consumable for which a lower healthy range and upper healthy range can be set or otherwise defined to enable the determination of a measure of desired health for the target consumer. In some such embodiments, under this usage of the term "nutrient," the term nutrient can encompass the impact on the environment, cost to produce, difficulty to produce, difficulty to digest, and any other measurable characteristic of food production or consumption.

In various embodiments, the term "macronutrient" is used herein consistent with its well understood usage in the art, which generally encompasses nutrients required in large amounts for the normal growth and development of an organism. Macronutrients in these embodiments may include, but are not limited to, carbohydrates, fats, proteins, amino acids and water. Certain minerals may also be classified as macronutrients, such as calcium, chloride, or sodium.

In various embodiments, the term "micronutrient" is used herein consistent with its well understood usage in the art, which generally encompasses compounds having a beneficial effect on the body, e.g. to provide energy, growth or health, but which are required in only minor or trace amounts. The term in such embodiments may include or encompass both organic and inorganic compounds, e.g. individual amino acids, nucleotides and fatty acids; vitamins, antioxidants, minerals, trace elements, e.g. iodine, and electrolytes, e.g. sodium chloride, and salts thereof.

In various embodiments, the term "essential nutrient" is used herein consistent with its well understood usage in the art, which generally encompasses nutrients that an individual or other subject cannot synthesize endogenously, or cannot synthesize at the level required for good health. For example an essential nutrient may be a nutrient which must be obtained from the subject's diet. An illustrative, non-exhaustive list of essential nutrients includes essential fatty acids, essential amino acids, essential vitamins and essential dietary minerals. In addition, in some embodiments, nutrients may be referred to as "conditionally essential" depending on, for example, whether the subject has a specific disease, condition or genotype.

In various embodiments, the term "general nutritional health" or "GNH" may be used to indicate an expanded focus from the concept of biological healthfulness/health to also include other quantifiable measures not tied specifically to biological health, such as environmental health, financial health, and the like. In such embodiments, the disclosed system and methods provide a scoring system that can generate a provides a scoring measure of GNH. In one such embodiment, the maximum GNH for an entity (individual, population, etc.) exists when every specified measurable component in the nutritional consumable is within a specified healthy range over a specified period of time. In this embodiment, the a measurable component is outside the specified healthy range over the period of time, the further away the entity is from GNH during that period of time.

In various embodiments, the instant disclosure has referenced either databases or datastores as being collections of data. It should be appreciated that depending on the desired implementation, databases (such as databases stored on storage devices operated by the provider of content), datastores (such as cloud computing data storage resources), or other appropriate storage mechanisms could be used to store the various data described herein.

It should be further appreciated that in some embodiments, the amount of food consumed is necessarily determined over a given period of time. For example, a nutritional health score may be one number if a user consumes 1 pound of chicken over the course of a week, and another number altogether if the user consumes 1 pound of chicken in a day. Accordingly, references herein to amounts of food consumed in various embodiments incorporate the concept that the references are to amounts of foods consumed for a given time. Similarly, references to "meals" and "diets" inherently carry with them time period constraints. For example, a meal may be consumed in ⅓ of a day, and a diet may cover a week or a month of time.

As noted above, the disclosed system in some embodiments relies on one or more modules (hardware, software, firmware, or a combination thereof) to perform various functionalities discussed above.

In one such embodiment, a nutritional health score determination system includes a caloric intake range calculation module configured to calculate a caloric intake range for a user by multiplying a standard caloric intake range by a calorie multiplier determined, at least in part, by a characteristic of the user, a consumable input module configured to cause at least one display device to display a consumable entry control to enable the user to specify at least one consumable and at least one amount for said at least one consumable, a nutrient health score calculation module configured to calculate a nutrient health score for each of a plurality of nutrients by determining the value of a piecewise continuous nutrient health score function wherein for each of the plurality of nutrients the nutrient health score function for that nutrient has a first value for a zero amount of that nutrient, and the nutrient health score function for that nutrient has increasing values for amounts of that nutrient greater than zero and less than a lower healthy range value, a constant value for amounts of that nutrient between the lower healthy range value and an upper healthy range value, and decreasing values for amounts of that nutrient greater than the upper healthy range value. In this embodiment, the system also includes a nutritional health score calculation module for calculating a plurality of nutritional health scores based on the nutrient health scores for the plurality of different amounts of at least one of the plurality of nutrients and at least one weighting value, and a user interface display module for causing the at least one display device to display a curve representing the plurality of nutritional health scores for a plurality of amounts of said at least one consumable.

In one further embodiment, the caloric intake range calculation module causes the at least one display device to display an activity input control to enable the user to indicate the characteristic of the user.

In another further embodiment, the system includes an activity monitor, and the caloric intake range calculation module receives data from the activity monitor indicative of the characteristic of the user.

In various further embodiment, the nutrient health score function for at least one of the plurality of nutrients has a value for zero-crossing amounts of said at least one of the plurality of nutrients for which the nutrient health score function is less than the first value, said zero-crossing amounts being based on a sensitivity value for said at least one nutrient of the plurality of nutrients. In one such embodiment, the sensitivity value is inversely related to the user's sensitivity to said at least one nutrient of the plurality of nutrients.

In one further embodiment, the system stores a plurality of tables of weighting values each specific to a particular population of individuals, and the nutritional health score calculation module determines one of the plurality of tables of weighting values to use to calculate the plurality of nutritional health scores based, at least in part, on the characteristic of the user. The characteristic of the user may be selected from the group consisting of: an activity level of the user, an age of the user, a gender of the user, a weight of the user, a Body Mass Index (BMI) of the user, and a medical condition of the user.

In one further embodiment, the system includes a recommendation module configured to operate with the nutritional health score calculation module to determine a plurality of potential nutritional health scores for a plurality of potential consumables and to recommend at least one of the plurality of consumables that results in a highest potential nutritional health score. The recommendation module may be configured to cause the at least one display device to display at least one control to enable the user to add the at least one recommended consumable to a diet. Alternatively, the recommendation module may be configured to cause the at least one display device to display at least one control to enable the user to remove at least a portion of the at least one recommended consumable from a diet.

In one further embodiment, the nutritional health score calculation module is further configured to determine an optimal nutritional health score for a designated set of consumables, and the user interface display module is configured to cause the at least one display device to display an indication of the optimal nutritional health score on the curve representing the plurality of nutritional health scores for the plurality of amounts of said at least one consumable.

In another further embodiment, the nutritional health score calculation module is configured to calculate the plurality of nutritional health scores based on the nutrient health scores for a set containing fewer than all of the nutrients tracked by the disclosed system, said set based on a desired scoring profile for the user.

In one further embodiment, the system displays includes a nutrient subset control that enables the user to indicate a desired subset of nutrients, and the nutritional health score calculation module is configured to calculate the plurality of nutritional health scores based on the nutrient health scores for the desired subset of nutrients.

In another embodiment, the disclosed system includes a nutrient health score calculation module configured to calculate a nutrient health score for each of a plurality of nutrients by determining the value of a piecewise continuous nutrient health score function, wherein for each of the plurality of nutrients, the nutrient health score function is specific to that nutrient, the nutrient health score function for that nutrient has a first value for a zero amount of that nutrient consumed over time, and the nutrient health score function for that nutrient has increasing values for amounts of that nutrient consumed over time greater than zero and less than a lower healthy range value, a constant value for amounts of that nutrient consumed over time between the lower healthy range value and an upper healthy range value, and decreasing values for amounts of that nutrient consumed over time greater than the upper healthy range value. The system in this embodiment also includes a nutritional health score calculation module for calculating a plurality of nutritional health scores for different amounts of nutrients consumed, each nutritional health score based on the nutrient health scores for the plurality nutrients and at least one weighting value and a consumable optimization module configured to determine a set of consumables that contain an amount of calories within a specified caloric intake range, and amounts of nutrients for which the nutritional health score is optimal for said amount of calories within the specified caloric intake range. In this embodiment, the system further includes a user interface display module for causing at least one display device to display a control to enable the user to remove at least one of the consumables from the set of consumables determined by the consumable optimization module.

In a further embodiment, for each of the plurality of nutrients, the nutrient health score function for that nutrient has decreasing values less than the first value for amounts of that nutrient consumed over time exceeding a zero-crossing amount, the zero-crossing amount calculable from a sensitivity value for that nutrient.

In one embodiment, the system includes at least one data storage device to store at least one table containing a plurality of weighting value/sensitivity value pairs for each of a plurality of tracked nutrients. One of the weighting value/sensitivity value pairs may be selected for each of the plurality of tracked nutrients based on a characteristic of the user, which may be at least one selected from the group consisting of: an age, a gender, a height, a weight, a Body Mass Index (BMI), and an activity level.

In one further embodiment, the nutrient health score calculation module and the nutritional health score calculation each calculate scores for consumption over an amount of time.

In another further embodiment, the consumable optimization module selects at least one suggested main meal item before selecting a plurality of complementary consumables to that main meal item.

As noted above, Appendix A hereto contains the necessary data and computer code in one embodiment in order to generate data and re-generate the results discussed herein. In an embodiment, one of the spreadsheets included in Appendix A contain a complete set of values and healthy range profiles. The manually defined scoring profiles discussed at various points herein are also included.

Figure 16A:
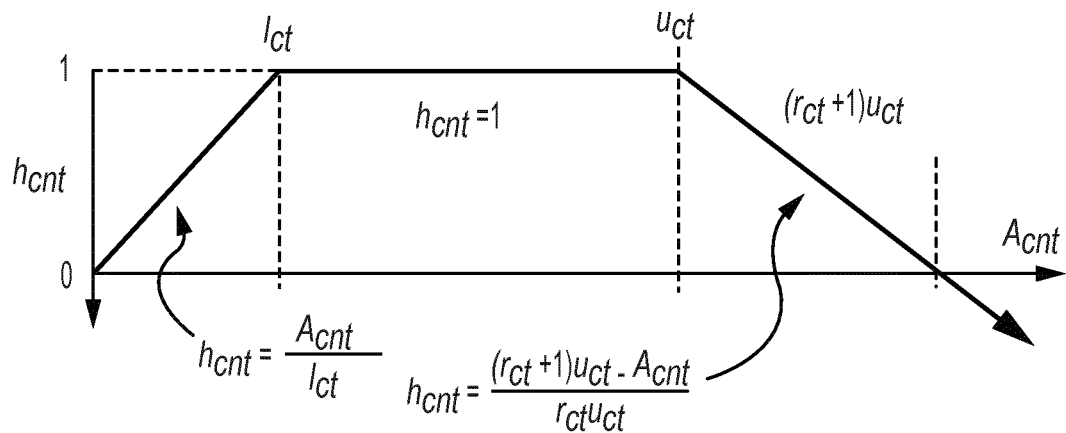
FIG. 16 illustrates a graphical representation of one embodiment of a set of equations for calculating nutritional health scores and other mathematical aspects of the system and methods disclosed herein.
Figure 16B:
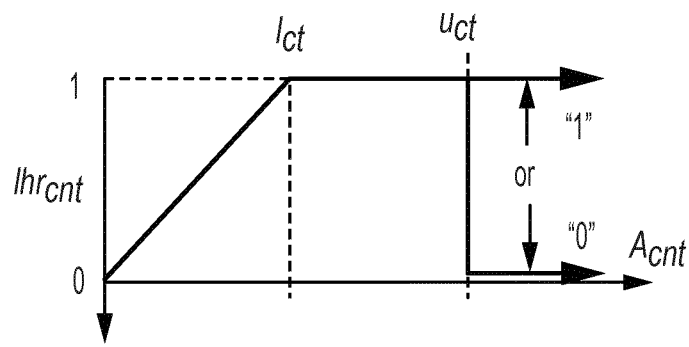
Figure 16C:
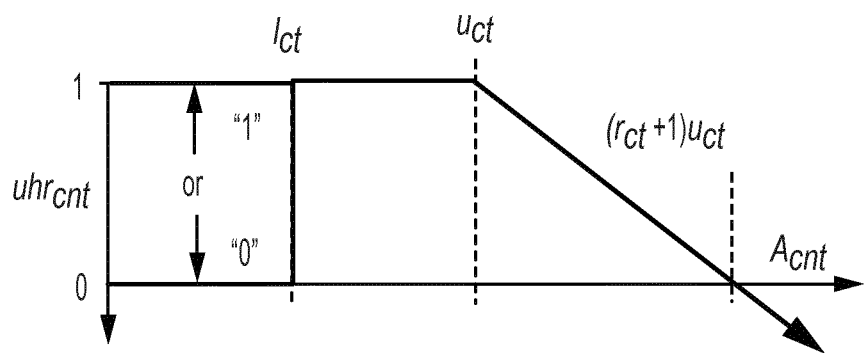

One embodiment of a graphical representation of the mathematics in equations 11, 12, and 13 above is shown in FIG. 16. In the illustrated embodiment, FIG. 16($a$) corresponds to equations 11, 12, and 13. FIG. 16($b$) shows the scoring functions for LHR{0,1}, while FIG. 16($c$) shows the scoring functions for UHR{0,1}.

Figure 17:
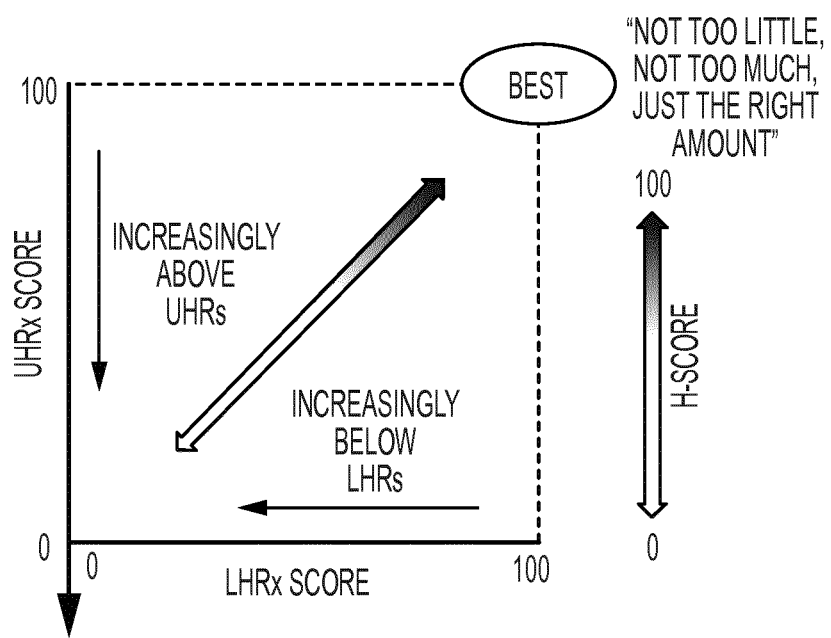
FIG. 17 illustrates a simplified schematic embodiment of a four quadrant graphic for determining an optimal score of a nutritional consumable according to embodiments of the system disclosed herein.

In an embodiment, the visualization in FIG. 15 can best be thought of as including four (4) quadrants where the upper right corner is the optimal score for a nutritional consumable. FIG. 17 illustrates a simplified schematic embodiment of this four quadrant idea.

In various embodiments, a single nutritional consumable can be scored using the system and methods disclosed herein. In some embodiments, the disclosed system and methods enable a meal or a diet (a set of nutritional consumables) to be composed of multiple foods (also nutritional consumables). The final nutritional consumable can be viewed as a sum of individual nutritional consumables. Hence, if there are i=1, 2, 3, . . . m sub nutritional consumables in n then:

$$A_{nt} = \Sigma_{\forall i} A_{n_i t}, \text{ and}$$

$$A_{cnt} = \Sigma_{\forall i} A_{n_i t} \delta_{cn_i},$$

In various embodiments, the measurable component amount is a function of the product of the amount consumed and measurable component density for each underlying item. Hence, in order to consume more of a measurable component c (e.g., a vitamin), the amount of a food containing that vitamin must increase or the vitamin nutrient density must increase in a given food.

The H-score can also be viewed as a function of calories rather than amount in grams. A simple relationship exists between the amount and energy of the nutritional consumable based on energy density.

$e_n$=energy density of nutritional consumable n in kcal per gram.

$k_{nt}=e_n A_{nt}$=energy (calories) consumed in a nutritional consumable n over time period t for amount $A_{nt}$.

$$A_{cnt} = A_{nt}\delta_{cn} = \frac{k_{nt}\delta_{cn}}{e_n},$$

where substitution into Equation 1 gives the general health score as a function of the energy consumed $k_{nt}$. Note Equation 2 can be extended to energy as well.

The NHF HEI scoring profile was created to define the HEI-2010 in the NHF with minimal modification. The NHF HEI utilizes the same HEI-2010 MCs and their weights. Normalized weights are illustrated in Table 1 above, but exact weight values used in HEI-2010 could be used without any alteration to the score. Moreover, NHF HEI tolerances were calculated from the max and min limits specified by HEI-2010 where the tolerance=min limit/max limit for "moderate" MCs. Since the NHF does not allow saturation, the fatty acid ratio was set to 0 which is the minimum limit as defined by HEI-2010. A NHF HEI healthy range profile was created to correspond to the defined min and max limits for each MC. Therefore the NHF HEI H-score utilizes the specific combination of NHF HEI scoring profile and NHF HEI healthy range profile.

The NHF NRF9.3 scoring profile and healthy range profiles used 9 positive nutrients and 3 (actually 4 MCs) nutrients to limit with the limits defined by the NRF9.3. All weights and tolerances were set to 1 in an attempt to most closely match the NRF9.3 model.

Two example DRI healthy range definitions are shown in Table 1 above for two populations "Female 31-50" and "Male 9-13." Two individuals with different genders or ages may have different scores based on differing LHR and UHR values, even if consuming the exact same diet or food. Similarly a single food will have a different score if scored toward different individuals. Nothing prevents using a single set of DV values to generate scores for a population, however, by using varying LHR and UHR values, the disclosed system and methods are actually measuring how well NCs meet the needs of the heterogeneous population as opposed to the needs of the fictitious 'average' person.

The explicit specification of time is important in LHR and UHR definitions and opens the possibility to design general nutritional health scores for the same population at different time-scales. As an example, the nutritional needs of a performance athlete may need to be specified in minutes or hours during a race, whereas in days or weeks while training. The science determining ULs also depends on the time-frame over which nutrients are consumed, for example in acute vs. chronic vitamin-A toxicity. The NHF enables the inclusion of this type of information.

The tolerance parameter is also a useful new feature in designing NHF scores to the needs of different individuals/populations. As a practical example, one might imagine the difference between a score designed to score foods for a diabetic vs. for a performance athlete. Given the desire for both people to remain below the same UHR for sugar consumption, the tolerance of the MC=sugar might conceivably be much lower for the diabetic vs. the athlete since the risks of short-term over consumption are higher.

While FIG. 11(a) depicts a piece-wise linear interpretation of a score for GNH, which has the benefit of simplicity, additional non-linear functions could also be used but at the expense of interpretability.

In addition to type of food, the amount (e.g., a sip versus 16 ounces of soda) would also have an impact on physiology and should impact a scoring system. Nutrient profiling has grappled with this issue, debating whether foods should be scored at 100 g, 100 kcal, or at a single serving. Existing DQIs have the same challenges. The HEI-2010 scores all diets at 1000 kcal independent of the amount actually consumed by an individual. The rational is to capture a measure of nutrient density because of the error in energy consumption. Mathematically, however, each score can be equivalently interpreted as 'scoring everything at 100 kcal or at 1000 kcal consumption.' Scoring both raw spinach (23 kcal/100 g) and roasted almonds (603 kcal/100 g) at either a fixed amount of 100 kcal or 100 g poses problems for comparison. Similarly, calculating the same score for a fixed composition diet regardless of whether 1000 kcal or 4000 kcal of it were consumed would not reflect the differences in physiological impact.

The GNH impact of a NC depends on both the individual consuming it and the amount consumed over a certain time frame. As an extreme example, a sugary soda consumed every day by a non-diabetic might be one factor in the long-term development of diabetes; in a hypoglycemic diabetic a sugary soda could be literally lifesaving; while in a hyperglycemic diabetic the consumption of the same sugary soda could be life threatening. Since the impact of consuming a sugary soda in these three cases for an individual in three different individual physiological states would differ, a single score would not be useful for deciding whether to consume the soda. Consumables are scored by their intrinsic chemical compositions for practical reasons, yet it is apparent that context matters.

Existing scoring tool definitions are not believed to have not been depicted graphically which might allow visual comparison across different methods and to the NHF. The scoring function implicitly used for the Healthy Eating Index 2010 (HEI 2010) is shown in FIG. 11(b), and the scoring function used across multiple nutrient profiling tools, such as the NRF9.3, in FIG. 11(c). While these tools may not initially have been defined as a function of amount, they in fact can be though of as producing a score at a specific amount (e.g. 100 kcal, 100 g, 1000 kcal) on these graphs. As a first step, MCs are split into two categories for both nutrient profiling and the HEI-2010. These categories are often considered as "positive" and "negative" nutrients which confounds the ability to define a score for a MC such as energy or macronutrients because DRI ranges are specified rather than a single threshold limit. Some nutritional fuzzy logic algorithms have recognized this limitation and specified healthy ranges in addition to positive and negative definitions. Nutrient profiling scores in FIG. 11(b) are unbounded, meaning they can grow arbitrarily large or small. The benefit of unbounded scoring is that it reflects the fact that consumption is unbounded. Unbounded scoring provides a continuous score across all consumption amounts. A consequence of unbounded scoring is scoring "positive" nutrients with increasingly higher scores at amounts above ULs. As an example of the consequences of the unbounded nature of the scoring function, the NRF9.3-100 kcal gives a score of −355 to sour pickles and a score of 2167 to fruit flavored drink made from powder with high vitamin C. While averaged values across food groups may seem reasonable, individual food scores are confusing.

In contrast to nutrient profiling in FIG. 11(c), the HEI 2010 score saturates in both negative and positive directions and is therefore bounded (FIG. 11(b)). The HEI-2010 specifies maximum and minimum scoring limits that define the slope of the scoring function (i.e. change in score as a function of change in amount). These min/max limits eliminate some properties of the unbounded nutrient profiling functions (FIG. 11(c)) and enable control over the slope of the score. However, the saturation (i.e., above the upper limit) in the HEI 2010 eliminates the ability of the score to measure incremental differences in diets. For example, a diet consisting of 80% empty calories will receive the same score as a diet consisting of 50% empty calories. The HEI 2010 also saturates the minimum score of adequate food components like the ratio of (polyunsaturated+monounsaturated) to saturated fat, which has a similar consequence of giving diets with different fatty acid ratios the same score below some threshold. An argument for saturation is to restrict the score to a value between 0-100. The final score in the NHF for a score below zero is set to zero for display purposes. An unbounded continuous score is mathematically more sound for both analytical and comprehension purposes.

The NHF framework (FIG. 11(a)) combines both saturation and an unbounded element to define a score that can be considered a hybrid between nutrient profiling and the HEI 2010 (or other DQIs). Minimum consumption for any NC by definition is zero: the score is 0 at zero amounts (left abscissa). This ensures incremental scoring change at any amount above zero consumption. The score saturates after the LHR is consumed, similar to the HEI 2010. If the LHR is set sufficiently high, the score will never saturate and incremental improvement can be measured, which is equivalent to the "positive" graph (FIG. 11(c)). However, it is not likely that any nutrient will have an increased benefit with increasing intake. Intake levels within the healthy range of consumption produce a maximal score in NHF, since by definition; intake is in the optimal range. In the (unlikely) event that an MC has an exact target intake, then the LHR and UHR can be set equal: the maximal score would occur only at one exact intake level. After consumption crosses the UHR, the MC function decreases indefinitely enabling incremental scoring with unbounded consumption. If the UHR is set to zero, then the scoring function reduces to the conceptually comparable unbounded "negative" score FIG. 11(c).

In the NHF, amounts within the healthy range of consumption produce a maximal score, since one cannot do any better. If an exact amount is targeted then the LHR and UHR can be set equal, which will produce a score that is only maximal at one exact amount. After consumption crosses the UHR the MC function decreases indefinitely enabling incremental scoring with unbounded consumption. If the UHR is set to zero, then the scoring function reduces to the conceptually comparable unbounded "negative" score in FIG. 11(c).

The tolerance in the NHF is used to define the slope of the graph above the UHR, similar in concept to the HEI 2010. Hence, the sensitivity to intake above UHR can be adjusted based on knowledge of the effect of high consumption on physiology resulting in changes in scores. The example of sugar intake in athletes versus diabetics provided above is applicable here: the sensitivity to increased consumption would be greater in the diabetic (the slope would be greater and the score affected more) compared to the athlete NHF combines many of the features of both nutrient profiling and DQIs into a single scoring function that can be used equivalently for both cases. Importantly the NHF makes no distinction between MCs, which eliminates the need to subjectively categorize MCs.

In various embodiments, the NRF_100 g score as well as the 100 kcal score is unbounded on the positive side. This may not be desirable due to upper limits on nutrients, like magnesium. For example "Rice bran, uncooked" in FNDDS has 781 mg of Magnesium where as the UL is 670. Therefore the assumption of endless positive is broken and the score cannot take this into account. Other examples are 100 g of "carrot chips, dried" which has 3423 ug vitamin A when the UL is 3000.

Alternatively, using the 100 kcal measure, a multivitamin, which has 0 calories cannot be scored properly yet could contributes significantly to the nutrient composition of what may be eaten. Two additional foods scored by NRF9.3-100 kcal, "Fruit flavored drink, made from powdered mix, low calorie, with high vitamin C" and "Cucumber pickles, sour" were selected as examples because of their extreme scores. The values of all FNDDS foods scored by NRF9.3-100 kcal can be found in the supplemental material attached hereto, and are also plotted as box-plots by food-group in FIG. 14. The cause of these extreme values lies in the combination of an unbounded scoring system as well as the nature of scoring at a fixed 100 kcal amount. In the case of 100 kcal scores, low calorie fortified foods will encounter these issues and demonstrate the need for a bounded scoring system that scores foods at variable intake amounts as the NHF does.

As in FIG. 11(*b*), the HEI thresholds upper limits to 0 at some maximum amount, which is the equivalent of setting the tolerance to this amount. However, the score does not change beyond this amount. The result is similar to the discussion below, where incremental improvement cannot be made as a result. For example if a limit for sugar has been achieved, no additional lowering of the score will occur for eating multiple packets of pure sugar when using an HEI score.

The design of the fatty acid score in the HEI-2010 highlights the consequence of saturating the score at low levels of intake. Saturation prevents measuring incremental diet improvements. In the HEI-2010, the fatty acid ratio of polyunsaturated (PUFA) and mono-unsaturated (MUFA) to saturated fat (SFA), computed as PUFA+MUFA/SFA, is given a maximum score if above 2.5 and a minimum score fixed to 0 if less than or equal to 1.5, where a maximum score is more desirable. Therefore, in HEI-2010, a fatty acid ratio of 0.5, 1.0, and 1.5 are all treated identically and given a score of 0. By definition in this scoring system, a ratio of 0.5 is not better than 1.5, yet this difference in a diet corresponds to 3 times more SFA in comparison to PUFA and MUFA. In HEI-2010 the limit 1.5 value was selected from the $15^{th}$ percentile of 1-day intake population distributions stating "this was necessary because clear evidence on the level of intake that warrants a score of zero is not available". To illustrate the limitations of the HEI scoring method, the instant application relies on a simple example from the Food and Nutrient Database for Dietary Studies (FNDDS) [http://www.ars.usda.gov/Services/docs.htm?docid=12089]. A piece of "Pizza, cheese, stuffed crust" (148 g) contains PUFA=2.3 g, MUFA=4.1 g, SFA=8.6 g, yielding a (PUFA+MUFA)/SFA=0.74. This fatty acid ratio of pizza is 2 times lower than the specified minimum-scoring limit in the HEI-2010. Logic dictates that if a higher ratio is viewed as generally better and incremental improvement should be reflected in a score, then the lowest score possible should be 0 (even in the case where absolute 0 may not exist). The HEI measure of fatty acid ratios is incapable of capturing incremental improvement for a major component of many diets: pizza. The capability to incrementally score a diet consisting almost entirely of pizza, as it improves, should be possible. The scenario, while extreme, is not unimaginable, and a scoring system incapable of incremental improvement is not the most robust basis for measuring national guidelines. Utilizing the NHC framework for the next generation HEI could aid in a scoring design without this issue and prevent the introduction of other similar issues.

The above description of is exemplary of the features of the system disclosed herein. As noted, the disclosed systems and methods could be used to calculate scores indicating the impact of consumption of consumables on individuals or environmental factors based on any appropriate measurable characteristic of a consumable, and are not limited to determining nutritional value scores. Moreover, the functionality of the above-described system is not limited to the functionalities indicated herein. It should be understood that various changes and modifications to the presently disclosed embodiments will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A nutritional health score determination system comprising:
   a caloric intake range calculation module configured to calculate a caloric intake range for a user by multiplying a standard caloric intake range by a calorie multiplier determined, at least in part, by a characteristic of the user;
   a consumable input module configured to cause at least one display device to display a consumable entry control to enable the user to specify at least one consumable and at least one amount for said at least one consumable;
   a nutrient health score calculation module configured to calculate a nutrient health score for each of a plurality of nutrients by determining the value of a piecewise continuous nutrient health score function wherein for each of the plurality of nutrients:
      (a) the nutrient health score function for that nutrient has a first value for a zero amount of that nutrient, and
      (b) the nutrient health score function for that nutrient has increasing values for amounts of that nutrient greater than zero and less than a lower healthy range value, a constant value for amounts of that nutrient between the lower healthy range value and an upper healthy range value, and decreasing values for amounts of that nutrient greater than the upper healthy range value;
   a nutritional health score calculation module configured to calculate a plurality of nutritional health scores based on the nutrient health scores for the plurality of different amounts of at least one of the plurality of nutrients and at least one weighting value, a user interface display module configured to cause the at least one display device to:
    display a curve representing the plurality of nutritional health scores for a plurality of amounts of the at least one consumable,
    indicate on the curve a current health score of a current diet and the maximum nutrient health score that can be achieved by the current diet,
    display first consumable items that, if consumed, would increase the user's nutritional health score,
    indicate second consumable items in the current diet that, if removed, would increase the user's nutritional health score, and
    display a new nutritional health score on the curve when the user, by the consumable input module, adds at least one of the first consumable items or removes at least one of the second consumable items; and
a recommendation module configured to operate with the nutritional health score calculation module to determine a plurality of potential nutritional health scores for the first consumable items and to recommend at least one of the first consumable items that results in a highest potential nutritional health score,
wherein each of the modules is software executed by a general purpose computer,
wherein the nutritional health score determination system is configured to automatically calculate at least two different nutritional health scores for a particular consumable, the at least two different nutritional health scores comprising a first score that is a nutritional content of a current or actual amount of the particular consumable that is consumed and further comprising a second score that is a highest possible score for the particular consumable, wherein the amount of the particular consumable consumed for a set period of time is variable, and
wherein the nutritional health score determination system is configured to automatically (i) place orders for delivery of food needed to prepare a diet based on the plurality of nutritional health scores and/or (ii) place orders based on what is indicated as being in stock at a local grocer.

2. The nutritional health score determination system of claim 1, wherein the caloric intake range calculation module is configured to cause the at least one display device to display an activity input control to enable the user to indicate the characteristic of the user.

3. The nutritional health score determination system of claim 1, which includes an activity monitor, and wherein the caloric intake range calculation module is configured to receive data from the activity monitor indicative of the characteristic of the user.

4. The nutritional health score determination system of claim 1, wherein the nutrient health score function for at least one of the plurality of nutrients has a value for zero-crossing amounts of the at least one of the plurality of nutrients for which the nutrient health score function is less than the first value, the zero-crossing amounts being based on a sensitivity value for the at least one nutrient of the plurality of nutrients.

5. The nutritional health score determination system of claim 4, wherein the sensitivity value is inversely related to the user's sensitivity to the at least one nutrient of the plurality of nutrients.

6. The nutritional health score determination system of claim 1, which includes a plurality of tables of weighting values each specific to a particular population of individuals, and wherein the nutritional health score calculation module determines one of the plurality of tables of weighting values to use to calculate the plurality of nutritional health scores based, at least in part, on the characteristic of the user.

7. The nutritional health score determination system of claim 6, wherein the characteristic of the user includes at least one selected from the group consisting of an activity level of the user, an age of the user, a gender of the user, a weight of the user, a Body Mass Index (BMI) of the user, and a medical condition of the user.

8. The nutritional health score determination system of claim 1, wherein the recommendation module is configured to cause the at least one display device to display at least one control to enable the user to add the recommended at least one of the first consumable items to the current diet.

9. The nutritional health score determination system of claim 1, wherein the recommendation module is configured to cause the at least one display device to display at least one control to enable the user to remove at least one of the second consumable items in the current diet.

10. The nutritional health score determination system of claim 1, wherein the nutritional health score calculation module is further configured to determine the maximum nutritional health score for the current diet.

11. The nutritional health score determination system of claim 1, wherein the nutritional health score calculation module is configured to calculate the plurality of nutritional health scores based on the nutrient health scores for a set containing fewer than all of the nutrients tracked by the nutritional health score determination system, the set based on a desired scoring profile for the user.

12. The nutritional health score determination system of claim 1, which includes a nutrient subset control that enables the user to indicate a desired subset of nutrients, and wherein the nutritional health score calculation module is configured to calculate the plurality of nutritional health scores based on the nutrient health scores for the desired subset of nutrients.

* * * * *